US011187711B1

(12) United States Patent
Lynn et al.

(10) Patent No.: US 11,187,711 B1
(45) Date of Patent: Nov. 30, 2021

(54) ANALYTE DETECTION FROM BREATH SAMPLES

(71) Applicant: Hound Labs, Inc., Oakland, CA (US)

(72) Inventors: Michael Scott Lynn, Piedmont, CA (US); Joseph A. Heanue, Fremont, CA (US); Samartha G. Anekal, Fremont, CA (US); Kevin M. Limtao, Milpitas, CA (US); Kevin Bradford Dunk, Castro Valley, CA (US); Jeffrey A. Schuster, Bolinas, CA (US)

(73) Assignee: Hound Labs, Inc., Oakland, CA (US)

( * ) Notice: Subject to any disclaimer, the term of this patent is extended or adjusted under 35 U.S.C. 154(b) by 84 days.

(21) Appl. No.: 16/124,181

(22) Filed: Sep. 6, 2018

Related U.S. Application Data

(60) Provisional application No. 62/646,798, filed on Mar. 22, 2018, provisional application No. 62/616,380, (Continued)

(51) Int. Cl.
*G01N 33/94* (2006.01)
*A61B 10/00* (2006.01)
(Continued)

(52) U.S. Cl.
CPC ........... *G01N 33/948* (2013.01); *A61B 10/00* (2013.01); *B01L 3/5027* (2013.01); *B01L 3/50273* (2013.01); *B01L 3/502715* (2013.01); *B01L 3/502738* (2013.01); *B01L 3/502746* (2013.01); *G01N 33/497* (2013.01); *G01N 33/4972* (2013.01); *G01N 33/542* (2013.01);
(Continued)

(58) Field of Classification Search
CPC ............... G01N 33/948; G01N 33/497; G01N 33/4972; G01N 33/542; G01N 33/54306; G01N 33/98; A61B 10/00; A61B 2010/0009; A61B 2010/0087; B01L 3/5027; B01L 3/502715; B01L 3/50273; B01L 3/502738; B01L 3/502746; B01L 2300/02; B01L 2300/0636; B01L 2400/049; B01L 2400/0638
See application file for complete search history.

(56) References Cited

U.S. PATENT DOCUMENTS 3,086,833 A   4/1963   Streck
3,393,108 A   7/1968   Jones
(Continued)

FOREIGN PATENT DOCUMENTS

EP   132313    9/1991
EP   2781917   9/2014
(Continued)

OTHER PUBLICATIONS

"Alexander, Brentan R. Design of a microbreather for two-phase microchannel devices. Diss. Massachusetts Institute of Technology, 2008." (Year: 2008).*
(Continued)

*Primary Examiner* — Samuel P Siefke
*Assistant Examiner* — Oyeleye Alexander Alabi
(74) *Attorney, Agent, or Firm* — Weaver Austin Villeneuve & Sampson LLP

(57) ABSTRACT

Systems and techniques for collecting and analyzing breath samples to detect one or more target analytes are disclosed.

21 Claims, 48 Drawing Sheets

Related U.S. Application Data filed on Jan. 11, 2018, provisional application No. 62/557,060, filed on Sep. 11, 2017, provisional application No. 62/557,056, filed on Sep. 11, 2017.

(51) Int. Cl.
| | |
|---|---|
| *G01N 33/543* | (2006.01) |
| *G01N 33/542* | (2006.01) |
| *G01N 33/497* | (2006.01) |
| *G01N 33/98* | (2006.01) |
| *B01L 3/00* | (2006.01) |

(52) U.S. Cl.
CPC ....... *G01N 33/54306* (2013.01); *G01N 33/98* (2013.01); *A61B 2010/0009* (2013.01); *A61B 2010/0087* (2013.01); *B01L 2300/02* (2013.01); *B01L 2300/0636* (2013.01); *B01L 2400/049* (2013.01); *B01L 2400/0638* (2013.01)

(56) References Cited

U.S. PATENT DOCUMENTS

| | | | |
|---|---|---|---|
| 3,676,072 | A | 7/1972 | Krivis |
| 4,133,202 | A | 1/1979 | Marple |
| 4,232,667 | A | 11/1980 | Chalon et al. |
| 4,288,344 | A | 9/1981 | Reiss |
| 4,771,005 | A | 9/1988 | Spiro |
| 5,026,027 | A | 6/1991 | Hamilton |
| 5,103,857 | A | 4/1992 | Kuhn |
| 5,140,993 | A | 8/1992 | Opekun et al. |
| 5,361,771 | A | 11/1994 | Craine et al. |
| 5,922,610 | A | 7/1999 | Alving et al. |
| 6,067,983 | A | 5/2000 | Stenzler |
| 6,326,159 | B1* | 12/2001 | Ullman ............. C07K 16/42 435/18 |
| 6,537,823 | B1 | 3/2003 | Smith |
| 6,582,376 | B2 | 6/2003 | Baghdassarian |
| 6,605,444 | B1 | 8/2003 | Klein et al. |
| 7,059,349 | B2 | 6/2006 | Breda |
| 7,364,553 | B2 | 4/2008 | Paz et al. |
| 7,547,285 | B2 | 6/2009 | Kline |
| 8,237,118 | B2 | 8/2012 | Prox et al. |
| 8,586,932 | B2 | 11/2013 | Rousso et al. |
| 8,705,029 | B2 | 4/2014 | Palmskog et al. |
| 8,707,758 | B2 | 4/2014 | Keays |
| 8,955,366 | B2 | 2/2015 | Abraham-Fuchs et al. |
| 9,429,564 | B2 | 8/2016 | Beck |
| 9,709,581 | B1 | 7/2017 | Gordon et al. |
| 9,709,582 | B1 | 7/2017 | Gordon et al. |
| 9,726,684 | B1 | 8/2017 | Gordon et al. |
| 9,921,234 | B1 | 3/2018 | Lynn et al. |
| 9,933,445 | B1 | 4/2018 | Lynn et al. |
| 9,945,878 | B1 | 4/2018 | Gordon et al. |
| 9,970,950 | B1 | 5/2018 | Lynn et al. |
| 9,976,944 | B2 | 5/2018 | Olin et al. |
| 10,226,201 | B2 | 3/2019 | Ahmad et al. |
| 10,247,742 | B1 | 4/2019 | Lynn et al. |
| 10,408,850 | B1 | 9/2019 | Gordon et al. |
| 10,557,563 | B2 | 2/2020 | Thurau |
| 10,641,783 | B2 | 5/2020 | Lynn et al. |
| 10,955,428 | B2 | 3/2021 | Lynn et al. |
| 2002/0177232 | A1 | 11/2002 | Melker et al. |
| 2003/0153844 | A1 | 8/2003 | Smith |
| 2004/0043479 | A1 | 3/2004 | Briscoe et al. |
| 2005/0105077 | A1 | 5/2005 | Padmanabhan et al. |
| 2005/0137491 | A1 | 6/2005 | Paz et al. |
| 2006/0094123 | A1 | 5/2006 | Day et al. |
| 2006/0257941 | A1* | 11/2006 | McDevitt ............ G01N 1/4077 435/7.2 |
| 2007/0031283 | A1* | 2/2007 | Davis ............... A61B 5/150221 422/400 |
| 2007/0077660 | A1 | 4/2007 | Glas |
| 2008/0004542 | A1 | 1/2008 | Allen et al. |
| 2009/0017555 | A1 | 1/2009 | Jehanli et al. |
| 2010/0297635 | A1 | 11/2010 | Olin et al. |
| 2011/0086364 | A1 | 4/2011 | Takkinen et al. |
| 2012/0302907 | A1 | 11/2012 | Palmskog et al. |
| 2013/0006068 | A1 | 1/2013 | Gemer et al. |
| 2013/0021153 | A1 | 1/2013 | Keays |
| 2013/0102018 | A1* | 4/2013 | Schentag ........... A61B 5/14507 435/25 |
| 2013/0165806 | A1 | 6/2013 | Wondka et al. |
| 2014/0094391 | A1* | 4/2014 | McDevitt .......... A61B 10/0051 506/18 |
| 2014/0288454 | A1 | 9/2014 | Paz et al. |
| 2014/0366609 | A1 | 12/2014 | Beck et al. |
| 2015/0025407 | A1 | 1/2015 | Eichler et al. |
| 2015/0033824 | A1 | 2/2015 | Hammarlund et al. |
| 2015/0065901 | A1 | 3/2015 | Bhatnagar et al. |
| 2015/0265184 | A1 | 9/2015 | Wondka et al. |
| 2015/0305651 | A1 | 10/2015 | Attariwala et al. |
| 2015/0369830 | A1 | 12/2015 | Crichlow |
| 2016/0000358 | A1 | 1/2016 | Lundin et al. |
| 2017/0128692 | A1 | 5/2017 | Christopher et al. |
| 2017/0184609 | A1 | 6/2017 | Milton et al. |
| 2017/0303822 | A1 | 10/2017 | Allsworth et al. |
| 2017/0303823 | A1 | 10/2017 | Allsworth et al. |
| 2018/0120278 | A1* | 5/2018 | Hoorfar ............... G01N 33/497 |
| 2018/0224471 | A1 | 8/2018 | Lynn et al. |
| 2018/0238916 | A1 | 8/2018 | Lynn et al. |
| 2018/0306775 | A1 | 10/2018 | Beck et al. |
| 2020/0147333 | A1 | 5/2020 | Stoll et al. |
| 2020/0182892 | A1 | 6/2020 | Lynn et al. |
| 2020/0245898 | A1 | 8/2020 | Heanue et al. |
| 2020/0245899 | A1 | 8/2020 | Heanue et al. |
| 2020/0300876 | A1 | 9/2020 | Lynn et al. |

FOREIGN PATENT DOCUMENTS

| | | | |
|---|---|---|---|
| WO | 90/14043 | 11/1990 | |
| WO | 2006/083269 | 8/2006 | |
| WO | 2011/029889 | 3/2011 | |
| WO | WO-2016065300 A1 * | 4/2016 | ........... B01L 3/5027 |
| WO | 2018/185164 | 10/2018 | |
| WO | 2018/211280 | 11/2018 | |
| WO | 2019/011750 | 11/2019 | |
| WO | 2020/097382 | 5/2020 | |
| WO | 2020/159698 | 8/2020 | |

OTHER PUBLICATIONS

U.S. Appl. No. 14/997,405, Notice of Allowance dated May 10, 2017.
U.S. Appl. No. 14/997,405, Office Action dated Jan. 9, 2017.
U.S. Appl. No. 14/997,405, Corrected Notice of Allowability dated Jun. 15, 2017.
U.S. Appl. No. 15/143,379, Office Action dated Oct. 25, 2016.
U.S. Appl. No. 15/143,379, Notice of Allowance dated Mar. 21, 2017.
U.S. Appl. No. 15/143,379, Notice of Allowability dated Jun. 13, 2017.
U.S. Appl. No. 15/143,328, Office Action dated Sep. 1, 2016.
U.S. Appl. No. 15/143,328, Notice of Allowance dated Feb. 10, 2017.
U.S. Appl. No. 15/143,328, Notice of Allowability dated May 18, 2017.
U.S. Appl. No. 15/143,328, Notice of Allowance dated Jun. 14, 2017.
U.S. Appl. No. 15/650,518, Office Action dated Oct. 4, 2017.
U.S. Appl. No. 15/650,518, Notice of Allowance dated Feb. 1, 2018.
U.S. Appl. No. 14/641,412, Office Action dated May 19, 2016.
U.S. Appl. No. 14/641,412, Final Office Action dated Dec. 5, 2016.
U.S. Appl. No. 14/641,412, Office Action dated Jun. 26, 2017.
U.S. Appl. No. 14/641,412, Notice of Allowance dated Jan. 9, 2018.
U.S. Appl. No. 14/641,412, Corrected Notice of Allowability dated Apr. 18, 2018.
U.S. Appl. No. 15/217,151, Office Action dated Jan. 9, 2017.
U.S. Appl. No. 15/217,151, Office Action dated May 16, 2017.

(56) References Cited

OTHER PUBLICATIONS

U.S. Appl. No. 15/217,151, Final Office Action dated Oct. 30, 2017.
U.S. Appl. No. 15/217,151, Notice of Allowance dated Dec. 22, 2017.
U.S. Appl. No. 15/217,264, Office Action dated Oct. 24, 2016.
U.S. Appl. No. 15/217,264, Office Action dated Mar. 20, 2017.
U.S. Appl. No. 15/217,264, Final Office Action dated Aug. 16, 2017.
U.S. Appl. No. 15/217,264, Notice of Allowance dated Nov. 16, 2017.
Adams, I.B. et al., "Cannabis: pharmacology and toxicology in animals and humans," Addiction, Nov. 1996;91 (11): 1585-614, PubMed abstract 8972919.
Al-Asmari, Ahmed et al., "Method for the quantification of diamorphine and its metabolites in pediatric plasma samples by liquid chromatography-tandem mass spectrometry," Journal of Analytical Toxicology, vol. 34, May 2010.
Atkinson, H.C. et al., "Drugs in human milk. Clinical pharmacokinetic considerations." Clin Pharmacokinet. Apr. 1988; 14(4):217-40, PubMed abstract 3292101.
Azorlosa, J.L. et al., "Marijuana smoking: effect of varying delta 9-tetrahydrocannabinol content and number of puffs," J. Pharmacol. Exper. Ther 1992;261:114, abstract.
Bailey, J.R. et al., "Fetal disposition of delta 9-tetrahydrocannabinol (THC) during late pegnancy in the rhesus monkey," Toxicol Appl Pharmacol. Sep. 15, 1987; 90(2): 315-21, abstract.
Baker, D. et al., "Cannabinoids control spasticity and tremor in a multiple sclerosis model," Nature, Mar. 2, 2000;404(6773):84-7, abstract.
Balabanova, S. et al., "Detection of drugs in sweat," Belt Gerichtl Med. 1990;48:45-9, abstract.
Bashir, W. et al., "Spectrophotometric Determination of Acetone in Acetic Acid", Microchemical Journal, 1983, 28, pp. 77-81.
Beck, Olof et al., "Detection of Delta9-tetrahydrocannabinol in exhaled breath collected from cannabis users," Journal of Analytical Toxicology, vol. 35, Oct. 2011.
Benowitz, Neal L. et al., "Metabolic and psychophysiologic studies of cannabidiol-hexobarbital interaction," Clinical Pharmacology and Therapeutics (1980) 28, 115-120, abstract.
Blanc, Jennifer A. et al., "Adsorption losses from urine-based cannabinoid calibrators during routine use," Clin. Chem. 39/8, 1705-1712 (1993).
Bloom, A.S., Effect of delta9-tetrahydrocannabinol on the synthesis of dopamine and norepinephrine in mouse brain synaptosomes, J Pharmocol Exp Ther. Apr. 1982;221(1):97-103.
Bornheim, Lester M. et al., "Characterization of cytochrome P450 3A inactivation by cannabidiol: possible involvement of cannabidiol-hydroxyquinone as a P450 inactivator," Chem. Res. Toxicol., 1998, 11 (10), pp. 1209-0450.
Bornheim, L.M. et al., "Human hepatic microsomal metabolism of delta 1-tetrahydrocannabinol," Drug Metab Dispos. Mar.-Apr. 1992;20(2):241-6, PubMed abstract 1352216.
Brenneisen, R. et al., "The effect of orally and rectally administered delta 9-tetrahydrocannabinol on spaticity: a pilot study with 2 patients," Int J Clin Pharmocol Ther. Oct. 1996;34(10):446-52.
Brunet, B. et al., "Validation of large white pig as an animal model for the study of cannabinoids metabolism: application to the study of THC distribution in issues," Forensic Sci Int. Sep. 12, 2006;161(2-3):169-74, PubMed abstract 16859848.
Burstein, S. et al., "Isolation and characterization of two major urinary metabolites of 1-tetrahydrocannabinol," Science, Apr. 28, 1972;176(4033):422-3, PubMed abstract 5026162.
Cami, J. et al., "Effect of subject expectancy on the THC intoxication and disposition from smoked hashish cigarettes," Pharmacology Biochemistry and Behavior, vol. 40, Issue 1, Sep. 1991, pp. 115-119.
Challapalli, P.V. et al., "In vitro experiment optimization for measuring tetrahydrocannabinol skin permeation," Int J Pharm. Jul. 25, 2002;241(2):329-39, PubMed abstract 12100860.
Chaturvedi, Arvind K., "Postmortem aviation forensic toxicology: an overview," Journal of Analytical Toxicology, vol. 34, May 2010.

"The Chemistry of Phenols," Zvi Rappoport, editor, © 2003 John Wiley & Sons, Ltd. ISBN: 0-471-49737-1.
Chiang, C. Nora et al., "Prenatal drug exposure: kinetics and dynamics," NIDA Research Monograph 60, 1985.
Christophersen, Asbjorg Solberg et al., "Tetrahydrocannabinol stability in whole blood: plastic versus glass containers," Journal of Analytical Toxicology, vol. 10, Jul./Aug. 1986.
Cirimele, V. et al., "Testing human hair for cannabis. III. Rapid screening procedure for the simultaneous identification of delta9-tetrahydrocannabinol, cannabinol, and cannabidiol," Journal of Analytical Toxicology, vol. 20, Jan./Feb. 1996.
Cone, Edward J. et al., "In vivo adulteration: excess fluid ingestion causes false-negative marijuana and cocaine urine test results," Journal of Analytical Toxicology, vol. 22, Oct. 1998.
Cone, Edward J. et al., "Marijuana-laced brownies: behavioral effects, physiologic effects, and urinalysis in humans following ingestion," Journal of Analytical Toxicology, vol. 12, Jul./Aug. 1988.
Cone, Edward J. et al., "Passive inhalation of marijuana smoke: urinalysis and room air levels of delta-9-tetrahydrocannabinol," Juornal of Analytical Toxicology, vol. 11, May/Jun. 1987.
Crouch, Dennis J. et al., "An evaluation of selected oral fluid point-of-collection drug-testing devices," Journal of Analytical Toxicology, vol. 29, May/Jun. 2005.
Crouch, D.J., "Oral fluid collection: the neglected variable in oral fluid testing," Forensic Sci Int. Jun. 10, 2005; 150(2-3): 165-73, PubMed abstract 15899565.
Day, David et al., "Detection of THCA in oral fluid by GC-MS-MS," Journal of Analytical Toxicology, vol. 30, Nov./Dec. 2006.
D'Sourza, Deepak Cyril et al., "The psychotomimetic effects of intravenous delta-9-tetrahydrocannabinol in healthy individuals: implications for psychosis," Neuropsychopharmacology (2004) 29, 1558-1572.
Ellis, G.M. Jr. et al., "Excretion patterns of cannabiniod metabolites after last use in a group of chronic users," Clin Pharmacol Ther. Nov. 1985;38(5):572-8, PubMed abstract 3902318.
Ellis, George M. Jr. et al. "Excretion patterns of cannabinoid metabilites after last use," 420 Magazine, Oct. 4, 2011, downloaded from https: //www.420magazine.com/forums/drug-testing-urine/ 153724.
Elsohly, M. et al., "Potency trends of Delta9-THC and other cannabinoids in confiscated marijuana from 1980-1997," Journal of Forensic Sciences, vol. 45, No. 1, 2000, pp. 24-30.
Feng, Shixia et al., "Simultaneous analysis of Delta9-THC and its major metabolites in urine, plasma, and meconium by GC-MS using an immunoaffinity extraction procedure," Journal of Analytical Toxicology, vol. 24, Sep. 2000.
Fraser, A.D et al., "Monitoring urinary excretion of cannabinoids by fluorescence-polarization immunoassay: a cannabiniod-to-creatinine ratio study," Ther Drug Monit. Dec. 2002;24(6):746-50, PubMed abstract 12451292.
Fraser, A.D et al., "Urinary excretion profiles of 11-nor9-carboxy-delta9-tetrahydrocannabinol and 11-hydroxy-delta9-THC: cannabinoid metabolites to creatinine ratio study IV," Forensic Sci Int. Jul. 16, 2004; 143(2-3): 147-52, PubMed abstract 15240035.
Fraser, A.D. et al., "Urinary excretion profiles of 11-nor-9-carboxy-Delta9-tetrahydrocannabinol. Study III. A Delta9-THC-COOH to creatinine ratio study," Forensic Sci Int. Nov. 26, 2003; 137(2-3): 196-202, PubMed abstract 14609657.
Garrett, E.R. et al., "Pharmacokinetics of delta9-tetrahydrocannabinol in dogs," J Pharm Sci. Mar. 1977;66(3):395-407, PubMed abstract 845807.
Garrett, Edward R. et al., "Physicochemical properties, solubility, and protein binding of Delta9-tetrahydrocannabinol," J Pharm Sci. Jul. 1974;63(7): 1056-64, abstract.
Gjerde, Hallvard et al., "Comparison of drug concentrations in blood and oral fluid collected with the Intercept® sampling device," Journal of Analytical Toxicology, vol. 34, May 2010.
Gjerde, H. et al., "Incidence of alcohol and drugs in fatally injured car drivers in Norway," Accid Anal Prev. Aug. 1993;25(4):479-83, PubMed abstract 8357462.
Goodwin, R.S. et al., "Delta(9)-tetrahydrocannabinol, 11-hydroxy-delta(9)-tetrahydrocannabinol and 11-nor-9-carboxy-delta(9)-

(56) References Cited

OTHER PUBLICATIONS tetrahydrocannabinol in human plasma after controlled oral administration of cannabinoids," Ther Drug Monit. Aug. 2006;28(4):545-51, PubMed abstract 16885723.
Green, Mitchell D. et al., "Glucuronidation of opioids, carboxylic acid-containing drugs, and hydroxylated xenobiotics catalyzed by expressed monkey UDP-glucuronosyltransferase 2B9 protein," Drug Metabolism and Disposition, vol. 25, No. 12, (1997).
Gross, Stanley J. et al., "Detection of recent cannabis use by saliva Delta9-THC radioimmunoassay," Journal of Analytical Toxicology, vol. 9, Jan./Feb. 1985.
Grotenhermen, F., "Pharmacokinetics and pharmacodynamics of cannabinids," Clin Pharmacokinet. 2003;42(4):327-60, PubMed abstract 12648025.
Gustafson, Richard A. et al., "Urinary cannabinoid detection times after controlled oral administration of Delta9-tetrahydrocannabinol to humans," Clinical Chemistry 49:7, 1114-1124 (2003).
Gustafson, Richard A. et al., "Urinary pharmacokinetics of 11-Nor-9-carboxy-delta9-tetrahydrocannabinol after controlled oral delat9-tetrahydrocannabinol administration," Journal of Analytical Toxicology, vol. 28, Apr. 2004.
Gustafson, R.A. et al., "Validated method for the simultaneous determination of Delta 9-tetrahydrocannabinol (THC), 11-hydroxy-THC and 11-nor-9-carboxy-THC in human plasma using solid phase extraction and gas chromatography-mass spectrometry with positive chemical ionization," J. Chromatogr B Analyt Technol Biomed Life Sci, Dec. 5, 2003;798(1): 145-54, PubMed abstract 14630369.
Guy, G.W. et al., "A phase I, double blind, three-way crossover study to assess the pharmacokinetic profile of cannabis based medicine extract (CBME) administered sublingually in variant cannabinoid ratios in normal healthy male volunteers (GWPK0215)," Journal of Cannabis Therapeutics, vol. 3, No. 4, 2003, pp. 121-152.
Hall, B.J. et al., "Determination of cannabinoids in water and human saliva by solid-phase microextraction and quadrupole ion trap gas chromatography/mass spectrometry," Anal chem. May 1, 1998;70(9): 1788-96, PubMed abstract 9599579.
Halldin, M.M. et al., "Identification of in vitro metabolites of delta 1-tetrahydrocannabinol formed by human livers," Drug Metab Dispos. Jul.-Aug. 1982; 10(4):297-301, PubMed abstract 6126323.
Hampson, A.J et al., "Cannabidiol and (-)delta9-tetrahydrocannabinol are neuroprotective antioxidants," Proc Natl Acad Sci U.S.A. Jul. 7, 1998; 95(14): 8268-8273.
Hanson, V.W. et al., "Comparison of 3H- and 125I-radioimmunoassay and gas chromatography/mass spectrometry for the determination of delta9-tetrahydrocannabinol and cannabinoids in blood and serum," Journal of Analytical Toxicology, vol. 7, Mar./Apr. 1983.
Harder, S. et al., "Concentration-effect relationship of delta-9-tetrahydrocannabiol and prediction of psychotropic effects after smoking marijuana," Int J Clin Pharmacol Ther. Apr. 1997;35(4):155-9, PubMed abstract 9112136.
Harvey, D.J. et al., "Metabolites of cannabidiol identified in human urine," Xenobiotic, Mar. 1990;20(3):303-20, PubMed abstract 2336840.
Hawks, Richard L., "The Analysis of Cannabinoids in Biological Fluids," NIDA Research Monograph 42, 1982.
Hazekamp, Arno et al., "Cannabis; extracting the medicine," thesis/dissertation 2007.
"Information for health care professionals: cannabis (marihuana, marijuana) and the cannabinoids," Health Canada, Feb. 2013.
Heishman, Stephen J. et al., "Effects of tetrahydrocannabinol content on marijuana smoking behavior, subjective reports, and performance," Pharmacology Biochemistry and Behavior, vol. 34, Issue 1, Sep. 1989, pp. 173-179, abstract.
Himes, Sarah K. et al., "Cannabinoids in exhaled breath following controlled administration of smoked cannabis," Clinical chemistry 59:12 1780-1789 (2013).
Huang, Wei et al., "Simultaneous determination of delta9-tetrahydrocannabinol and 11-nor-9-carboxy-delta9-tetrahydrocannabinol in human plasma by solid-phase extraction and gas chromatography-negative ion chemical ionization-mass spectrometry," Journal of Analytical Toxicology, vol. 25, Oct. 2001.
Huestis, Marilyn A. et al., "Blood cannabinoids. I. Absorption of THC and formation of 11-OH-THC and THCCOOH during and after smoking marijuana," Journal of Analytical Toxicology, vol. 16, Sep./Oct. 1992.
Huestis, Marilyn A. et al., "Blood cannabinoids. II. Models for the prediction of time of marijuana exposure from plasma concentraitons of delta9-tetrahydrocannabinol (THC) and 11-nor-9-carboxy-delta9-tetrahydrocannabinol (THCCOOH)," Journal of Analytical Toxicology, vol. 16, Sep./Oct. 1992.
Huestis, Marilyn A. et al., "Cannabinoid concentrations in hair from documented cannabis users," Forensic Sci Int. Jul. 4, 2007; 169(2-3): 129-136.
Huestis, Marilyn A. et al., "Alternative testing matrices," chapter 11 of the Drug Abuse Handbook, 1998 CRC Press LLC, ISBN 0-8493-2637-0.
Huestis, M.A. et al., "Characterization of the absorption phase of marijuana smoking," Clin Pharmacol Ther. Jul. 1992;52(1):31-41, PubMed abstract 1320536.
Huestis, Marilyn A. et al., "Detection times of marijuana metabolites in urine by immunoassay and GC-MS," Journal of Analytical Toxicology, vol. 19, Oct. 1995.
Huestis, Marilyn A. et al., "Differentiating new marijuana use from residual drug excretion in occasional marijuana users," Journal of Analytical Toxicology, vol. 22, Oct. 1998.
Huestis, Marilyn A. et al., "Estimating the time of last cannabis use from plasma delta9-tetrahydrocannabinol and 11-nor-9-carboxy-delta9-tetrahydrocannabinol concentrations," Clinical Chemistry 51:12 2289-2295 (2005).
Huestis, Marilyn A., "Human cannabinoid pharmacokinetics," Chem Biodivers. Aug. 2007; 4(8): 1770-1804.
Huestis, Marilyn A. et al., "Relationship of delta9-tetrahydrocannabinol concentrations in oral fluid and plasma after controlled administration of smoked cannabis," Journal of Analytical Toxicology, vol. 28, Sep. 2004.
Huestis, Marilyn A. et al., "Urinary excretion profiles of 11-nor-9-carboxy-delta9-tetrahydrocannabinol in humans after single smoked doses of marijuana," Journal of Analytical Toxicology, vol. 20, Oct. 1996.
Hunt, C.A. et al., "Evidence that cannabidiol does not significantly alter the pharmacokinetics of tetrahydrocannabinol in man," J Pharmacokinet Biopharm. Jun. 1981;9(3):245-60, PubMed abstract 6270295.
Hunt, C.A. et al., "Tolerance and disposition of tetrahydrocannabinol in man," J Pharmacol Exp Ther. Oct. 1980;215(1):35-44, PubMed abstract 6256518.
Iribarne, C. et al., "Involvement of cytochrome P450 3A4 enzyme in the N-demethylation of methadone in human liver microsomes," Chem Res Toxicol. Mar. 1996;9(2):365-73, PubMed abstract 8839037.
Jehanli, A. et al., "Blind trials of an onsite saliva drug test for marijuana and opiates," J Forensic Sci. Sep. 2001;46(5): 1214-20, PubMed 11569567.
Joern, William A., "Surface adsorption of the urinary marijuana carboxy metabolite: the problem and a partial solution," Letter to the Editor, Journal of Analytical Toxicology, vol. 16, Nov./Dec. 1992.
Johansson, E. et al., "Determination of delta 1-tetrahydrocannabinol in human fat biopsies from marihuana users by gas chromatography-mass spectrometry," Biomed Chromatogr. Jan. 1989;3(1):35-8, PubMed abstract 2539872.
Johansson, E. et al., "Prolonged apparent half-life of delta 1-tetrahydrocannabinol in plasma of chronic marijuana users," J Pharm Pharmacol. May 1988;40(5):374-5, PubMed abstract 2899638.
Johannson, E. et al., "Terminal elimination plasma half-life of delta 1-tetrahydrocannabinol (delta 1-THC) in heavy users of marijuana," Eur J Clin Pharmacol. 1989;37(3):273-7, PubMed abstract 2558889.
Johansson, Eva et al., "Urinary excretion half-life of delta1-tetrahydrocannabinol-7-oic acid in heavy marijuana users after smoking," Journal of Analytical Toxicology, vol. 13, Jul./Aug. 1989.
Kadehijian, Leo, "Syva has been a leading developer and manufacturer of drugs-of-abuse tests for more than 30 years," Can-

(56) References Cited

OTHER PUBLICATIONS nabinoid Issues: Passive inhalation, excretion patterns, and retention times, test result interpretation, Siemens Healthcare Diagnostics Inc., 2009.
Karst, Matthias et al., "Analgesic effect of the synthetic cannabinoid CT-3 on chronic neuropathic pain," JAMA, 2003;290(13): 1757-1762.
Kelly, Peggy et al., "Metabolism of tetrahydrocannabinol in frequent and infrequent marijuana users," Journal of Analytical Toxicology, vol. 16, Jul./Aug. 1992.
Kemp, Philip M. et al., "Cannabinoids in Humans. II. The influence of three methods of hydrolysis on the concentration of THC and two metabolites in urine," Journal of Analytical Toxicology, vol. 19, Sep. 1995.
Kemp, Philip M. et al., "Cannabinoids in Humans. I. Analysis of delta9-tetrahydrocannabinol and six metabolites in plasma and urine using GC-MS," Journal of Analytical Toxicology, vol. 19, Sep. 1995.
Kidwell, David A. et al., "Testing for drugs of abuse in saliva and sweat," Journal of Chromatography B: Biomedical Sciences and Applications, vol. 713, Issue 1, Aug. 21, 1998, pp. 111-135, abstract.
Kintz, Pascal et al., "Detection of cannabis in oral fluid (saliva) and forehead wipes (sweat) from impaired drivers," Journal of Analytical Toxicology, vol. 24, Oct. 2000.
Kintz, Pascal et al., "Sweat testing for heroin and metabolites in a heroin maintenance program," Clinical Chemistry 43:5, 736-739 (1997).
Kintz, P. et al., "Testing human hair for cannabis. II. Identification of TCD-COOH by GC-MS-NCI as a unique proof," J Forensic Sci. Jul. 1995;40(4):619-22, PubMed abstract 7595299.
Kovatsi, Leda et al., "Development and validation of a high-performance liquid chromatography method for the evaluation of niflumic acid cross-reactivity of two commercial immunoassays for cannabinoids in urine," Journal of Analytical Toxicology, vol. 34, May 2010.
Kreuz, D.S. et al., "Delta-9-tetrahydrocannabinol: localization in body fat," Science, Jan. 26, 1973; 179(4071):391-3, PubMed abstract 4682965.
Krishna, D.R. et al., "Extrahepatic metabolism of drugs in humans," Clin Pharmacokinet. Feb. 1994;26(2): 144-60, PubMed abstract 8162658.
Lafolie, P. et al., "Importance of creatinine analyses of urine when screening for abused drugs," Clin. Chem. 37/11, 1927-1931 (1991).
Laloup, M. et al., "Correlation of delta9-tetrahydrocannabinol concentrations determined by LC-MS-MS in oral fluid and plasma from impaired drivers and evaluation of the on-site Drager Drug Test," Forensic Sci Int. Sep. 12, 2006;161(2-3): 175-9, PubMed abstract 16842950.
Law, B. et al., "Forensic aspects of the metabolism and excretion of cannabinoids following oral ingestion of cannabis resin," J Pharm Pharmacol. May 1984;36(5):289-94, PubMed abstract 6145762.
Lee, Sooyeun et al., "Estimation of the measurement uncertainty by the bottom-up approach for the determination of methamphetamine and amphetamine in urine," Journal of Analytical Toxicology, vol. 34, May 2010.
Lemberger, L. et al., "11-hydroxy-9-tetrahydrocannabinol: pharmacology, disposition, and metabolism of a major metabolite of marihuana in man," Science. Jul. 7, 1972;177(4043):62-4, PubMed abstract 5041775.
Lemberger, L. et al., "Delta-9-tetrahydrocannabinol: metabolism and disposition in long-term marihuana smokers," Science. Jul. 2, 1971; 173(3991):72-4, PubMed abstract 5087483.
Lemberger, L, et al., "Marihuana: studies on the disposition and metabolism of delta-9-tetrahydrocannabinol in man," Science. Dec. 18, 1970; 170(3964): 1320-2, PubMed abstract 5479011.
Lindgren, J.E. et al., "Clinical effects and plasma levels of delta 9-tetrahydrocannabinol (delta 9-THC) in heavy and light users of cannabis," Psychopharmacology (Berl), 1981;74(3):208-12, PubMed 6267648.

Malfait, A.M. "The nonpsychoactive cannabis constituent cannabidiol is an oral anti-arthritic therapeutic in murine collagen-induced arthritis," Proc Natl Acad Sci USA Aug. 15, 2000;97(17):9561-9566.
Manno, Joseph E. et al., "Temporal indication of marijuana use can be estimated from plasma and urine concentrations of delta9-tetrahydrocannabinol, 11-hydroxy-delta9-tetrahydrocannabinol, and 11-nor-delta9-tetrahydrocannabinol-9-carboxylic acid," Journal of Analytical Toxicology, vol. 25, Oct. 2001.
Manolis, Antony et al., "The detection of delta9-tetrahydrocannabinol in the breath of human subjects," Clinical Biochem. 16,229 (1983).
"Marihuana '84," Proceedings of the Oxford Symposium on Cannabis, D.J. Harvy, editor, IRL Press, Oxford 1984.
Martin, B.R. et al., "3H-delta9-tetrahydrocannabinol distribution in pregnant dogs and their fetuses," Res Commun Chem Pathol Pharmacol. Jul. 1977;17(3):457-70, PubMed abstract 897339.
Mason, A.P. et al., "Cannabis: pharmacology and interpretation of effects," J Forensic Sci. Jul. 1985;30(3):615-31, PubMed abstract 2993473.
Mason, A.P. et al., "Ethanol, marijuana, and other drug use in 600 drivers killed in single-vehicle crashes in North Carolina, 1978-1981," J Forensic Sci. Oct. 1984;29(4):987-1026, PubMed abstract 6502125.
Matsunaga, T. et al., "Metabolism of delta 9-tetrahydrocannabinol by cytochrome P450 isozymes purified from hepatic microsomes of monkeys," Life Sci. 1995;56(23-24):2089-95, PubMed abstract 7776836.
Mattes, R.D. et al., "Bypassing the first-pass effect for the therapeutic use of cannabinoids," Pharmacol Biochem Behav. Mar. 1993;44(3):745-7, PubMed abstract 8383856.
Mattes, R.D. et al., "Cannabinoids and appetite stimulation," Pharmacol Biochem Behav. Sep. 1994;49(1): 187-95, PubMed abstract 7816872.
McBurney, L.J. et al., "GC/MS and EMIT analyses for delta9-tetrahydrocannabinol metabolites in plasma and urine of human subjects," Journal of Analytical Toxicology, vol. 10, Mar./Apr. 1986.
Mechoulam, Raphael et al., "Cannabidiol: an overview of some chemical and pharmacological aspects. Part I: chemical aspects," Chemistry and Physics of Lipids 121 (2002) 35-43.
Mechoulam, Raphael, "Plant cannabinoids: a neglected pharmacological treasure trove," Br J Pharmacol. Dec. 2005; 146(7): 913-915.
Meier, H. et al., "Cannabis poisoning after eating salad," Schweiz Med Wochenschr. Feb. 8, 1997; 127(6):214-8, PubMed abstract 9157527.
Menkes, D.B. et al., "Salivary THC following cannabis smoking correlates with subjective intoxication and heart rate," Psychopharmacology (Berl). 1991;103(2):277-9, PubMed abstract 1851311.
Mijuriya, Tod H., "Cannabis as a substitute for alcohol: a harm-reduction approach," Journal of Cannabis Therapeutics, vol. 4(1) 2004.
Milman, Garry et al., "Simultaneous quantification of cannabinoids and metabolites in oral fluid by two-dimensional gas chromatography mass spectrometry," J Chromatogr A. Feb. 26, 2010; 1217(9): 1513-1521.
Moeller, M.R. et al., "Simultaneous quantitation of delta-9-tetrahydrocannabinol (THC) and 11-nor-9-carboxy-delta-9-tetrahydrocannabinol (THC-COOH) in serum by GC/MS using deuterated internal standards and its application to a smoking study and forensic cases," J Forensic Sci. Jul. 1992;37(4):969-83, PubMed abstract 1324293.
Moldoveanu, Serban C. et al., "Differences in the chemical composition of the particulate phase of inhaled and exhaled cigarette mainstream smoke," Contributions to Tobacco Research 22(4), 290 (2007).
Moore, Christine et al., "Analytical procedure for the determination of the marijuana metabolite 11-nor-delta9-tetrahydrocannabinol-9-carboxylic acid in oral fluid specimens," Journal of Analytical Toxicology, vol. 30, Sep. 2006.
Moore, Christine et al., "Application of two-dimensional gas chromatography with electron capture chemical ionization mass spec-

(56) References Cited

OTHER PUBLICATIONS trometry to the detection of 11-nor-delta9-tetrahydrocannabinol-9-carboxylic acid (THC-COOH) in hair," Journal of Analytical Toxicology, vol. 30, Apr. 2006.
Moore, Christine et al., "Detection of the marijuana metabolite 11-nor-delta9-tetrahydrocannabinol-9-carboxylic acid in oral fluid specimens and its contribution to positive results in screening assays," Journal of Analytical Toxicology, vol. 30, Sep. 2006.
Moore, Christine et al., "The determination of 11-nor-delta9-tetrahydrocannabinol-9-carboxylic acid (THC-COOH) in hair using negative ion gas chromatography-mass spectrometry and high-volume injection," Journal of Analytical Toxicology, vol. 25, Oct. 2001.
Morland, J. et al., "Cannabinoids in blood and urine after passive inhalation of cannabis smoke," J Forensic Sci. Oct. 1985;30(4):997-1002, PubMed abstract 2999292.
Mule, S.J. et al., "Active and realistic passive marijuana exposure tested by three immunoassays and GC/MS in urine," Journal of Analytical Toxicology, vol. 12, May/Jun. 1988.
Mura, P. et al., "Evaluation of six rapid tests for screening of cannabis in sweat, saliva and tears," Acta Clin Belg. 1999;53 Suppl 1:35-8, PubMed abstract 10216980.
Mura, P. et al., "THC can be detected in brain while absent in blood," Letter to the Editor, Journal of Analytical Toxicology, vol. 29, Nov./Dec. 2005.
Nadulski T. et al., "Randomized, double-blind, placebo-controlled study about the effects of cannabidiol (CBD) on the pharmacokinetics of Delat9-tetrahydrocannabinol (THC) after oral application of THC verses standardized cannabis extract," Ther Drug Monit. Dec. 2005;27(6):799-810.
Nadulski T. et al., "Simultaneous and sensitive analysis of THC, 11-OH-THC, THC-COOH, CBD, and CBN by GC-MS in plasma after oral application of small doses of THC and cannabis extract," Journal of Analytical Toxicology, vol. 29, Nov./Dec. 2005.
Nahas, Gabriel G. et al., "Pharmacokinetics of THC in brain and testis, male gametotoxicity and premature apoptosis of spermatozoa," Human Psycopharmacology: Clinical and Experimental, vol. 17, Issue 2, pp. 103-113, Mar. 2002, abstract.
Niedbala, R. Sam et al., "Detection of marijuana use by oral fluid and urine analysis following single-dose administration of smoked and oral marijuana," Journal of Analytical Toxicology, vol. 25, Jul./Aug. 2001.
Niedbala, R. Sam et al., "Passive cannabis smoke exposure and oral fluid testing. II. Two studies of extreme cannabis smoke exposure in a motor vehicle," Journal of Analytical Toxicology, vol. 29, Oct. 2005.
Ohlsson, A. et al., "Plasma delta-9 tetrahydrocannabinol concentrations and clinical effects after oral and intravenous administration and smoking," Clin Pharmacol Ther. Sep. 1980;28(3):409-16, PubMed abstract 6250760.
Ohlsson, Agneta et al., "Single dose kinetics of deuterium labelled delta1-tetrahydrocnnabinol in heavy and light cannabis users," Biological Mass Spectrometry, vol. 9, Issue 1, pp. 6-10, Jan. 1982, abstract.
Owens, S. Michael et al., I Radioimmunoassay of delta-9-tetrahydrocannabinol in blood and plasma with a solid-phase second-antibody separation method, Clin. Chem. 27/4,619-624 (1981).
Peel, H.W. et al., "Detection of drugs in saliva of impaired drivers," J Forensic Sci. Jan. 1984;29(1): 185-9, PubMed abstract 6366113.
Perez-Reyes, M. et al., "The clinical pharmacology and dynamics of marihuana cigarette smoking," J Clin Pharmacol. Aug.-Sep. 1981;21(8-9 Suppl):201S-207S, PubMed abstract 6271825.
Perez-Reyes, M. et al., "Comparison of effects of marihuana cigarettes to three different potencies," Clin Pharmacol Ther. May 1982;31(5):617-24, PubMed abstract 6280918.
Perez-Reyes, M. et al., "Intravenous injection in man of 9-tetrahydrocannabinol and 11-OH-9-tetrahydrocannabinol," Science. Aug. 18, 1972;177(4049):633-5, PubMed abstract 4558903.
Perez-Reyes, Mario, "Marijuana smoking: factors that influence the bioavailability of tetrahydrocannabinol," NIDA Monograph 1990;99:42.
Piao, Wen et al., "Development of azo-based fluorescent probes to detect different levels of hypoxia," Angew. Chem. Int. Ed. 2013, 52, 13028-13032.
Quintela, Oscar et al., "Recovery of drugs of abuse from the immunalysis quantisal™ oral fluid collection device," Journal of Analytical Toxicology, vol. 30, Oct. 2006.
Rahim S.A. et al., "Colorimetric determination of ethanol in the presence of methanol and other species in aqueous solution," Talanta. Nov. 1992;39(11): 1489-91, PubMed abstract 18965558.
Rohrich, J. et al., "Concentrations of delta9-tetrahydrocannabinol and 11-nor-9-carboxytetrahydrocannabinol in blood and urine after passive exposure to cannabis smoke in a coffee shop," Journal of Analytical Toxicology, vol. 34, May 2010.
Russo, E. et al., "A tale of two cannabinoids: the therapeutic rational for combining tetrahydrocannabinol and cannabidiol," Med Hypotheses. 2006;66(2):234-46, PubMed abstract 16209908.
Samyn N. et al., "On-site testing of saliva and sweat with Drugwipe and determination of concentrations of drugs of abuse in saliva, plasma and urine of suspected users," Int J Legal Med. 2000; 113(3): 150-4, PubMed abstract 10876986.
Scheuplein, Robert J., "Mechanism of percutaneous absorption. II. Transient diffusion and the relative importance of various routes of skin penetration," J. Invest. Dermatol 1967;48:79.
Schwartz, Richard H. et al., "Laboratory detection of marijuana use, Experience with a photometric immunoassay to measure urinary cannabinoids," Aj J Dis Child. 1985; 139(11): 1093-1096, abstract.
Schwilke, Eugene W. et al., "Delta9-tetrahydrocannabinol (THC), 11-hydroxy-THC, and 11-nor-9-carboxy-THC plasma pharmacokinetics during and after continuous high-dose oral THC," Clinical Chemistry 55:12 2180-2189 (2009).
Shaw, Leslie M. et al., "Ultrasensitive measurement of delta-9-tetrahydrocannabinol with a high energy dynode detector and electron-capture negative chemical-ionization mass spectrometry," Clin. Chem. 37/12, 2062-2068 (1991).
Skopp, G. et al., "Partition coefficient, blood to plasma ratio, protein binding and short-term stability of 11-nor-Delta(9)-carboxy tetrahydrocannabinol glucuronide," Forensic Sci Int. Mar. 28, 2002; 126(1): 17-23, PubMed abstract 11955826.
Soares, J.R. et al., "Significant developments in radioimmune methods applied to delta9-THC and its 9-substituted metabolites," Analysis of Cannabinoids Research Monograph 42, NIDA 1982.
Stinchcomb, A.L. et al., "Human skin permeation of Delta8-tetrahydrocannabinol, cannabidiol and cannbinol," J Pharm Pharmacol. Mar. 2004;56(3):291-7, PubMed abstract 15025853.
Strano-Rossi, Sabina et al., "Analysis of stimulants in oral fluid and urine by gas chromatography-mass spectrometry II: Pseudophedrine," Journal of Analytical Toxicology, vol. 34, May 2010.
Tan, Chongxiao et al., "Direct detection of delta9-tetrahydrocannabinol in aqueous samples using a homogeneous increasing fluorescence immunoassay (HiFi)," Anal Bioaanal Chem, 2010. 8 pgs.
Teshima, N. et al., "Determination of acetone in breath", Analytica Chimica Acta, 2005, 535, pp. 189-199.
Toennes, Stefan W. et al., "Pharmacokinetic properties of delta9-tetrahydrocannabinol in oral fluid of occasional and chronic users," Journal of Analytical Toxicology, vol. 34, May 2010.
Turner, Carton E. et al., "Constituents of cannabis sativa 1. XVII. A review of the natural constituents," J. Nat. Prod. 1980;43:169.
Valiveti, S. et al., "In vitro/in vivo correlation studies for transdermal delta 8-THC development," J Pharm Sci. May 2004;93(5): 1154-64, PubMed abstract 15067692.
Van der Kooy, F. et al., "Cannabis smoke condensate I: The effect of different preparation methods on tetrahydrocannabinol levels," Inhalation Toxicology, 20:801-804, 2008.
Vinciguerra, V. et al., "Inhalation marijuana as an antiemetic for cancer chemotherapy," NY State J Med. Oct. 1988;88(10):525-7.
Wall, M.E. et al., "The metabolism of delta 9-tetrahydrocannabinol and related cannabinoids in man," J Clin Pharmacol. Aug.-Sep. 1981;21 (8-9 Suppl): 178S-189S, PubMed abstract 6271823.
Wall, M.E. et al., "Metabolism, disposition, and kinetics of delta-9-tetrahydrocannabinol in men and women," Clin Pharmacol Ther. Sep. 1983;34(3):352-63, PubMed abstract 6309462.

(56) References Cited

OTHER PUBLICATIONS

Walsh, J. Michael et al., "An evaluation of rapid point-of-collection oral fluid drug-testing devices," Journal of Analytical Toxicology, vol. 27, Oct. 2003.
Watanabe, K. et al., "Brain microsomal oxidation of delta 8- and delta 9-tetrahydrocannabinol," Biochem Biophys Res Commun. Nov. 30, 1988;157(1):75-80, PubMed abstract 2848522.
Widman, M. et al., "Metabolism of delta 1-tetrahydrocannabinol by the isolated perfused dog lung. Comparison with in vitro liver matabolism." J Phar Pharmacol. Nov. 1975;27(11):842-8, PubMed abstract 1493.
Williams, P.L. et al., "Identification in human urine of delta 9-tetrahydrocannabinol-11-oic acid glucuronide: a tetrahydrocannabinol metabolite," J Pharm Pharmacol. Jul. 1980;32(7):445-8, PubMed abstract 6105177.
Wingert, William E., "Lowering cutoffs for initial and confirmation testing for cocaine and marijuana: large-scale study of effects on the rates of drug-positive results," Clinical Chemistry 43:1 100-103 (1997).
Zajicek, J. et al., "Cannabinoids for treatment of spasticity and other symptoms related to multiple sclerosis (CAMS study): multi centre randomised placebo-controlled trial," Lancet. Nov. 8, 2003;362(9395): 1517-26, abstract.
Zias, Joe et al., "Early medical use of cannabis," Nature; May 20, 1993; 363,6426; Research Library Core p. 215.
Zuardi, A.W. et al., "Action of cannabidiol on the anxiety and other effects produced by delta 9-THC in normal subjects," Psychopharmacology (Berl). 1982;76(3):245-50, PubMed abstract 6285406.
U.S. Appl. No. 15/650,537, filed Jul. 14, 2017, Gordon et al.
U.S. Appl. No. 15/875,195, filed Jan. 19, 2018, Lynn et al.
U.S. Appl. No. 16/248,656, filed Jan. 15, 2019, Lynn et al.
U.S. Appl. No. 15/981,797, filed May 16, 2018, Lynn et al.
U.S. Appl. No. 15/875,195, Office Action dated Apr. 19, 2018.
U.S. Appl. No. 15/875,195, Notice of Allowance dated Jan. 11, 2019.
U.S. Appl. No. 15/650,537, Office Action dated Mar. 29, 2019.
U.S. Appl. No. 15/650,537, Notice of Allowance dated Apr. 24, 2019.
U.S. Appl. No. 15/650,537, Notice of Allowance dated Jun. 14, 2019.
U.S. Appl. No. 15/943,123, Office Action dated Mar. 6, 2020.
U.S. Appl. No. 15/943,123, Office Action dated Jun. 29, 2020.
International Search Report dated Jan. 23, 2020, for International Patent Application No. PCT/US2019/060342, 9 pages.
Written Opinion of the Searching Authority dated Jan. 23, 2020, for International Patent Application No. PCT/US2019/060342, 9 pages.
International Search Report dated Apr. 6, 2020, for International Patent Application No. PCT/US2020/13553, 2 pages.
Written Opinion of the Searching Authority dated Apr. 6, 2020, for International Patent Application No. PCT/US2020/13553, 7 pages.
Andrews, Travis M., "Breathalyzers of the Future Today," The Atlantic, Jun. 27, 2013. Downloaded from the Internet on Feb. 4, 2019, http://www.theatlantic.com/health/archive/2013/06/breathalyzers-of-the-future-today/277249/.
Dunk, et al., "Development of a Portable Marijuana Breathalyzer", (Mar. 2018), URL=http://https://houndlabs.com/wp-content/uploads/2018/03/Hound-TRT-Pittcon-Poster.pdf.
"N.S. woman who tested positive for pot when she wasn't high to challenge roadside testing laws," CBC Radio, posted Apr. 3, 2019. 6 pages.
Sarafian, Theodor et al., "Inhaled marijuana smoke disrupts mitochondrial energetics in pulmonary epithelial cells in vivo," Am J Physiol Lung Cell Mol Physiol, 2006, 290. L1202-L1209. (Year:2006).
Aliberti, S, et al., "Serum and exhaled breath condensate inflammatory cytokines in community-acquired pneumonia: a prospective cohort study", Pneumonia (Nathan), (Jun. 23, 2016), 8:8. doi: 10.1186/s41479-016-0009-7. eCollection 2016.

Bajaj, P., and F.T. Ishmael, "Exhaled breath condensates as a source for biomarkers for characterization of inflammatory lung diseases", Journal of Analytical Sciences, Methods and Instrumentation, (Mar. 20, 2013), 3(01):17.
Beck, O., et al., "Detection of drugs of abuse in exhaled breath using a device for rapid collection: comparison with plasma, urine and self-reporting in 47 drug users" Journal of breath research, (Apr. 25, 2013), 7(2):026006.
Carpenter, C.T., Price PV, Christman BW. Exhaled breath condensate isoprostanes are elevated in patients with acute lung injury or ARDS. Chest. Dec. 1, 1998;114(6):1653-9.
Emelyanov, A., et al., "Elevated concentrations of exhaled hydrogen peroxide in asthmatic patients", Chest, (Oct. 1, 2001), 120(4): 1136-9.
Grob, N.M., et al., "Biomarkers in exhaled breath condensate: a review of collection, processing and analysis", Journal of breath research, (Sep. 8, 2008), 2(3):037004.
Hasan, R.A., et al., "A4 and 8-isoprostane in the exhaled breath condensate of children hospitalized for status asthmaticus", Pediatric critical care medicine: a journal of the Society of Critical Care Medicine and the World Federation of Pediatric Intensive and Critical Care Societies, (Mar. 2012), 13(2):141.
Kodavanti, U.P. "Respiratory toxicity biomarkers", In Biomarkers in Toxicology, (Jan. 1, 2014) (pp. 217-239). Academic Press.
Krenke, K. et al., "Inflammatory cytokines in exhaled breath condensate in children with inflammatory bowel diseases", Pediatric pulmonology, (Dec. 2014), 49(12): 1190-5.
Oguma, T., et al., "Clinical contributions of exhaled volatile organic compounds in the diagnosis of lung cancer", PloS one, (Apr. 6, 2017), 12(4):e0174802.
Saalberg, Yannick and Marcus Wolff, "VOC breath biomarkers in lung cancer", Clinica Chimica Acta, (Aug. 1, 2016), 459:5-9.
Samitas, K., et al., "Exhaled cysteinyl-leukotrienes and 8-isoprostane in patients with asthma and their relation to clinical severity", Respiratory medicine, (May 1, 2009), 103(5):750-6.
Wan, G.H., et al., "Cysteinyl leukotriene levels correlate with 8-isoprostane levels in exhaled breath condensates of atopic and healthy children", Pediatric research (Nov. 2013), 74(5):584.
Zanconato, S., et al., "Leukotrienes and 8-isoprostane in exhaled breath condensate of children with stable and unstable asthma", Journal of Allergy and Clinical Immunology, (Feb. 1, 2004), 113(2):257-63.
Zhou, J., "Review of recent developments in determining volatile organic compounds in exhaled breath as biomarkers for lung cancer diagnosis", Analytica chimica acta, (Dec. 15, 2017), 996:1-9.
"Drug detection, health monitoring etc.", SensAbues AB—Innovation, downloaded on Mar. 25, 2019 from http://sensabues.com/innovation.
"Exhaled breath biological sample matrix. EB", SensAbues AB—Product, downloaded on Mar. 25, 2019 from http://sensabues.com/product.
"Exhaled breath sampling company", SensAbues AB—About, downloaded on Mar. 25, 2019 from http://sensabues.com/about.
"FAIMS Breathalyzer Device", downloaded on Mar. 25, 2019 from https://algernonpharmaceuticals.com/faims-breathalyzer-device/.
"Low cost, non-invasive and non-intrusi", SensAbues AB—Benefits, downloaded on Mar. 25, 2019 from http://sensabues.com/benefits.
"Owlstone—About", downloaded on Mar. 25, 2019 from https://www.owlstonemedical.com/about/.
"Owlstone—EVOC Probes", downloaded on Mar. 25, 2019 from https://www.owlstonemedical.com/science-technology/evoc-probes/.
"Owlstone—FAIMS technology", downloaded on Mar. 25, 2019 from https://www.owlstonemedical.com/science-technology/faims-technology/.
"Owlstone—Research case studies", downloaded on Mar. 25, 2019 from https://www.owlstonemedical.com/science-technology/research-case-studies/.
"Owlstone Medical—Active Clinical Pipeline", downloaded on Mar. 25, 2019 from https://www.owlstonemedical.com/clinical-pipeline/.

(56) References Cited

OTHER PUBLICATIONS

"Owlstone Medical—The Home of Breath Biopsy: A Breathalyzer for Disease", downloaded on Mar. 25, 2019 from https://www.owlstonemedical.com/#.
"Owlstone Medical—The Home of Breath Biopsy: Breath Biopsy—VOC Biomarkers", downloaded on Mar. 25, 2019 from https://www.owlstonemedical.com/#.
"Owlstone Medical—Products", downloaded on Mar. 25, 2019 from https://www.owlstonemedical.com/products/.
"Pexa—About PExA", downloaded on Mar. 25, 2019 from http://pexa.se/en/about-pexa/.
"Pexa—Analysis", downloaded on Mar. 25, 2019 from http://pexa.se/en/product-services/analysis/.
"Pexa—Business Concept & Vision", downloaded on Mar. 25, 2019 from http://pexa.se/en/about-pexa/business-concept-vision/.
"Pexa—History", downloaded on Mar. 25, 2019 from http://pexa.se/en/about-pexa/history/.
"Pexa—How PExA works", downloaded on Mar. 25, 2019 from http://pexa.se/en/product-services/how-pexa-works/.
"Pexa—The importance of early diagnosis", downloaded on Mar. 25, 2019 from http://pexa.se/en/respiratory-research/the-importance-of-early-diagnosis/.
"Pexa—Particles in Exhaled Air", downloaded on Mar. 25, 2019 from http://pexa.se/en/.
"Pexa—PExA 2.0", downloaded on Mar. 25, 2019 from http://pexa.se/en/product-services/pexa-2-0/.
"Pexa—Product & Services", downloaded on Mar. 25, 2019 from http://pexa.se/en/product-services/.
"Pexa—Product-Sheet", Sep. 2016.
"Pexa—R&D and publications", downloaded on Mar. 25, 2019 from http://pexa.se/en/product-services/research-development/.
"Pexa—Research areas", downloaded on Mar. 25, 2019 from http://pexa.se/en/respiratory-research/research-areas/.
"Pexa—Respiratory Research Needs", downloaded on Mar. 25, 2019 from http://pexa.se/en/respiratory-research/.
"Pexa—The search for new biomarkers", downloaded on Mar. 25, 2019 from http://pexa.se/en/respiratory-research/the-search-for-new-biomarkers/.
"SensAbues AB—Next generation drug detection and health monitoring", SensAbues AB—Home, downloaded on Mar. 25, 2019 from http://sensabues.com/home.
"Volatile Organic Compounds (VOC) as non-invasive biomarkers for a range of diseases", downloaded on Mar. 25, 2019 from https://www.owlstonemedical.com/science-technology/voc-biomarkers/.
U.S. Appl. No. 16/248,656, filed Sep. 7, 2019, Michael Scott Lynn et al.
U.S. Appl. No. 16/790,457, filed Feb. 13, 2020, Michael Scott Lynn et al.
U.S. Appl. No. 15/943,123, filed Apr. 2, 2018, Michael Scott Lynn et al.
U.S. Appl. No. 16/124,181, filed Sep. 6, 2018, Michael Scott Lynn et al.
U.S. Appl. No. 16/823,113, filed Mar. 18, 2020, Michael Scott Lynn et al.
U.S. Appl. No. 16/563,839, Office Action dated Apr. 15, 2020.
U.S. Appl. No. 16/248,656, Office Action dated Mar. 5, 2020.
U.S. Appl. No. 16/248,656, Office Action dated Jul. 13, 2020.
U.S. Appl. No. 15/958,616, Notice of Allowance dated Jan. 2, 2020.
U.S. Appl. No. 15/943,123, Notice of Allowance dated Nov. 12, 2020.
U.S. Appl. No. 15/943,123, Notice of Allowance dated Dec. 22, 2020.
International Preliminary Report on Patentability dated May 11, 2021, for International Patent Application No. PCT/US2019/060342, 9 pages.
Zhu, H.J., Wang JS, Markowitz JS, Donovan JL, Gibson BB, Gefroh HA, DeVane CL., "Characterization of P-glycoprotein inhibition by major cannabinoids from marijuana", Journal of Pharmacology and Experimental Therapeutics. May 1, 2006;317(2):850-7.
Ullman EF, Kirakossian H, Switchenko AC, Ishkanian J, Ericson M, Wartchow CA, Pirio M, Pease J, Irvin BR, Singh S, Singh R. Luminescent oxygen channeling assay (LOCI): sensitive, broadly applicable homogeneous immunoassay method. Clinical chemistry. Sep. 1, 1996;42(9):1518-26.
Beaudet L, Rodriguez-Suarez R, Venne MH, Caron M, Bédard J, Brechler V, Parent S, Bielefeld-Sévigny M. "AlphaLISA immunoassays: the no-wash alternative to ELISAs for research and drug discovery", Nature Methods, (Dec. 2008), 5(12):an8-9.
Grob NM, Aytekin M, Dweik RA. "Biomarkers in exhaled breath condensate: a review of collection, processing and analysis", Journal of breath research, (Sep. 8, 2008), 2(3):037004.
Prodromidis, M.I., "Impedimetric immunosensors—A review", Electrochimica Acta, (May 30, 2010), 55(14):4227-33.
D'Ambrosio, M. et al., "Point-of-care quantification of blood-borne filarial parasites with a mobile phone microscope", Science Translational Medicine (May 6, 2015), vol. 7, Issue 286, p. 286re4. 10 pages.
Switz, N. A., et al., "Low-Cost Mobile Phone Microscopy with a Reversed Mobile Phone Camera Lens", PloS one, (May 22, 2014), 9(5):e95330. 7 pages.
U.S. Appl. No. 16/563,839, filed Sep. 7, 2019, Michael Scott Lynn et al.
U.S. Appl. No. 16/949,065, filed Oct. 12, 2020, Gordon et al.
U.S. Appl. No. 16/949,066, filed Oct. 12, 2020, Michael Scott Lynn et al.
U.S. Appl. No. 17/249,817, filed Mar. 15, 2021, Michael Scott Lynn et al.
U.S. Appl. No. 17/302,476, filed May 4, 2021, Michael Scott Lynn et al.
U.S. Appl. No. 16/729,116, filed Dec. 27, 2019, Michael Scott Lynn et al.
U.S. Appl. No. 16/776,501, filed Jan. 29, 2020, Michael Scott Lynn et al.
U.S. Appl. No. 16/655,182, filed Oct. 16, 2019, Michael Scott Lynn et al.
U.S. Appl. No. 17/247,926, filed Dec. 30, 2020, Michael Scott Lynn et al.
U.S. Appl. No. 17/249,096, filed Feb. 19, 2021, Jeffrey Adam Stoll.
U.S. Appl. No. 17/301,559, filed Apr. 7, 2021, Michael Scott Lynn et al.
U.S. Appl. No. 17/301,507, filed Apr. 5, 2021, D' Ambrosio et al.
U.S. Appl. No. 17/301,974, filed Apr. 20, 2021, Friedman et al.
U.S. Appl. No. 17/302,801, filed May 12, 2021, Stoll et al.
U.S. Appl. No. 15/981,797, Office Action dated Oct. 16, 2020.
U.S. Appl. No. 15/981,797, Notice of Allowance dated Feb. 9, 2021.
U.S. Appl. No. 16/655,182, Office Action dated May 7, 2021.

\* cited by examiner

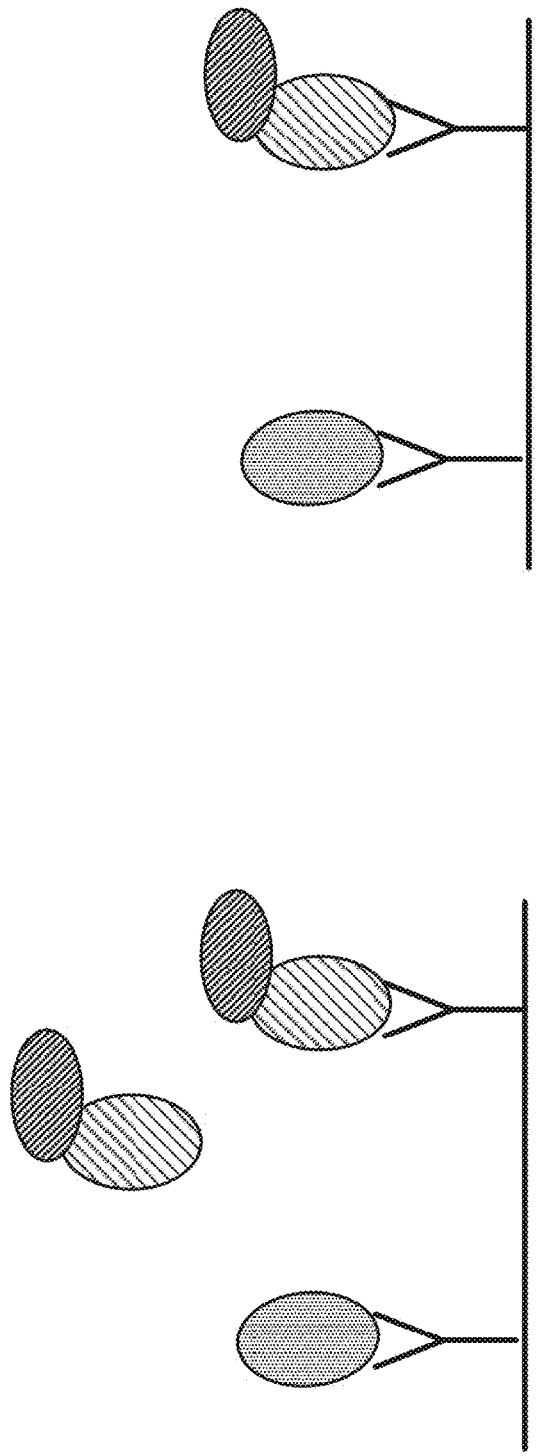
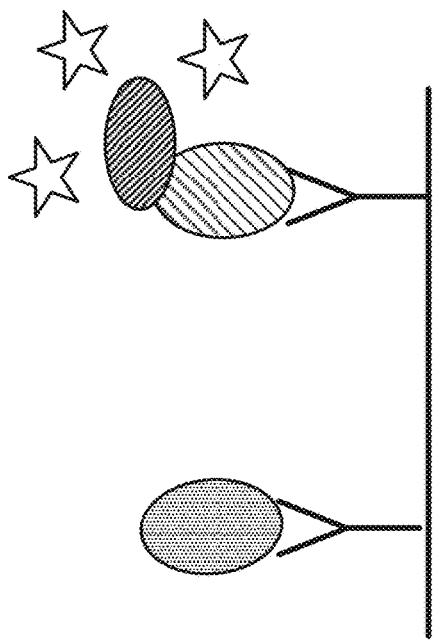
FIG. 4A
FIG. 4B
FIG. 4C

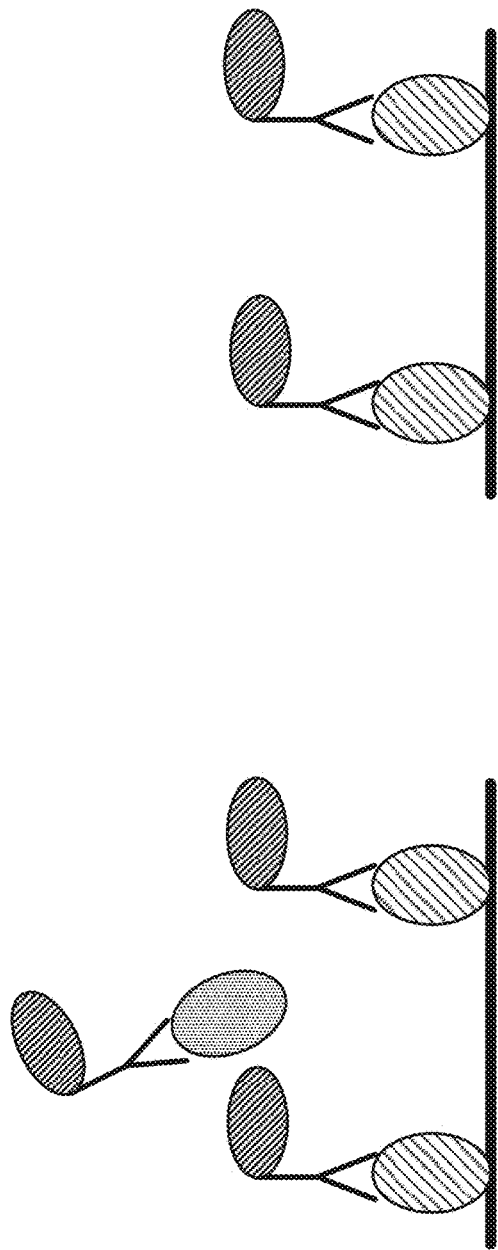
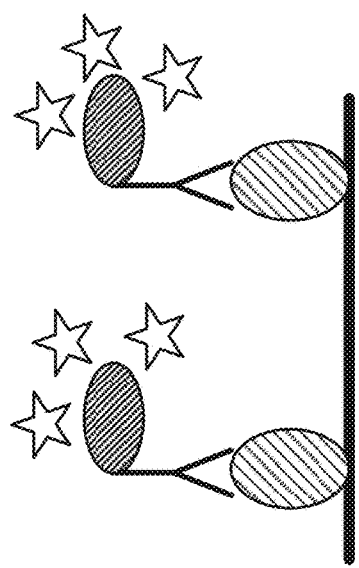
FIG. 5A
FIG. 5B
FIG. 5C

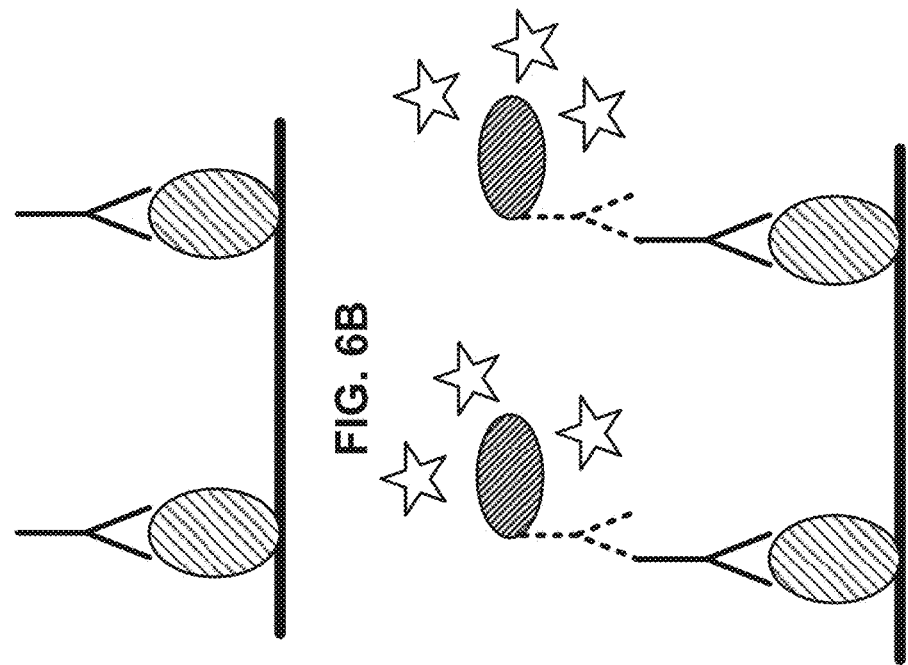
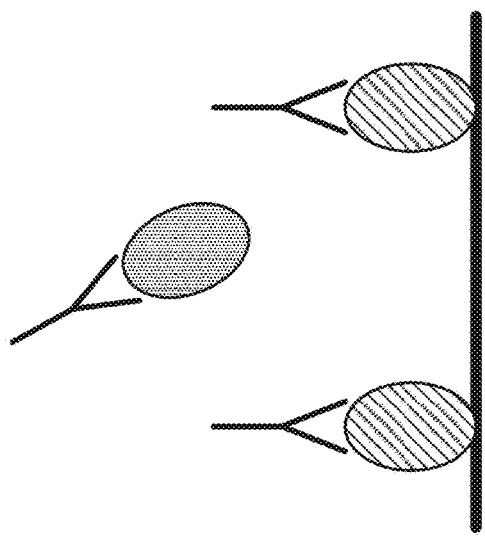
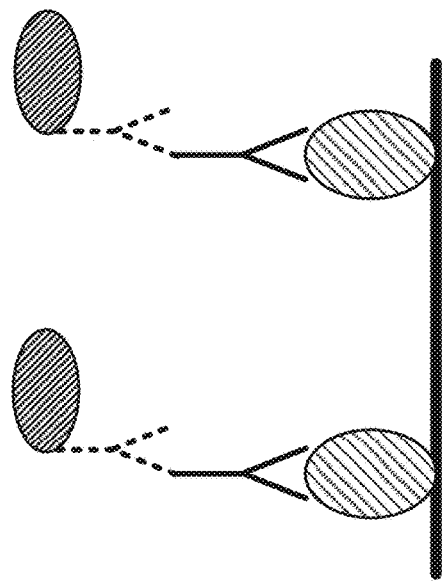

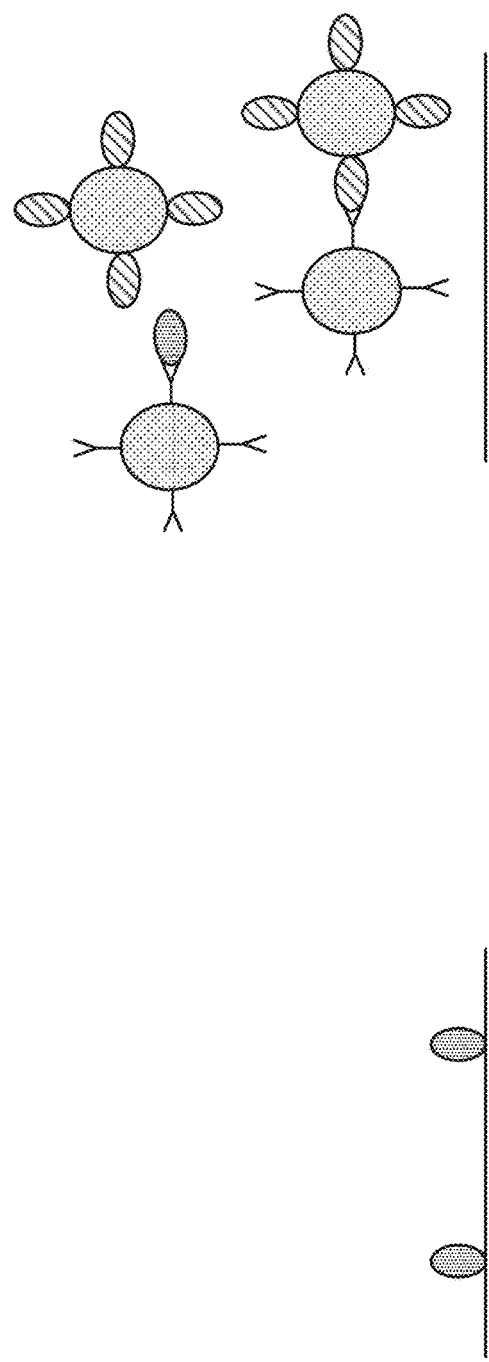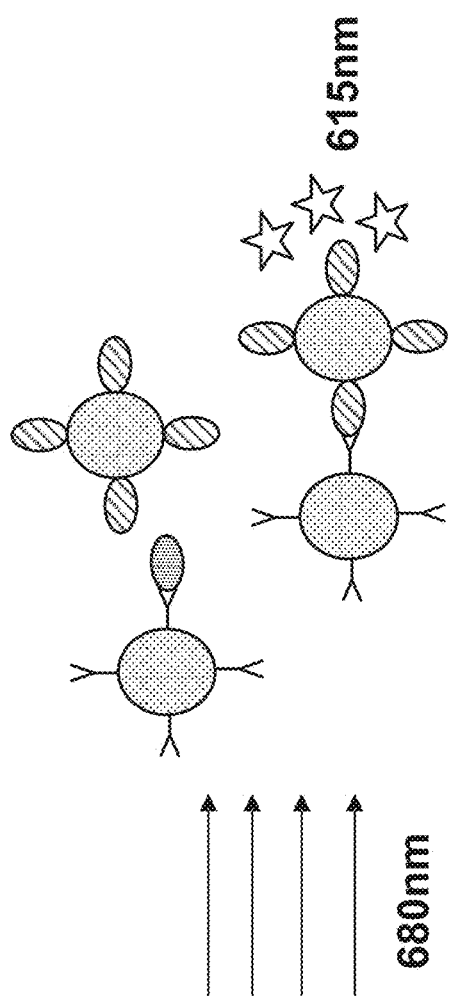

Transparent / translucent

ANALYTE DETECTION FROM BREATH SAMPLES

CROSS-REFERENCE TO RELATED APPLICATIONS

This application claims benefit of priority under 35 U.S.C. § 119(e) to U.S. Provisional Application No. 62/557,056, filed Sep. 11, 2017, titled "IMMUNOASSAY METHODS FOR DETECTING THC IN BREATH"; U.S. Provisional Application No. 62/557,060, filed Sep. 11, 2017, titled "DIAGNOSTIC AND ANALYTICAL ASSAY PERFORMANCE FOR THC IMMUNOASSAY"; U.S. Provisional Application No. 62/616,380, filed Jan. 11, 2018, which is titled "METHOD AND DEVICE FOR MEASURING THC LEVEL FROM BREATH SAMPLE"; and U.S. Provisional Application No. 62/646,798, filed Mar. 22, 2018, each of which is hereby incorporated by reference herein in its entirety for at least their disclosure relating to implementation of THC detection methods and apparatuses that are suitable for implementation of the disclosed methods and devices.

This application also incorporates by reference the following applications for their disclosure relating to implementation of THC detection methods and apparatus that are suitable for implementation of the disclosed method and devices: U.S. Provisional Patent Application No. 62/337,286, filed May 16, 2016, and titled "BREATH COLLECTOR MODULE," U.S. Provisional Patent Application No. 62/351,858, filed Jun. 17, 2016, and titled "COMPOSITIONS AND METHODS FOR DETECTION OF TARGET CONSTITUENT IN EXHALED BREATH," U.S. Provisional Patent Application No. 62/351,821, filed Jun. 17, 2016, and titled "SYSTEM AND METHOD FOR TARGET SUBSTANCE IDENTIFICATION," U.S. patent application Ser. No. 15/217,151, filed Jul. 22, 2016, and titled "COMPOSITIONS AND METHODS FOR DETECTION OF TARGET CONSTITUENT IN EXHALED BREATH," U.S. Provisional Patent Application No. 62/351,858, filed Jun. 17, 2016, U.S. patent application Ser. No. 14/997,405, titled "METHOD, DEVICE AND SYSTEM FOR TARGET SUBSTANCE DETECTION" and filed Jan. 15, 2016, U.S. Provisional Application Nos. 62/104,813, filed Jan. 18, 2015, and 62/107,331, filed Jan. 23, 2015, both of which are titled "METHOD, DEVICE AND SYSTEM FOR TARGET SUBSTANCE DETECTION," U.S. Provisional Application No. 62/277,854, filed Jan. 12, 2016, and titled "PORTABLE, HAND-HELD INSTRUMENT FOR DETECTION AND QUANTIFICATION OF CANNABINOIDS AND ALCOHOL IN EXHALED HUMAN BREATH," and U.S. Provisional Application Nos. 62/508,864, filed May 19, 2017, and 62/514,618, filed Jun. 2, 2017, both of which are titled "SYSTEM AND METHOD FOR TARGET SUBSTANCE IDENTIFICATION."

BACKGROUND

With legalization of marijuana expanding and the risk of marijuana-associated impaired driving increasing, it is anticipated by the present inventors that there will be an increased need for portable and accurate measurement systems, methods and devices for quantifying levels of cannabinoid compounds, such as tetrahydrocannabinol (THC), that are present in a person's breath, e.g., such as during a traffic stop for suspected driving-under-the-influence. THC detection poses significant challenges since the amounts of THC that may be present in an exhaled breath are quite minute—much more so than is the case with alcohol.

Furthermore, THC detection in human breath is generally the only reliable way to determine if a suspected marijuana user is under the influence. Unlike with alcohol, which the body can purge in relatively short order, e.g., less than a day, THC compounds may be present in a person's body long after they are no longer under the influence of the THC. Thus, detection of THC via blood or urine sample may result in false positives in terms of being under the influence of marijuana. Breath-testing for THC in breath at the roadside, alone or in combination with alcohol, would be convenient, non-invasive, and leverages the wide acceptance of administering a breath test at the roadside, as is commonly employed for alcohol.

SUMMARY

Details of one or more implementations of the subject matter described in this specification are set forth in the accompanying drawings and the description below. Other features, aspects, and advantages will become apparent from the description, the drawings, and the claims.

Methods, systems and apparatus for evaluating tetrahydrocannabinol (THC) level from a breath sample are disclosed. In various embodiments, the disclosed methods include immunoassay-based detection systems and methods. Among the potential benefits of such methods and systems are enhanced sensitivity and device scalability. The disclosed methods and systems may be implemented in variety of ways as contemplated by this disclosure. Among the features of the disclosure are systems and methods that may be implemented in devices that provide for convenient and reliable roadside detection and determination of THC recent use that may be correlated with impairment. The systems, methods and contemplated devices may also be adaptable to combining testing for THC and alcohol (ethanol) impairment, and/or to the detection and evaluation of other airborne substances, including controlled substances, and breath-borne indicators of various disease states.

According to various embodiments, a method in accordance with this disclosure involves determining an amount of THC captured from a breath sample obtained from a subject, comparing the determined amount of THC captured from the breath sample to a threshold level for THC in breath, and indicating whether or not the determined amount of THC captured from the breath sample exceeds the threshold. A reliably detectable picogram-level threshold may be correlated with a maximum baseline level of THC in breath associated with consumption of THC outside a window of THC-associated impairment and/or an average amount of THC in breath between 2 and 3 hours after inhalation for a range of users. The threshold may represent a baseline mean level of residual THC in breath associated with consumption of THC outside a window of THC-associated impairment across a broad demographic, for example from inhalation to between 2 and 3 hours after inhalation. An indication that the amount of THC captured from a breath sample exceeds the threshold may then be considered a positive test result for recent inhalation of THC that is independent of the frequency of the test subject's THC use. Such a method, then, may be adapted for breath-testing for THC, alone or in combination with alcohol, at the roadside.

THC, however, is much less prevalent in breath compared to alcohol, and is measured in the parts per trillion (picograms, pg) range in breath. According to various embodiments, the threshold referenced in the comparison may be less than 10 picogram/liter (pg/L) of breath, or from 2 to 5 pg/L of breath, or from 2 to 3 pg/L of breath, for example, about 2.4 pg/L of breath. The threshold may vary depending upon the capture efficiency of the device or system with which the method is conducted.

In various embodiments, the method may include obtaining the breath sample from the subject in manner suitable to conduct measurements in the picogram range in a roadside sobriety testing context, in particular using a device having a handheld form factor for obtaining the breath sample and conducting an analysis on site in a prescribed period of time. Such a method may involve drawing a portion of the breath sample exhaled by the subject into a reaction channel in a test cartridge with negative pressure. So that sufficient THC can be captured from a breath sample for use in a roadside sobriety testing context, the reaction channel may be configured to have a particular hydraulic diameter and length and/or shape.

In various embodiments, in order achieve picogram sensitivity the determining aspect of the method may involve an immunoassay. Suitable immunoassays may include surface-based antibody-down immunoassays, surface-based antigen-down immunoassays, noncompetitive immunoassays, heterogeneous competitive immunoassays, and homogeneous competitive immunoassays.

In various embodiments, in order to meet the evidentiary standards associated with roadside sobriety tests, an equal portion of the breath sample as drawn into the reaction channel may be drawn into an evidence channel on the test cartridge.

In various embodiments, the test cartridge comprises a microfluidic device.

In various embodiments, data corresponding to one or more of the determining the amount of THC captured from the breath sample obtained from the subject, the comparing the determined amount of THC from the breath sample to a threshold level for THC in breath, and the indicating whether or not the determined amount of THC captured from the breath sample exceeds the threshold, may be wirelessly transmitted to a remote location.

In various embodiments, both THC and ethanol are measured from the same breath sample.

The methods, systems and apparatus described herein may also be adaptable as a platform for detection and evaluation of other airborne/breath-borne substances, including controlled substances, and breath-borne indicators of various disease states. In this regard, this disclosure also relates to a method for evaluating a substance, more generally, in air, such as a human breath, the method involving determining an amount of a substance captured from a breath sample obtained from a subject, comparing the determined amount of the substance from the breath sample to a threshold level for the substance in breath, and indicating whether or not the determined amount of the substance captured from the breath sample exceeds the threshold. The substance may be associated with a human disease condition, such as stomach cancer, lung cancer, heart failure, kidney failure or diabetes, for example, and the threshold may, for example, be correlated with a baseline maximum level of the substance in human breath for a subject not suffering from the disease condition, and the substance is associated with a human disease condition, such as stomach cancer, lung cancer, heart failure, kidney failure or diabetes.

This disclosure also relates to systems and apparatus for measuring tetrahydrocannabinol (THC) level from a breath sample in accordance with the methods herein described.

Details of one or more implementations of the subject matter described in this specification are set forth in the accompanying drawings and the description below. Other features, aspects, and advantages will become apparent from the description, the drawings, and the claims.

BRIEF DESCRIPTION OF THE DRAWINGS

The various implementations disclosed herein are illustrated by way of example, and not by way of limitation, in the figures of the accompanying drawings, in which like reference numerals refer to similar elements.

FIGS. 4A-C depict a surface-based competitive antibody-down, chemoluminescence immunoassay.

FIGS. 5A-C depict a surface-based antigen-down, heterogeneous, competitive single-antibody immunoassay.

FIGS. 6A-D depict a surface-based antigen-down, heterogeneous, competitive two-antibody immunoassay.

FIGS. 7A-C depict a homogeneous competitive immunoassay.

FIGS. 8 through 69, aside from the schematic Figures, are drawn to-scale within each Figure, although not necessarily to the same scale from Figure to Figure.

DETAILED DESCRIPTION

Importantly, the concepts discussed herein are not limited to any single aspect or implementation discussed herein, nor to any combinations and/or permutations of such aspects and/or implementations. Moreover, each of the aspects of the present invention, and/or implementations thereof, may be employed alone or in combination with one or more of the other aspects and/or implementations thereof. For the sake of brevity, many of those permutations and combinations will not be discussed and/or illustrated separately herein.

Methods, systems and apparatus for measuring tetrahydrocannabinol (THC) level from a breath sample are disclosed. In various embodiments, the disclosed methods include immunoassay-based detection systems and methods. Among the potential benefits of such methods and systems are enhanced sensitivity and device scalability. The disclosed methods and systems may be implemented in variety of ways as contemplated by this disclosure. Among the features of the disclosure are systems and methods that may be implemented in devices that provide for convenient and reliable roadside detection and determination of THC recent use that may be correlated with impairment. The systems, methods and contemplated devices may also be adaptable to combining testing for THC and alcohol (ethanol) impairment, and/or to the detection of other airborne substances, including controlled substances, and breath-borne indicators of various disease states.

In Marijuana-Impaired Driving: A Report to Congress dated July 2017, the National Highway Traffic Safety Administration (NHTSA) found that impairment is observed for two to three hours after smoking marijuana. Data collected and processed by the inventors has shown that a reliably detectable picogram-level threshold may be correlated with a maximum baseline level of THC in breath for chronic or frequent THC smokers and/or an average amount of THC in breath between 2 and 3 hours after inhalation for a range of users. More generally, it appears that the threshold may represent a baseline mean level of residual THC in breath associated with consumption of THC outside a window of THC-associated impairment across a broad demographic, for example from inhalation to between 2 and 3 hours after inhalation. An indication that the amount of THC captured from a breath sample exceeds the threshold may then be considered a positive test result for recent inhalation of THC that is therefore independent of the frequency of the test subject's THC use. Such a method, then, may be adapted for breath-testing for THC at the roadside.

Figure 1:
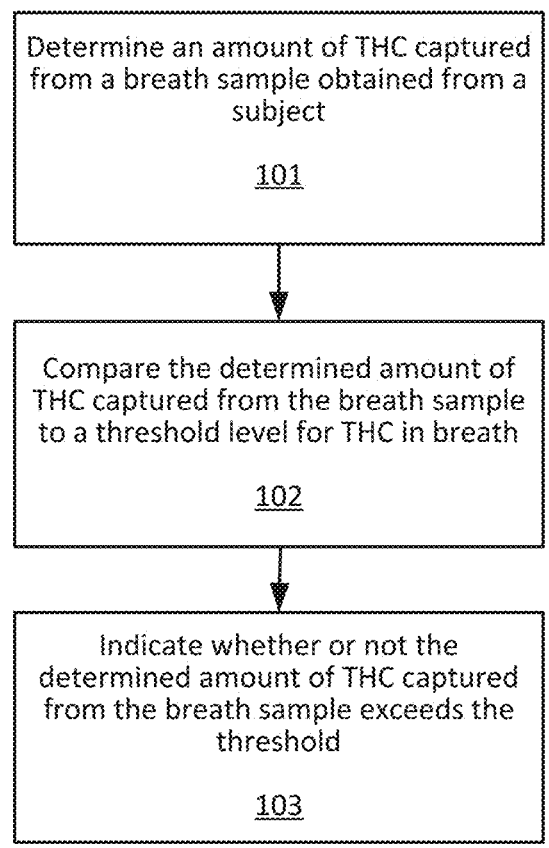
FIG. 1 depicts a process flow chart for method in accordance with the present disclosure.

Referring to FIG. 1, a general flow chart for a method in accordance with the present disclosure is depicted. According to various embodiments, the method involves determining an amount of THC captured from a breath sample obtained from a subject (101), comparing the determined amount of captured THC from the breath sample to a threshold level of THC in breath (102), and indicating whether or not the determined amount of captured THC from the breath sample exceeds the threshold (103).

Figure 2:
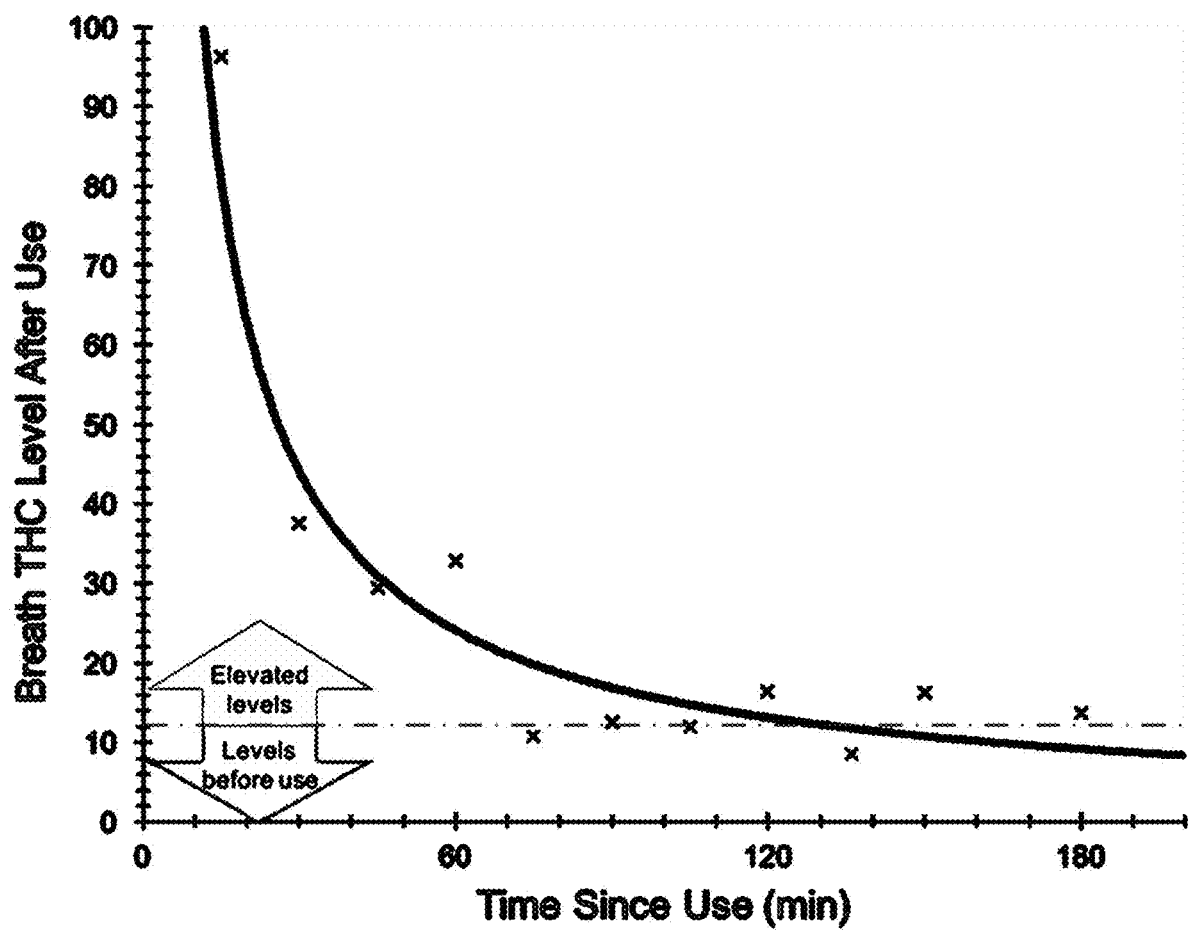
FIG. 2 depicts a plot showing breath THC level vs. time since use.

FIG. 2 depicts a plot showing breath THC level in picograms (pg) per breath (5 L) vs. time in minutes (min) since use in chronic or frequent THC smokers. From the plot it can be seen that THC level in breath drops substantially in the first hour, and after 2 hours it drops below the maximum baseline threshold for chronic users. Testing has determined a maximum baseline THC level in breath for chronic users to be in the picogram per liter of breath range. Based on data obtained through testing, it appears that the threshold may represent a baseline mean level of residual THC in breath associated with consumption of THC across a broad demographic, regardless of use frequency, outside a window from inhalation to between 2 and 3 hours after inhalation, which has been associated with THC impairment. The threshold referenced in the comparison of the disclosed method may be less than 10 picogram/liter (pg/L) of breath, or from 2 to 5 pg/L of breath, or from 2 to 3 pg/L of breath, for example, about 2.4 pg/L of breath. The maximum baseline 12 pg/5 L (2.4 pg/L) breath is superimposed on the plot. The threshold may vary depending upon the capture efficiency of the device or system with which the method is conducted, and can be tuned in practice.

It should also be understood that breath-testing for THC at the roadside may be combined with breath-testing for alcohol where another portion of the breath sample is tested for blood alcohol content (BAC) according to any suitable BAC analysis, such as are well-known in the art, as further discussed below.

In various embodiments, the method may include obtaining and processing the breath sample from the subject in manner suitable to conduct measurements in the picogram range in a roadside sobriety testing context, in particular using a device having a handheld form factor for obtaining the breath sample in a prescribed period of time and conducting an analysis on-site. Such a method may involve drawing a portion of the breath sample exhaled by the subject into a reaction channel in a test cartridge with negative pressure. So that sufficient THC can be captured from a breath sample for use in a roadside sobriety testing context, the reaction channel may be configured to have a particular hydraulic diameter and length and/or shape for to enhance or optimize capture efficiency.

One way to configure the reaction channel is according to the following parameters: For a minimum channel volume of 15 µL, the hydraulic diameter (d) may range from 0.1-1 mm, and the channel length may range from 15 $\mu L/(d^2)$ to 45 $\mu L/(d^2)$ (assuming d in mm). In specific implementations, the reaction channel may have a hydraulic diameter of less than 1 mm and a length of at least 15 mm, and at least 0.5 L of the breath sample may be flowed through the reaction channel in no more than 90 s. In some embodiments, the reaction channel may have a hydraulic diameter of less than 0.8 mm and a length of at least 40 mm, for example a hydraulic diameter of about 0.7 mm and a length of about 57 mm, and at least 0.7 L of the breath sample may be flowed through the reaction channel in about 60 s.

The preceding discussion of channel configuration relates to straight channels. But it should also be understood that the shape of a channel may also be manipulated to enhance capture efficiency. Other channel geometries, including hydraulic diameters, lengths and shapes may be desired depending on a particular capture target(s). The size, shape and form of the molecule or particle, etc. to be captured is generally a significant factor in configuring the channel to enhance or optimize capture efficiency. In general, larger targets would be better captured in channels that are not straight, such as zigzag, curved, spiral, etc.-shaped channels. It should be understood that the channel geometry can be optimized for capture efficiency, and can change depending upon the capture target(s).

Also a device can have multiple channels with same or different geometry configured and/or optimized for capturing different analytes or different forms of the same analyte, (e.g., molecular vs. aerosol THC), or one or more other analytes. In one example, a test for a plurality of different disease conditions from a single breath sample is contemplated. A device for implementing such a test might have a plurality of channels configured and/or optimized for capture of a plurality of different breath-borne substances, which could then be processed in a manner as described herein.

The principles of operation of the methods, systems and apparatus described herein, while primarily developed and described with reference to inhalation of THC via marijuana smoking, are also expected to be applicable to ingestion of THC. While timeframes and biochemistry are different for edibles, the same thresholds correlated with THC breath concentration in breath are contemplated to be applicable in such contexts as well. Edibles generally contain a form of THC that is not psychoactive when ingested, but is subsequently metabolized to a psychoactive form. Antibodies for THC, or other THC binders as described herein, also bind to the THC metabolite rendering the methods described herein effective for measuring THC breath associated with edibles and comparing to a breath THC concentration threshold that has been associated with impairment.

In various embodiments, in order achieve picogram sensitivity the determining aspect of the method may involve an immunoassay. Suitable immunoassays may include surface-based antibody-down immunoassays, surface-based antigen-down immunoassays, noncompetitive immunoassays, heterogeneous competitive immunoassays, and homogeneous competitive immunoassays. Several suitable immunoassays will now be described with reference to FIGS. 3-7. The operation of these immunoassays and their generalization to other recognition elements will be well understood and implementation details for these immunoassays will be readily ascertained by those of ordinary skill in the art.

Figure 3A:
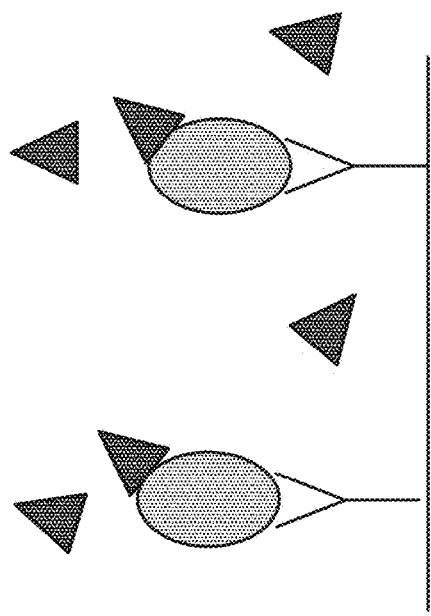
FIGS. 3A-D depict a surface-based antibody-down, direct diazonium reporter immunoassay.

FIGS. 3A-D depict a surface-based antibody-down, direct diazonium reporter immunoassay. According to this immunoassay, a THC binder, such as a monoclonal or polyclonal antibody, peptides, or aptamers, is/are surface-bound to the reaction channel walls according to well-known techniques. Surface binding to the reaction channel walls may be accomplished by passive adsorption, covalent binding, or a combination, for example. THC from the breath sample portion drawn into the reaction channel is captured by binding to the THC antibody, as depicted in FIG. 3A. Suitable reagents and reaction conditions are well or readily ascertained by those of ordinary skill in the art given the description provided herein. For example, in one implementation, mouse monoclonal anti-THC antibody is immobilized on the surface via passive adsorption. In solution, THC from breath sample binds to the antibody immobilized on the capture surface.

Figure 3B:
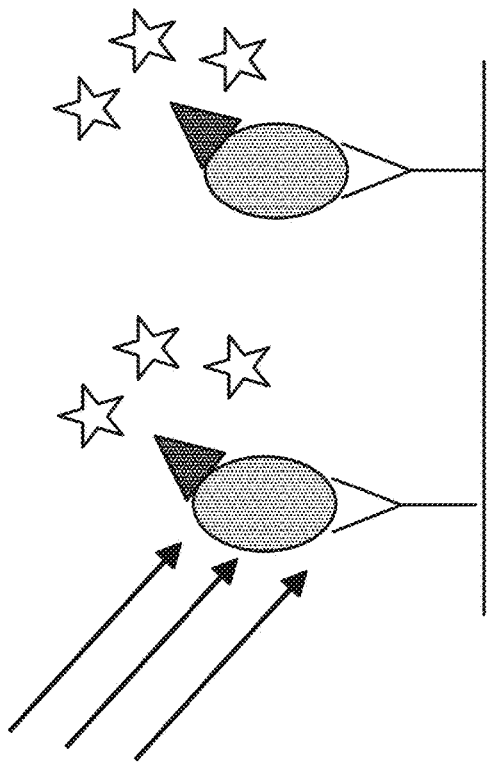

Determining an amount of THC captured from a breath sample obtained from a subject via this immunoassay involves flowing a diazotized fluorophore into the reaction channel and forming a solution such that the diazotized fluorophore binds to any THC from the breath sample portion captured by binding to the THC antibody to form a diazotized fluorophore-THC adduct, as depicted in FIG. 3B.

In various embodiments, the diazotized fluorophore has the formula:

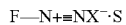

wherein:
F is a functionalized fluorophore;
N+≡N is a diazo functional group;
X⁻ is a negatively charged ion balancing the charge on the diazo functional group; and
S is a diazo functional group stabilizer.

F can be an amine-functionalized fluorophore, such as a primary amine-functionalized fluorophore. The fluorophore can be any one of: xanthene, cyanine, naphthalene, coumarin, oxadiazole, anthracene, pyrene, oxazine, acridine, arylmethine, tetrapyrrole, green fluorescent protein, red fluorescent protein, yellow fluorescent protein, cadmium selenide quantum dot, cadmium selenide/zinc sulfide alloy quantum dot, cadmium selenide sulfide quantum dot, cadmium selenide sulfide/zinc sulfide alloy quantum dot, cadmium telluride quantum dot, cadmium sulfide quantum dot, lead sulfide quantum dot, or indium phosphide/zinc sulfide alloy quantum dot derivatives, and mixtures thereof. In particular examples, the fluorophore is a xanthene, for example a rhodamine, for example rhodamine 123, for example rhodamine 123 diazotized at a primary amine group.

Figure 74:
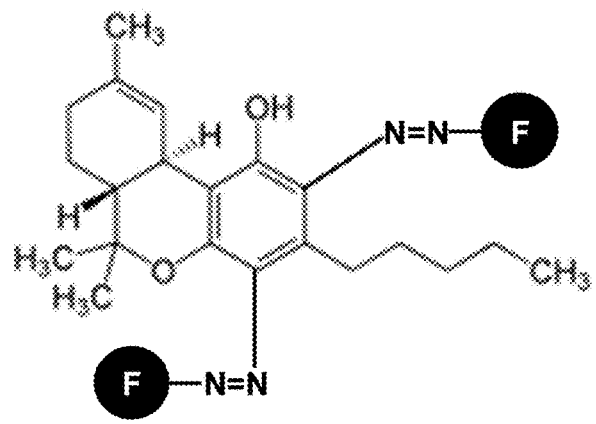
FIG. 74 depicts a formula for a fluorescent-labeled THC adduct.

The F—N+≡N group of a suitable diazotized fluorophore is selected to bind to a cannabinoid. In various embodiments, the F—N+≡N binds to the para or ortho position of a phenol ring of tetrahydrocannabinol forming an N═N azo bond such that an adduct is formed having the formula as depicted in FIG. 74, wherein F is the functionalized fluorophore, and only one or the other —N═N—F group is present.

Figure 75:
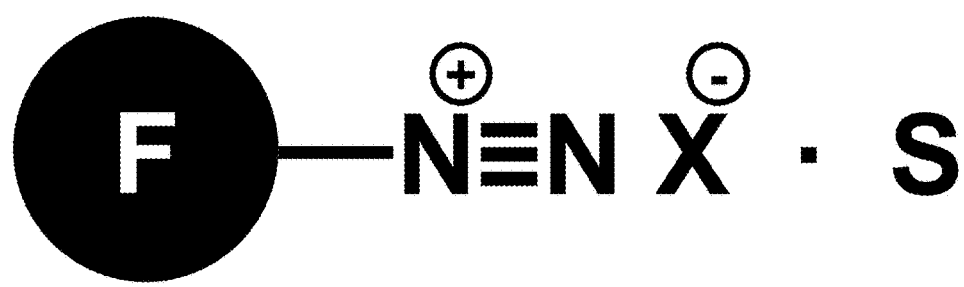
FIG. 75 depicts a formula for a diazotized fluorophore indicator/label.
Figure 76:
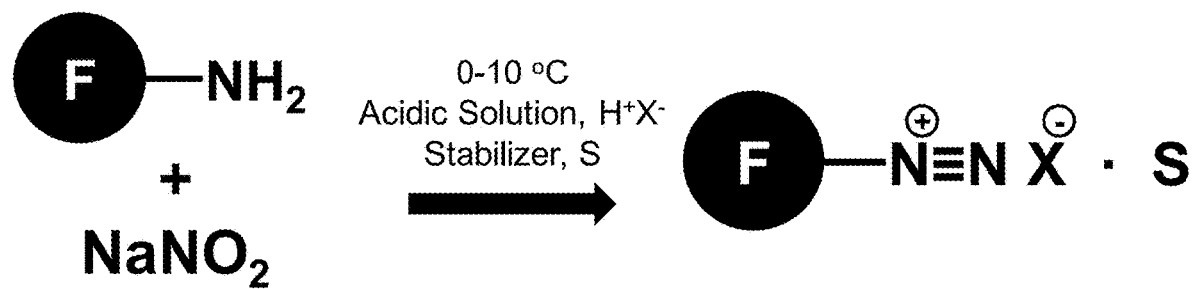
FIG. 76 depicts a process for synthesizing indicators including stabilized $N^+\equiv N$ diazo functional groups.

The acidic diazotized fluorophore solution is formed from constituent materials in an acidic solution. For example, the acidic solution may contain dilute HCl, such as 100 μM HCl. Indicators/labels containing stabilized N⁺≡N diazo functional groups can be been synthesized to rapidly (e.g., <2 min) and selectively bind to THC and/or derivatives thereof at the para or ortho position of the phenol ring forming an N═N azo bond. The binding produces a chemically bonded fluorescent-labeled THC adduct. The diazotized fluorophore indicator/label is generally of the form as depicted in FIG. 75, where:

F is a fluorophore, examples of which may include xanthene, cyanine, naphthalene, coumarin, oxadiazole, anthracene, pyrene, oxazine, acridine, arylmethine, tetrapyrrole, green fluorescent protein, red fluorescent protein, yellow fluorescent protein, cadmium selenide quantum dot, cadmium selenide/zinc sulfide alloy quantum dot, cadmium selenide sulfide quantum dot, cadmium seleninde sulfide/zinc sulfide alloy quantum dot, cadmium telluride quantum dot, cadmium sulfide quantum dot, lead sulfide quantum dot, or indium phosphide/zinc sulfide alloy quantum dot derivatives, or any combination thereof;

N⁺≡N is a diazo-functional group that is chemically bonded/grafted/functionalized/conjugated to F;

X⁻ is a negatively charged ion that charge balances the positively charged diazo functional group N⁺≡N, examples of which may include fluoride, sulfide, chloride, nitride, bromide, iodide, arsenate, phosphate, arsenite, hydrogen phosphate, dihydrogen phosphate, sulfate, nitrate, hydrogen sulfate, nitrite, thiosulfate, sulfite, perchlorate, iodate, chlorate, bromate, chlorite, hypochlorite, hypobromite, carbonate, chromate, hydrogen carbonate, dichromate, acetate, formate, cyanide, amide, cyanate, peroxide, thiocyanate, oxalate, hydroxide, or permanganate ion derivatives, or any combination thereof;

S is a N⁺≡N stabilizer, for prevention of decomposition of the diazo compound, composed of salts and/or polymers, examples of which may include tin chloride, cadmium chloride, manganese chloride, zinc chloride, sodium fluoroborate, aromatic, aliphatic, or heterocyclic sulfonic acids, sulfates, and chlorides, polymers with free terminal halo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, methylenedioxy, orthocarbonate ester, amide, amine, ammonium, imine, imide, azide, azo, diazo, cyanate, nitrate, nitrile, nitro, pyridine, thiol, sulfide, disulfide, sulfoxide, sulfone, sulfinic acid, sulfonic acid, camphosulphonic acid, thiocyanate, thione, thial, sulfonyl chloride, carbonyl chloride, phosphine, phosphonic acid, phosphate, phosphodiester, boronic acid, boronic ester, boronic acid, borinic ester, or any combination thereof.

Indicators including stabilized $N^+{\equiv}N$ diazo functional groups can be synthesized, for example, by a process including the combination of a primary amine ($-NH_2$) functionalized fluorophore, F (listed above), in an acidic solution ($H^+X^-$) with sodium nitrite ($NaNO_2$) and stabilizers, S (listed above) as depicted in FIG. 7B.

Figure 3C:
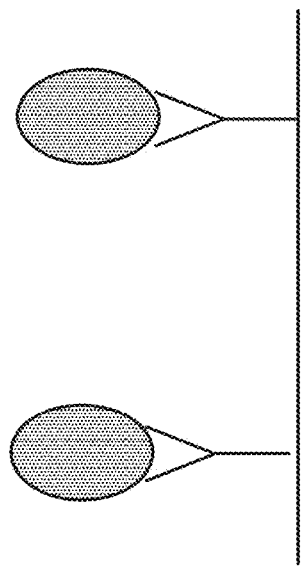
Figure 3D:
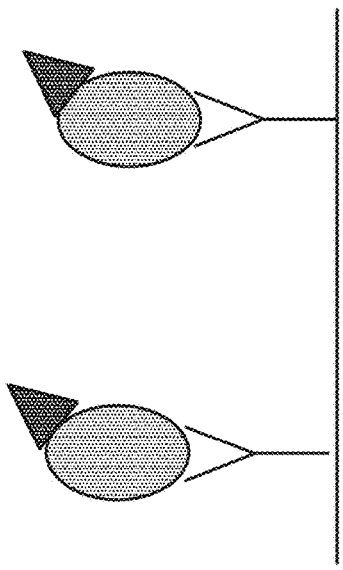

The diazotized fluorophore-THC adduct is then exposed to a light source in situ in the reaction channel to produce a fluorescence, as depicted in FIG. 3D. For example, the diazotized fluorophore may be rhodamine 123 diazotized at a primary amine group, the excitation wavelength may be 511 nm and the emission wavelength may be 534 nm. The fluorescence may be measured, the amount of THC captured from the breath sample determined based on the measured fluorescence.

In this direct immunoassay, the measured fluorescence is directly proportional to the amount of THC captured from the breath sample.

In various embodiments, prior to exposing the diazotized fluorophore-THC adduct to the light source to produce the fluorescence, any unbound breath constituents and unbound diazotized fluorophore is washed away from the reaction channel, as depicted in FIG. 3C. For example, the washing operation may involve flowing a buffer such as Phosphate Buffered Saline with surfactant such as 0.01% tween-20. Other suitable buffers include tris-buffered saline and similar buffers. Particularly suitable wash buffer is generally derived empirically by the person of ordinary skill. While the fluorescent signal of the adduct has a spectral difference from unbound diazotized fluorophore and so can be likely detected in a homogeneous assay (without a wash step), a wash step is generally used to remove any other breath constituents that could also bind the diazotized fluorophore and therefore contaminate the assay.

FIGS. 4A-C depict a surface-based competitive antibody-down, chemiluminescence immunoassay. According to this immunoassay, a THC binder, such as a monoclonal or polyclonal antibody, peptides, or aptamers, is/are surface-bound to the reaction channel walls according to well-known techniques. Surface binding to the reaction channel walls may be may be accomplished by passive adsorption, covalent binding, or a combination, for example. THC from the breath sample portion drawn into the reaction channel is captured by binding to the THC antibody, as depicted in FIG. 4A. Suitable reagents and reaction conditions are well or readily ascertained by those of ordinary skill in the art given the description provided herein, for example, as described above.

Determining an amount of THC captured from a breath sample obtained from a subject via this immunoassay involves flowing a known amount of an enzyme-conjugated synthetic THC antigen into the reaction channel and forming a solution such that any THC from the breath sample portion captured by binding to the THC antibody competes with the enzyme-conjugated synthetic THC antigen to bind to the surface-bound THC antibody, as further depicted in FIG. 4A.

Then, as depicted in FIG. 4B, any unbound THC from the breath sample portion and any unbound enzyme-conjugated synthetic THC antigen is washed away from the reaction channel.

After the wash operation, a chemiluminescent substrate for the enzyme is flowed into the reaction channel and the enzyme is allowed to activate the chemiluminescent substrate, as depicted in FIG. 4C, and the chemiluminescence is measured and the amount of THC captured from the breath sample determined based on the measured chemiluminescence.

In various embodiments, the measuring may be done in situ in the reaction channel. In various embodiments, the measuring is done ex situ of the reaction channel in a separate fluidically-connected channel or chamber.

In this competitive immunoassay, the measured fluorescence is inversely proportional to the amount of THC captured from the breath sample.

FIGS. 5A-C depicts a surface-based antigen-down, heterogeneous, competitive single-antibody immunoassay. According to this immunoassay, a synthetic THC antigen, such as THC-BSA hapten, is surface-bound to the reaction channel walls. Surface binding to the reaction channel walls may be accomplished by passive adsorption, covalent binding, or a combination. Suitable reagents and reaction conditions are well or readily ascertained by those of ordinary skill in the art given the description provided herein.

THC from the breath sample portion drawn into the reaction channel is captured by adsorption on the reaction channel walls. Determining an amount of THC captured from a breath sample obtained from a subject via this immunoassay involves flowing a known amount of an enzyme-conjugated THC antibody into the reaction channel and forming a solution with any THC from the breath sample portion, such that any THC from the breath sample portion competes with the surface bound THC antigen for the enzyme-conjugated THC antibody in the solution, as depicted in FIG. 5A.

Then, as depicted in FIG. 5B, any unbound THC from the breath sample portion and any unbound enzyme-conjugated THC antibody is washed away from the reaction channel.

After the wash operation, a chemiluminescent substrate for the enzyme is flowed into the reaction channel and the enzyme is allowed to activate the chemiluminescent substrate, as depicted in FIG. 5C, and the chemiluminescence is measured and the amount of THC captured from the breath sample determined based on the measured chemiluminescence.

In various embodiments, the measuring may be done in situ in the reaction channel. In various embodiments, the measuring is done ex situ of the reaction channel in a separate fluidically-connected channel or chamber.

In this competitive immunoassay, the measured fluorescence is inversely proportional to the amount of THC captured from the breath sample.

FIGS. 6A-D depicts a surface-based antigen-down, heterogeneous, competitive two-antibody immunoassay. According to this immunoassay, a synthetic THC antigen is surface-bound to the reaction channel walls according to well-known procedures, such as described above. Suitable reagents and reaction conditions are well or readily ascertained by those of ordinary skill in the art given the description provided herein.

THC from the breath sample portion drawn into the reaction channel is captured by adsorption on the reaction channel walls. Determining an amount of THC captured from a breath sample obtained from a subject via this immunoassay involves flowing a known amount of a THC antibody into the reaction channel and forming a solution with any THC from the breath sample portion, such that any THC from the breath sample portion competes with the surface bound THC antigen for the THC antibody in the solution, as depicted in FIG. 6A.

Then, as depicted in FIG. 6B, any unbound THC from the breath sample portion and any unbound THC antibody is washed away from the reaction channel.

After this wash operation an enzyme-conjugated second antibody is flowed into the reaction channel forming a solution, such that the enzyme-conjugated second antibody binds to the THC antibody on the surface bound THC antigen, as depicted in FIG. 6C.

Then, any unbound THC from the breath sample portion and any unbound THC antibody is washed away from the reaction channel.

After this second wash operation, a chemiluminescent substrate for the enzyme is flowed into the reaction channel and the enzyme is allowed to activate the chemiluminescent substrate, as depicted in FIG. 6D, and the chemiluminescence is measured and the amount of THC captured from the breath sample determined based on the measured chemiluminescence.

In various embodiments, the measuring may be done in situ in the reaction channel. In various embodiments, the measuring is done ex situ of the reaction channel in a separate fluidly-connected channel or chamber.

In this competitive immunoassay, the measured fluorescence is inversely proportional to the amount of THC captured from the breath sample.

In various implementations of the chemiluminescent embodiments described above with reference to FIGS. 4, 5 and 6, the enzyme may be horseradish peroxidase (HRP) and the substrate may be, for example, TMB (3,3',5,5'-tetramethylbenzidine), which gives blue reaction products upon reaction with HRP that have major absorbance peaks at 370 nm and 652 nm; OPD (o-phenylenediamine) which gives a yellow-orange, water-soluble reaction product with an absorbance maximum of 492 nm upon reaction with HRP; or ABTS (2,2'-Azinobis [3-ethylbenzothiazoline-6-sulfonic acid]) which gives a green, water-soluble end reaction product upon reaction with HRP that gives two major absorbance peaks at 410 nm and 650 nm. These reagents are available from Sigma-Aldrich.

FIGS. 7A-C depicts a homogeneous competitive immunoassay. According to this immunoassay, THC from the breath sample portion drawn into the reaction channel is captured by adsorption on the reaction channel walls, as depicted in FIG. 7A. Determining an amount of THC captured from a breath sample obtained from a subject via this immunoassay involves a luminescent oxygen channeling immunoassay (LOCI™) or AlphaLISA™ immunoassay, such as are described in Luminescent oxygen channeling assay (LOC™): sensitive, broadly applicable homogeneous immunoassay method, E. F. Ullman et al., Clinical Chemistry, 42:9, 1518 (1996); and AlphaLISA immunoassays: the no-wash alternative to ELISAs for research and drug discovery, L. Beaudet et al., Perkin Elmer Application Notes, December 2008; incorporated by reference herein for background and details of the two assays. Antibody specific to THC is immobilized on donor beads, either by direct adsorption or via Streptavidin-Biotin linkage. Acceptor beads are prepared by adsorbing a synthetic THC antigen.

In this context, these immunoassays involve flowing donor beads and acceptor beads into the reaction channel and forming a solution with any THC from the breath sample portion, such that any THC from the breath sample portion competes with synthetic THC bound to the acceptor beads to bind to antibody immobilized on the donor beads, as depicted in FIG. 7B. Donor beads bind either to free THC from the breath sample portion or to the acceptor beads' immobilized THC. The higher the concentration of free THC from breath sample, the lower the concentration of donor bead—acceptor bead pairs.

The donor bead-acceptor bead pairs in the solution are then exposed to a light source in situ in the reaction channel to produce a fluorescence, as depicted in FIG. 7C. For example, the, the, the excitation wavelength may be 680 nm and the emission wavelength may be 615 nm. This fluorescence signal is only emitted when the donor and acceptor beads are in close proximity to each other. This results in only bound pairs emitting light, while free beads do not emit any light. This reaction, which only occurs between beads which are in close proximity is what allows the homogenous phase immunoassay, without the requirement for washing, which is integral to traditional surface-based immunoassays.

The fluorescence may be measured and the amount of THC captured from the breath sample determined based on the measured fluorescence.

In this competitive, homogeneous immunoassay, the measured fluorescence is inversely proportional to the amount of THC captured from the breath sample.

Following completion of one of the immunoassay formats described above, the determined amount of THC captured the breath sample may be compared to a threshold level for THC in breath, such as described above with reference to FIG. 2, for example, less than 10 picogram/liter (pg/L) of breath, or from 2 to 5 pg/L of breath, or from 2 to 3 pg/L of breath, for example, about 2.4 pg/L of breath. However, as noted above, the threshold may vary depending upon the capture efficiency of the device or system with which the method is conducted.

Then, it may be indicated whether or not the amount of THC captured from the breath sample exceeds the threshold. A result wherein the amount of THC in the breath sample exceeds the threshold may be a positive test result for recent inhalation of THC, which may be correlated to THC impairment. In various embodiments, the indicating may include a visible and/or audible signal and/or readout on a display associated with a device on which the determination and comparison is conducted.

In various embodiments, the test cartridge on which methods described herein, particularly immunoassays, are conducted may be a microfluidic device.

In various embodiments, data corresponding to one or more of the determining the amount of THC captured from the breath sample obtained from the subject, the comparing the determined amount of THC from the breath sample to a threshold level for THC in breath, and the indicating whether or not the determined amount of THC captured from the breath sample exceeds the threshold, may be wirelessly transmitted to a remote location. In some instances, one or more processors and memory may include at least one processor and memory that are part of a device associated with the test cartridge. In such cases, there may be processors and memory distributed between two or more components, and the components may communicate with one another, either through a wireless communications interface or a wired connection. In some implementations, one or more of the components may also have a wireless communications interface, e.g., a cellular interface, that allows the one or more processors to wirelessly communicate information to a remote device, e.g., a server. For example, the device associated with the test cartridge may include a wireless interface that may transmit data corresponding to one or more of the determining the amount of THC in the breath sample obtained from the subject, the comparing the amount of THC determined to be in the breath sample to the threshold level of THC in breath, and the indicating whether or not the amount of THC in the breath sample exceeds the threshold, (as either entered manually by a user or as obtained automatically, e.g., through use of a GPS receiver located in the device or in another nearby piece of equipment, such as a paired smartphone or police car), and possibly other data such as one or more fingerprints of a subject, and/or a picture of the subject providing the sample, e.g., as taken by a paired smartphone or by a camera that may be built in to the device. The same wireless communications interface, or a different wireless communications interface, may also communicate test results to the same remote device in association with such information or in association with a record identifier linking such further information to previously transmitted information, allowing test results to be associated with a particular subject and sampling time/location. In some implementations, the wireless interface that may allow for such long-range communications, e.g., a cellular interface, may be integrated into only one of the components of the device, and the other components may communicate wirelessly with the base station using shorter-range communications systems, e.g., Bluetooth, and the base station may then act as a relay and send data collected by the other components on to the remote device.

In various embodiments, the breath sample obtained from the subject is also tested for a second substance, in particular ethanol, such that both THC and ethanol are measured from the same breath sample. According to such embodiments, another portion of the breath sample may be routed through a blood alcohol concentration (BAC) sensor for ethanol measurement. BAC sensors and their operation are well known in the art. Briefly, in a typical example of a fuel call-based BAC sensor, when a subject exhales into a breath analyzer, any ethanol present in their breath is oxidized to acetic acid at the anode. At the cathode, atmospheric oxygen is reduced. The overall reaction is the oxidation of ethanol to acetic acid and water. The electric current produced by this reaction is measured by a microcontroller, and displayed as an approximation of overall blood alcohol content (BAC). Blood alcohol content or concentration is not measured directly, which would require the analysis of a blood sample. Instead, a BAC sensor determines BAC indirectly by measuring breath alcohol level. Any suitable BAC sensors may be integrated with a device associated with the test cartridge, for example fuel cell based sensors from PAS Systems, Inc.

In various embodiments, the breath sample may be obtained from the subject after exposing the subject to a well-ventilated area (for example, outdoors) for at least 15 minutes. Subjects exposed to secondhand smoke will only have THC in their breath for a very brief time, and it disappears after a person is no longer exposed to this smoke. Accordingly, subjects exposed to secondhand smoke can be placed outdoors or in a well-ventilated area for 15 minutes before a breath test is performed to avoid a false positive associated with secondhand smoke exposure.

In various embodiments, in order to meet the evidentiary standards associated with roadside sobriety tests, an equal portion of the breath sample as drawn into the reaction channel may be drawn into an evidence channel on the test cartridge. This "B" sample can be retained for future testing to validate the test result. The "B" sample may be eluted from the evidence channel into a solution in a separate receptacle, or left in the evidence channel on the test cartridge channel, for storage or off-site analysis.

The methods, systems and apparatus described herein may also be adaptable as a platform for detection and evaluation of other airborne/breath-borne substances, including controlled substances, and breath-borne indicators of various disease states. In this regard, this disclosure also relates to a method for evaluating a substance (or analyte), more generally, in human breath, the method involving determining an amount of a substance captured from a breath sample obtained from a subject, comparing the determined amount of the substance captured from the breath sample to a threshold level for the substance in breath, and indicating whether or not the determined amount of the substance captured from the breath sample exceeds the threshold. The substance may be associated with a human disease condition, and the threshold may be correlated with a baseline maximum level of the substance in human breath for a subject not suffering from the disease condition. The substance may be associated with a human disease condition such as stomach cancer, lung cancer, heart failure, kidney failure or diabetes, for example. Substances associated with various human disease conditions are described, for example, in Biomarkers in exhaled breath condensate: a review of collection, processing and analysis, N M Grob, M Aytekin, and R A Dweik, J Breath Res. 2008 September; 2(3): 037004, which is incorporated by reference herein for its disclosure relating to breath-borne substances associated with various human disease conditions. As noted above, in one example, a test for a plurality of different disease conditions from a single breath sample is contemplated. A device for implementing such a test might have a plurality of channels configured and/or optimized for capture of a plurality of different breath-borne substances, which could then be processed in a manner as described herein.

This disclosure also relates to systems and apparatus for measuring tetrahydrocannabinol (THC) level from a breath sample in accordance with the methods herein described. Such a system, and variants thereof, is discussed in more detail below.

Figure 8:
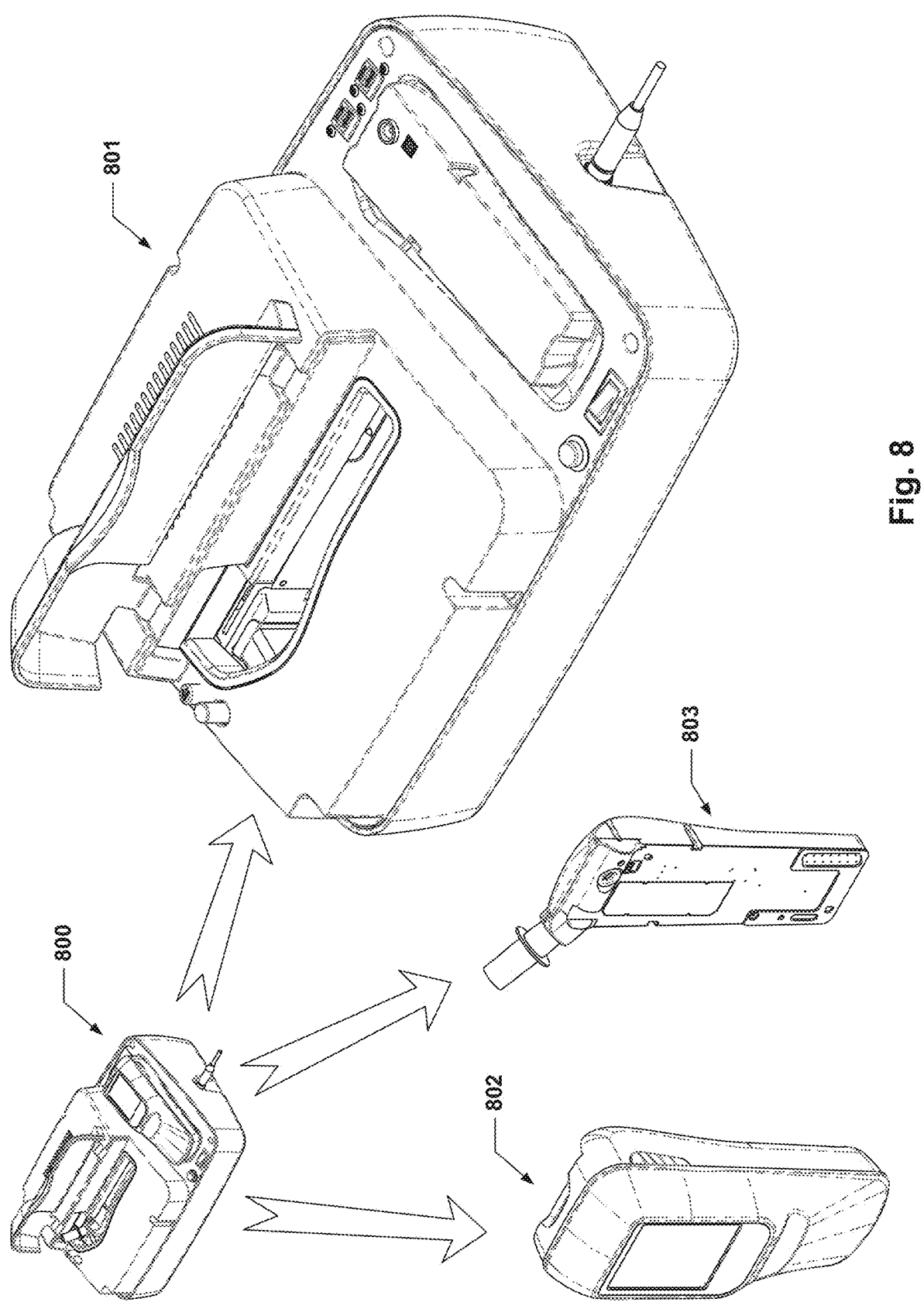
FIG. 8 depicts an example breath sampling and analysis system.

FIG. 8 depicts an example breath sampling and analysis system. In the depicted example system 800, the system includes three main components—a base station 801, a handheld unit 802, and a cartridge, or disposable, 803. This example breath sampling and analysis system will be used herein to discuss various aspects of breath sampling and analysis systems according to the present disclosure in general, but it will be understood that other implementations of breath sampling and analysis systems according to the concepts disclosed herein may take other forms. For example, while the example system features the base station 801, the handheld unit 802, and the cartridge 803, other systems may combine or otherwise distribute the functionality of one or more of these elements into other components. For example, the handheld unit 802 may be connected with the cartridge 803 in order to collect a breath sample, as the handheld unit 802 is small, relatively lightweight, and easily wielded by whomever is obtaining the breath sample. The cartridge 803 may then be removed from the handheld unit 802 and both elements separately docked in the base station 801 in order to perform the analysis and report out the results. However, it will be understood that, for example, the base station 801 and the handheld unit 802 could be combined into one device, although the resulting apparatus would not be as portable as the handheld unit 802 and obtaining a breath sample using such an apparatus would likely require extra effort on behalf of the subject. Similarly, the functionality of the cartridge 803 could be combined with the handheld unit 802, although doing so may complicate cleaning and re-use of the handheld unit 802.

While the breath sampling and analysis system 800 discussed herein is designed for use as a THC and alcohol detection system, it will be understood that similar systems, with appropriate modification, may be used to detect one or more additional or alternative analytes, as noted earlier. For example, the breath sampling and analysis system architecture discussed herein may also be used generally to capture breath samples that may then be analyzed to determine amounts of other controlled substances (or byproducts of using such controlled substances), symptomatic byproducts or biomarkers of particular medical conditions such as diabetes (in which high levels of acetone or other ketones may be present in a person's breath), or indicators of particular physiological states such as ketosis (in which acetone levels may be elevated as well). In general, the systems and architecture provided herein allow for breath samples containing potentially very small volumetric densities or concentrations of analytes, e.g., with magnitudes on the picogram-per-liter scale, to be captured and concentrated in reaction volumes on the order of microliters or tens of microliters within microfluidic circuits/plates. Once captured, such volumes may be analyzed to determine the presence and quantity of a particular analyte of interest, e.g., according to any of the assay techniques discussed earlier. As discussed, while most of the discussion herein is with reference to an example such system for detecting THC, the principles set forth herein, and the overall architecture, may be applicable to systems for detecting a variety of different analytes, and the concepts laid out herein should not be viewed as being solely directed to THC detection systems and methods.

Figure 9:
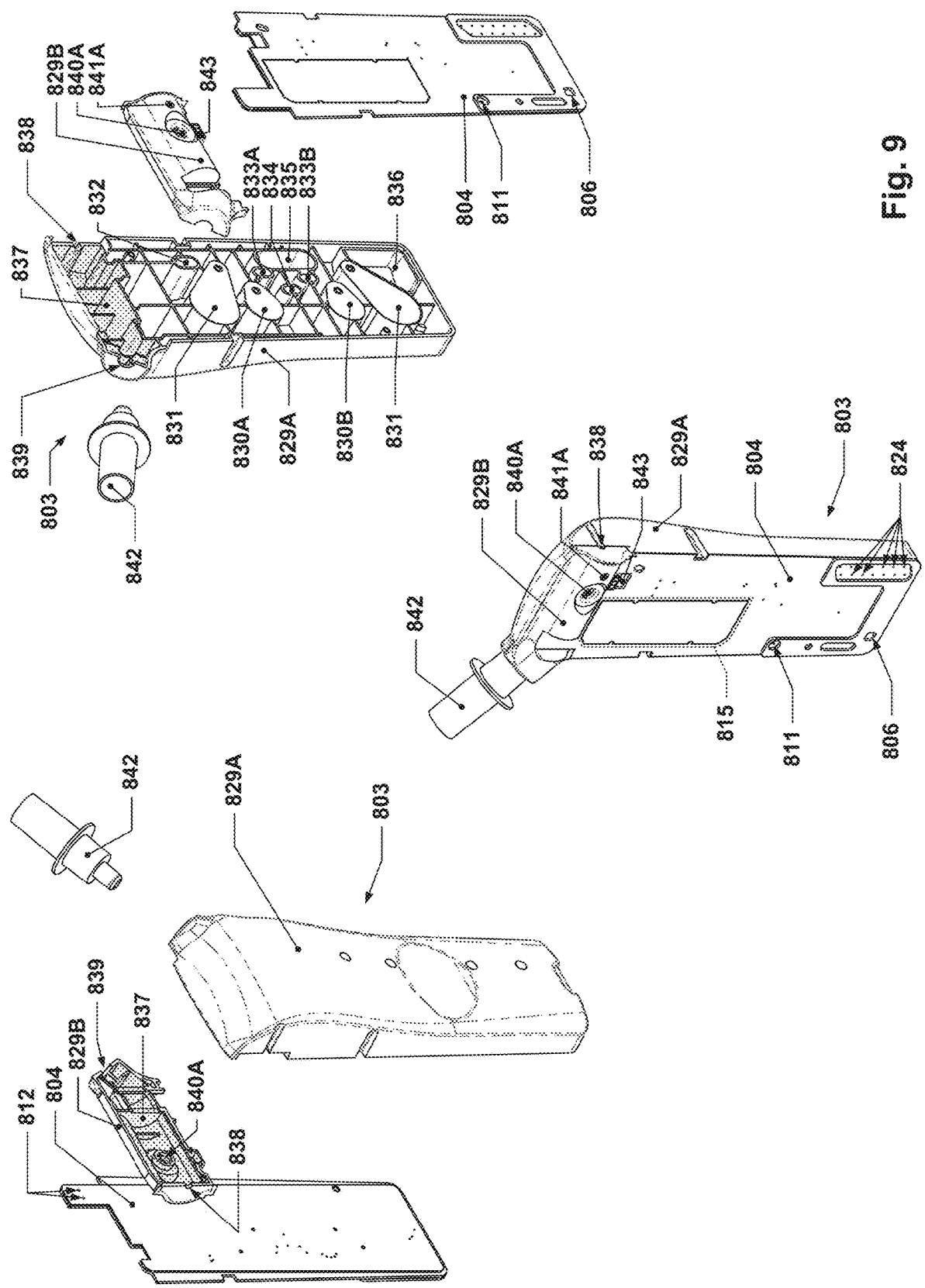
FIG. 9 depicts an example disposable element, or cartridge, of the example breath sampling and analysis system of FIG. 8.

FIG. 9 depicts an example disposable element, or cartridge, of the example breath sampling and analysis system of FIG. 8. Three views of the cartridge are shown; isometric exploded views of the cartridge from the front (right) and back (left) and an isometric assembled view of the front (middle). The cartridge 803 may include a housing 829, here shown as housing 829A and housing 829B, the walls of which may define a plenum 837 (the shaded volume). The plenum 837 may be a sealed volume that has an inlet 839, a flow restrictor 838, a pressure port 840A, and, in some implementations, a BAC (blood alcohol content) port 841A. The cartridge 803 may also include a microfluidic plate 804 (which may also be referred to herein as a µfluidic plate) that houses a network of microfluidic passages, pneumatic passages, pumps, valves, vents, and so forth that may provide one or more sample collection, preparation, and/or analysis functions. The microfluidic plate 804 may, for example, include one or more sample ports 812 in fluidic communication with the plenum 837. In some implementations, the microfluidic plate 804 may include a separate sub-module 815 that may be tailored to particular different types of analyses—thus, a variety of different sub-modules 815 may be provided and a suitable sub-module 815 selected for assembly with the underlying microfluidic plate 804, thus customizing the microfluidic plate 804 to a particular type of analysis. Such functionality will be explained further with reference to FIG. 10. It will be understood that some implementations of the microfluidic plate 804 may not have any such sub-module; in such implementations, the entire microfluidic plate 804 may be designed to detect and measure the amount of a specific analyte; entirely different microfluidic plates 804 would be used for detecting and/or measuring other analytes. Different sub-modules 815 may, for example, have reaction channels with reagents specific to different types of analytes immobilized on them. Such reagents may, for example, include antibodies or reagents specific to different types of analytes, but may also, for example, include non-immuno reagents. For example, e.g., an immune-based THC sub-module may have THC-specific antibodies or THC antigens immobilized on the reaction channel surfaces, whereas a sub-module for detecting acetone in breath, such as may be used in diagnosing some types of diabetes, may have acetone-specific reagents immobilized on the reaction channel surfaces. Thus, the microfluidic plate may be easily customized to allow it to be tailored to facilitate detecting any one of a variety of different types of analytes by installing an appropriate sub-module 815.

The sub-module may, for example, include a flat plate containing multiple, generally equal-length reaction channels. In various implementations, there may be 3 or 4 such reaction channels, although alternate implementations may have more or fewer reaction channels. In implementations with 3 reaction channels, one reaction channel may be reserved for collecting breath sample, and the other two may be reserved for containing control amounts of the analyte for which the sub-module is tailored to be used. In implementations with 4 reaction channels, the extra channel may also be reserved for collecting breath sample, but with the intention of simply preserving the breath sample for later analysis or for evidentiary purposes. In systems in which control amounts are not used, the sub-module may only have a single reaction channel or multiple reaction channels that are only reserved for sample collection. In other implementations, a sub-module may have additional reaction channels beyond four, e.g., additional reaction channels for additional control amounts of analyte, or additional reaction channels for sample collection.

The sub-module may generally be a flat plate having a surface that is intended to be bonded with the larger microfluidic plate, e.g., with a pressure-sensitive adhesive. In some implementations, the pressure-sensitive adhesive may be a layer that is adhered to the sub-module, thus providing the surface with an adhesive character that allows the sub-module to be adhered to the larger microfluidic plate. In some implementations, the reaction channels may be sealed entirely within the sub-module, e.g., such that no part of the reaction channel is exposed except for the very ends of the reaction channels. In such implementations, the ends of the reaction channels may terminate at inlet and outlet ports that penetrate through to the surface that is intended to be bonded to the microfluidic cartridge. Such inlet and outlet ports may be positioned in the sub-module such that they align with corresponding ports in the microfluidic plate when the sub-module is installed in the microfluidic plate. In other implementations, the reaction channels may simply be open trenches or troughs etched or cut into the surface of the sub-module that is intended to be bonded to the microfluidic plate. In such implementations, the reaction channels may each span between two locations that align with inlet and outlet ports of the microfluidic plate. When such a sub-module is installed, the surface of the microfluidic plate to which the sub-module is adhered may cover/seal the reaction channel trench or trough such that only the ends of the reaction channel may be collocated with the reaction channel inlet and outlet ports of the microfluidic plate.

It will be understood that the above-described structure of the sub-modules may be similar between sub-modules tailored for a plurality of different analyte analyses, but may differ with respect to what antibodies, antigens, and or other binding agents are immobilized on the surfaces of the reaction channels. Furthermore, sub-modules may optionally be loaded with different types and quantities of control analytes; such loading may occur prior to installation of the sub-module on the microfluidic plate, or may occur after such installation. Such loading may include, for example, flowing a known quantity of vapor-phase analyte into the control reaction channels and allowing the analyte to then adsorb onto the reaction channel walls.

For example, a non-limiting list of example sub-module customized analyses chemistries for detecting analytes that may be indicative of a variety of potential physiological conditions may include:

| Target analyte | Physiological condition to be detected/diagnosed | Immobilized antigen or antibody on surfaces of reaction channels in sub-module |
| --- | --- | --- |
| THC | Recent THC usage | THC-specific antibody or THC antigen |
| Acetone | Diabetes | Acetone-specific antibody, acetone antigen, or acetone reagent |
| Nitrites | Chronic Obstructive Pulmonary Disease (COPD) | Nitrite-specific antibody or nitrite antigen |
| 8-Isoprotane | Cystic Fibrosis | 8-isoprotane-specific antibody or 8-isoprotane antigen |
| Chromium | Lung cancer | Chromium-specific antibody or chromium antigen |
| Ammonia | Kidney failure | Ammonia-specific antibody or ammonia antigen |

The cartridge 803 may also include various liquids for use during a breath sample analysis. For example, the cartridge 803 includes two buffer blisters 831, a substrate blister 830A, and a substrate blister 830B. The blisters, in this example, are blister packs, e.g., compressible bladders that house liquid, although other types of liquid storage may be used in other implementations. In addition to the buffer blisters 831 and the substrate blisters 830A/B, the cartridge 803 also provides structures that, in conjunction with the microfluidic plate 804, define a number of different reservoirs. For example, the housing 829A may include a buffer reservoir 835, substrate reservoirs 833A and 833B, a substrate mixing reservoir 834, an antibody reservoir 832, and a waste reservoir 836.

During use, the cartridge 803 may have a mouthpiece 842 inserted into the inlet 839; the subject may then breath through the mouthpiece. The exhaled breath may then travel through the plenum 837 and out through the restrictor 838. Since the restrictor 838 is of a smaller cross-sectional area than the inlet 839, a positive pressure of 1-2 psi may develop within the plenum 837 when the subject breathes into the mouthpiece 842; this positive pressure may be measured by a pressure sensor, e.g., one internal to the cartridge 803 or one that measures the pressure via the pressure port 840A, to characterize the breathing behavior of the subject. The positive pressure may cause portions of the breath sample collected to flow through the BAC port 841A, if present, and through the sample ports 812 on the microfluidic plate 804. The cartridge 803 may also include a memory device 843 that may, for example, be used to store data pertaining to a sample collected using the cartridge 803. The memory device 843 may, for example, be an encrypted data storage device or non-volatile memory that may be used to store, for example, one or more types of information collected at various times through use of the system, such as subject vital statistics (name, age, driver's license number, social security number, date of birth, photograph, fingerprint, signature, voiceprint, etc.), environmental information relating to sample collection (ambient temperature, ambient humidity, ambient barometric pressure, etc.), sample collection information (identity of person taking sample, time and date of sample collection, location of sample collection, etc.), and/or sample metrics (amount of breath sample passing through microfluidic plate, duration of breath sample collection, pressure-time history of plenum 837 during breath sample collection, and measured levels of one or more analytes).

In some implementations, the microfluidic plate 804 may have a vacuum assist port 811 that may be fluidically connected with the sample ports 812 via one or more sample collection passages within the microfluidic plate 804. During sample collection, negative pressure may be applied to the vacuum assist port 811 in order to decrease the pressure in the sample collection passages and the sample ports 812, thereby increasing the pressure differential between the plenum 837 and the sample collection passages of the microfluidic plate 804 and causing an increased proportion of the breath sample to pass through the sample collection passages. This can increase the concentration of analyte that may be collected within the sample collection passages.

The microfluidic plate 804 may also include an optical measurement site 806 that is optically transparent (at least, transparent in the portion of the microfluidic plate interposed between the optical measurement site and the device used to take the optical measurements) to allow optical measurements to be taken of samples that are contained within the optical measurement site 806. The microfluidic plate 804 may also include a plurality of pneumatic control ports 814 that may be interfaced with corresponding pneumatic sources in order to actuate valves within the microfluidic plate 804.

Figure 10:
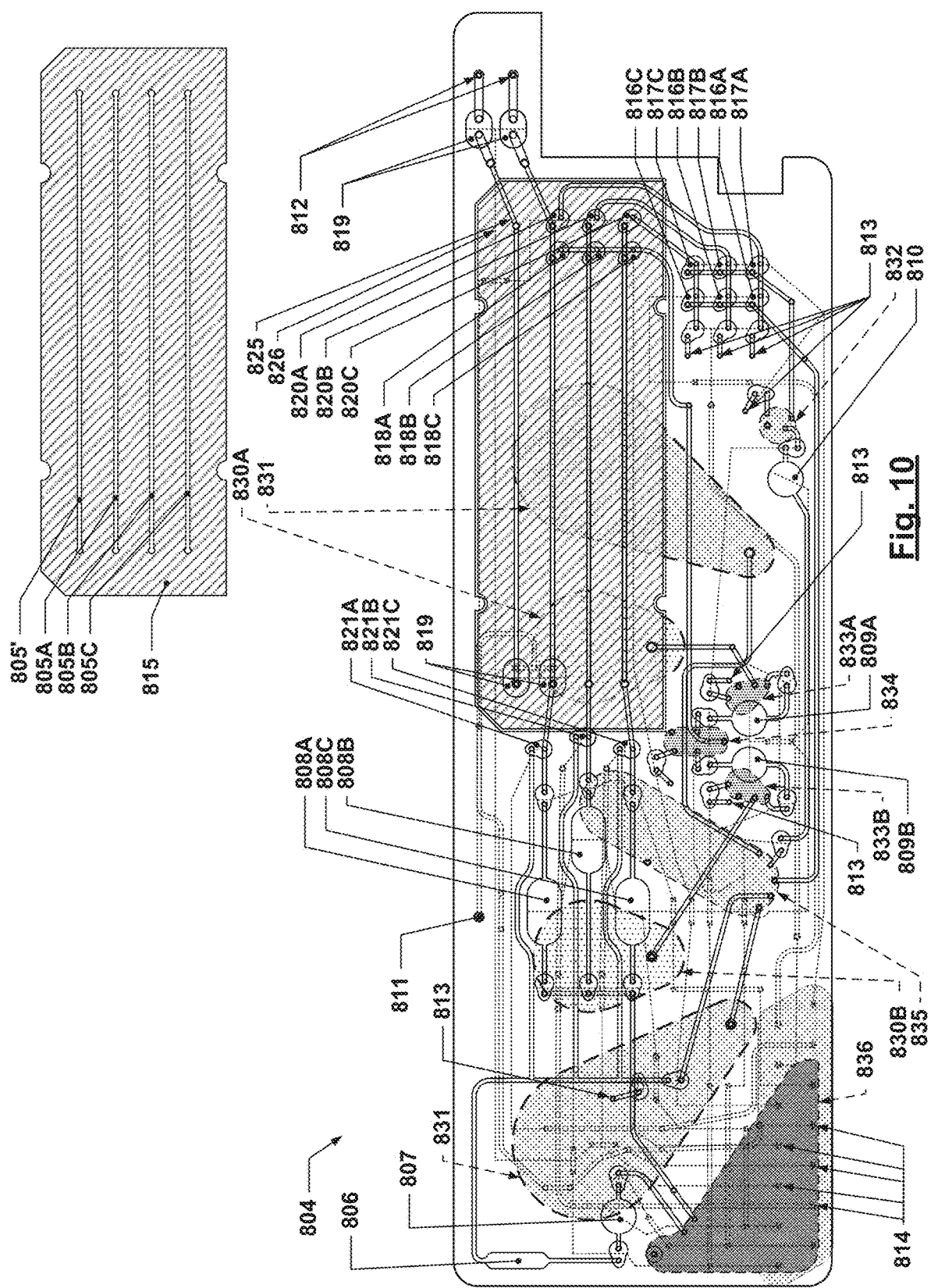
FIG. 10 depicts an example microfluidic plate that may be used with the example breath sampling and analysis system of FIG. 8.

FIG. 10 depicts an example microfluidic plate that may be used with the example breath sampling and analysis system of FIG. 8. As shown in FIG. 10, the microfluidic plate 804 is a bonded stack of multiple layers of material—some material which is rigid, e.g., acrylic, and some material which is flexible, e.g., an elastomer. For reference, the microfluidic plate 804 of FIG. 10 also includes indications of the locations of reservoirs and blisters that are housed within the housing 829A, e.g., the buffer blisters 831, the substrate blisters 830A/B, the substrate reservoirs 833A/B, the substrate mixing reservoir 834, the waste reservoir 836, the buffer reservoir 835, and the antibody reservoir 832. Such reservoir and blister locations are indicated using broken/dashed lines and the regions occupied by such structures are shaded for enhanced clarity.

The microfluidic plate 804 includes several reaction channels 805; such reaction channels 805 may include, for example, two reaction channels 805' and 805A that may be used to collect a breath sample from a subject, e.g., breath sample may be flowed into sample ports 812 and through such reaction channels 805' and 805A and any analyte therein may thus be provided an opportunity to adhere or adsorb on the walls of such reaction channels, thereby capturing the analyte for later analysis. In this particular example, the reaction channel 805' is intended to capture a sample for later laboratory analysis, e.g., for analysis in a criminal forensics laboratory (or for preservation of evidence in a criminal proceeding), and the reaction channel 805A is intended to capture a sample for immediate or near-immediate analysis. There are also, in this example, two additional reaction channels 805B and 805C, that may be used to house, for example, control amounts of the analyte being detected and measured. Since the reaction channels 805B and 805C in this example are used to house control amounts of the analyte in question, the reaction channels 805B and 805C are not configured to have breath sample flowed through them during sample collection.

As noted earlier, the microfluidic plate 804 may include a sub-module 815 that may include the reaction channels 805. The sub-module 815 is also shown removed, and the reaction channels 805' and 805A/B/C may be clearly seen. Also visible in the microfluidic plate 804 are the vacuum assist port 811, the optical measurement site 806, and a plurality of vents 813 (each of which may be sealable by way of a corresponding valve).

The microfluidic plate 804 may have a number of valves and pumps located at different points within the microfluidic plate 804; such valves and pumps may be controlled, for example, by pneumatic passages 825 (only one is indicated, but, generally speaking, the pneumatic passages extend from the pneumatic control ports 814; fourteen such ports are shown in this example, but it will be recognized that different numbers of pneumatic control ports 814 may be used in other implementations—in this Figure, the pneumatic control passages are represented by dotted lines or dotted channels/double lines). The microfluidic plate 804, in addition to containing the reaction channels 805, may also include various fluidic flow passages 826 (only one is specifically indicated) that may be used to route or control the flow of liquids (and, in some instances, also air, e.g., during purge/cleaning/washing operations); such fluidic flow passages are represented in FIG. 10 by channels with solid lines. The operation of such valves and pumps is discussed more fully later in this disclosure with reference to FIG. 11.

For example, the microfluidic plate 804 may include isolation valves 819, which may be actuated to seal or unseal the reaction channels 805' and 805A, e.g., during breath sample collection, the isolation valves 819 may be actuated to an open state, thereby allowing fluid to flow from the sample ports 812, through the reaction channels 805' and 805A, and into a pneumatic passage fluidically connected with the vacuum assist port 811. Once breath collection is complete, the isolation valves 819 may be allowed to close (or actuated so as to cause them to close), thereby sealing the collected breath samples within the reaction channels 805' and 805A. It will be understood that such "sealing" of the reaction samples may, after positive pressure is removed from the isolation valves 819 (such as when the handheld unit is deactivated or the cartridge 803 removed from the handheld unit 802), no longer be present due to the construction of some microfluidic diaphragm valves. While isolation valves 819 are depicted as diaphragm valves in this example, other suitable mechanisms for sealing off the reaction channels 805' and 805A may be used in place of the depicted valves.

The microfluidic plate 804 may, in addition to the isolation valves 819, also include a number of other valves, e.g., buffer valves 816A/B/C, antibody valves 817A/B/C, substrate valves 818A/B/C, reaction channel valves 820A/B/C, and optical site valves 821A/B/C.

As noted above, the microfluidic plate 804 may also include a number of pumps that may be actuated to move liquids between various locations within the microfluidic plate 804. For example, the microfluidic plate 804 may include one or more optical measurement site pumps 807, one or more reaction channel pumps 808A/B/C, one or more substrate pumps 809A/B, and one or more antibody pumps 810. In the depicted microfluidic plate 804, each included pump may generally include three elements—two valves and a chamber fluidically interposed between them. The operation of such a pump is discussed more fully later in this disclosure with reference to FIG. 11.

The implementation of FIG. 10 depicts only one example of a microfluidic plate that may be used to perform the microfluidic analysis protocols discussed elsewhere herein. Other examples are discussed later herein, although microfluidic plates falling within the scope of this disclosure are not limited to only the depicted examples.

Figure 11:
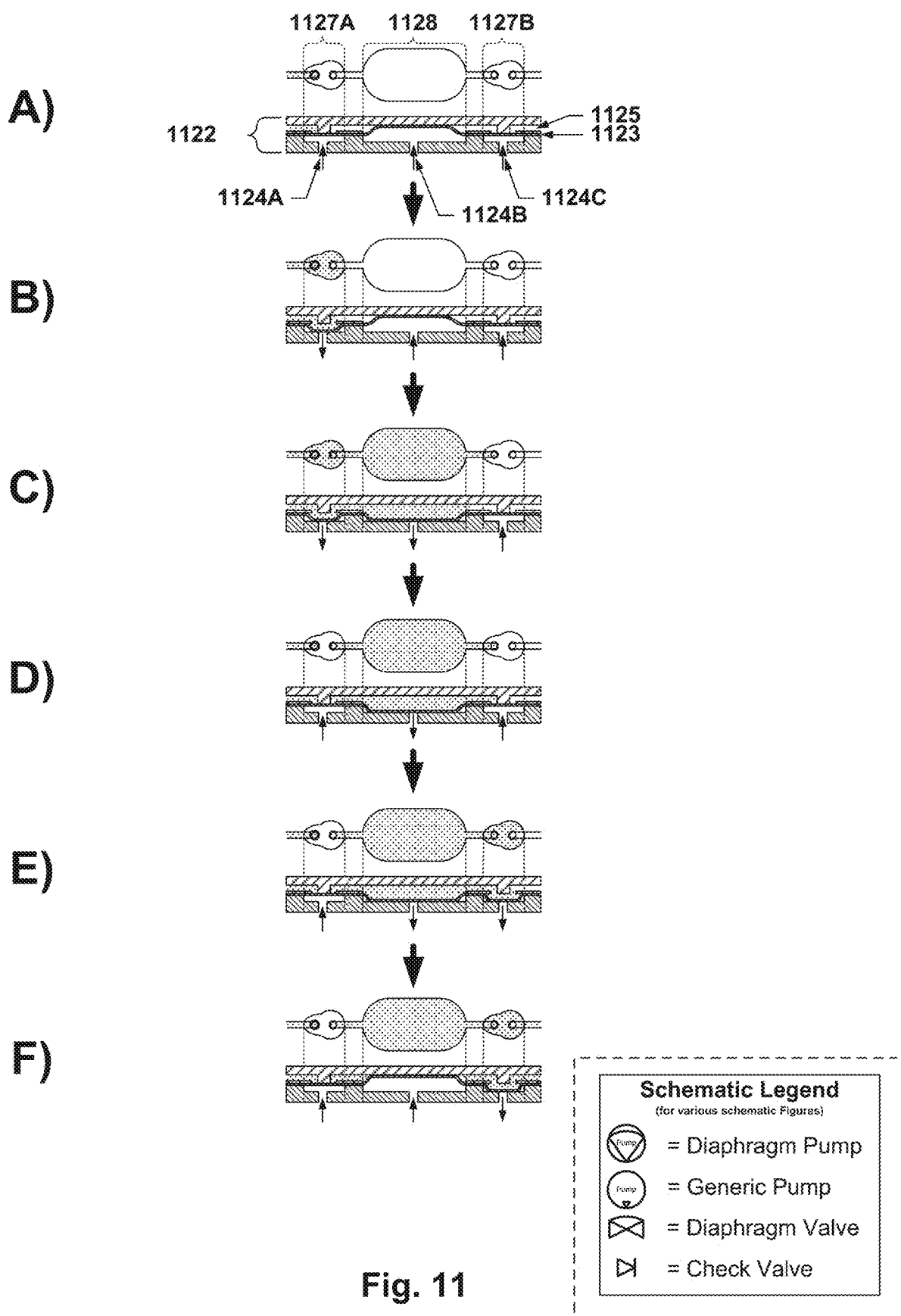
FIG. 11 depicts schematic views of an example microfluidic pump similar to microfluidic pumps that are depicted in the example microfluidic plate of FIGS. 10, 19, 20, and 21.

FIG. 11 depicts schematic views of an example microfluidic pump similar to microfluidic pumps that are depicted in the example microfluidic plates of FIGS. 10, 19, 20, and 21. In FIG. 11, a microfluidic pump is shown in various stages of operation (stages A-F); a plan view (above) and a side cross-section view (below) of the pump is provided for each stage. The microfluidic pump includes a chamber 1128 that is fluidically interposed between two valves 1127 and 1127B; these structures are provided in a microfluidic layer stack 1122. The microfluidic layer stack 1122 may include a number of discrete layers, although in this example, these layers are not individually shown except for membrane 1123, which may be made of an elastomeric material. In the depicted microfluidic layer stack 1122, a fluid channel 1125 passes through the portion of the microfluidic layer stack 1122 located above the membrane 1123, and pneumatic ports or features 1124A/B/C are located in the portion of the microfluidic layer stack 1122 located below the membrane 1123. For illustration purposes, a fluid being pumped through the pump in FIG. 11 is indicated through use of shading.

In state (A), the pump has not yet initiated a stroke cycle; all three pneumatic ports 1124A/B/C are pressurized. This causes the valves 1127A and 1127B to seal shut since the positive pressure received via pneumatic ports 1124A and 1124C pushes the membrane 1123 in the valve regions flat against the upper portion of the microfluidic layer stack 1122, thereby sealing off the fluid channel 1125 in those regions. The positive pressure received via the pneumatic port 1124B, in the interim, causes the membrane to distend into the chamber 1128, reducing the free volume within the chamber 1128. In state (B), the valve 1127A has been opened by providing a negative pressure to the membrane 1123 via the pneumatic port 1124A; this causes the membrane 1123 in the region of the valve 1127A to distend downwards (with regard to the figure orientation), thereby opening a fluid flow path into the chamber 1128. In state (C), the valve 1127A is kept open, and a negative pressure is applied to pneumatic port 1124B, thereby causing the membrane in the chamber 1128 to distend downwards, which, in turn, causes fluid to be sucked into the chamber 1128 via the valve 1127A. In state (D), positive pressure is again applied to pneumatic port 1124A, thereby causing the membrane 1123 in the region of the valve 1127A to flatten against the upper portion of the microfluidic layer stack 1122, thereby sealing the chamber 1128 with a volume of fluid trapped inside. In state (E), negative pressure is applied to pneumatic port 1124C, thereby causing the membrane 1123 to distend downwards and open a fluid flow path from the chamber 1128 through the valve 1127B. In state (F), the valve 1127B is kept open and positive pressure is then applied to the pneumatic port 1124B to cause the membrane 1123 in the region of the chamber to distend upwards, thereby forcing the fluid within the chamber to flow out through the valve 1127B. These operations may then be repeated as desired to deliver a desired amount of fluid volume to a location downstream of the pump. It will be understood that such pumps may be operated in reverse to cause fluid to flow in the opposite direction, and that such pumps may be referred to herein as "diaphragm pumps" or the like. In FIG. 10 and other microfluidic plate Figures herein, it is to be understood that the callouts indicating pumps generally only point to the "chamber" portion of the pumps; the valves that are included in such pumps may be determined by locating the valves immediately upstream and downstream of such chambers (these valves are not separately called out in FIG. 10).

Figure 12A:
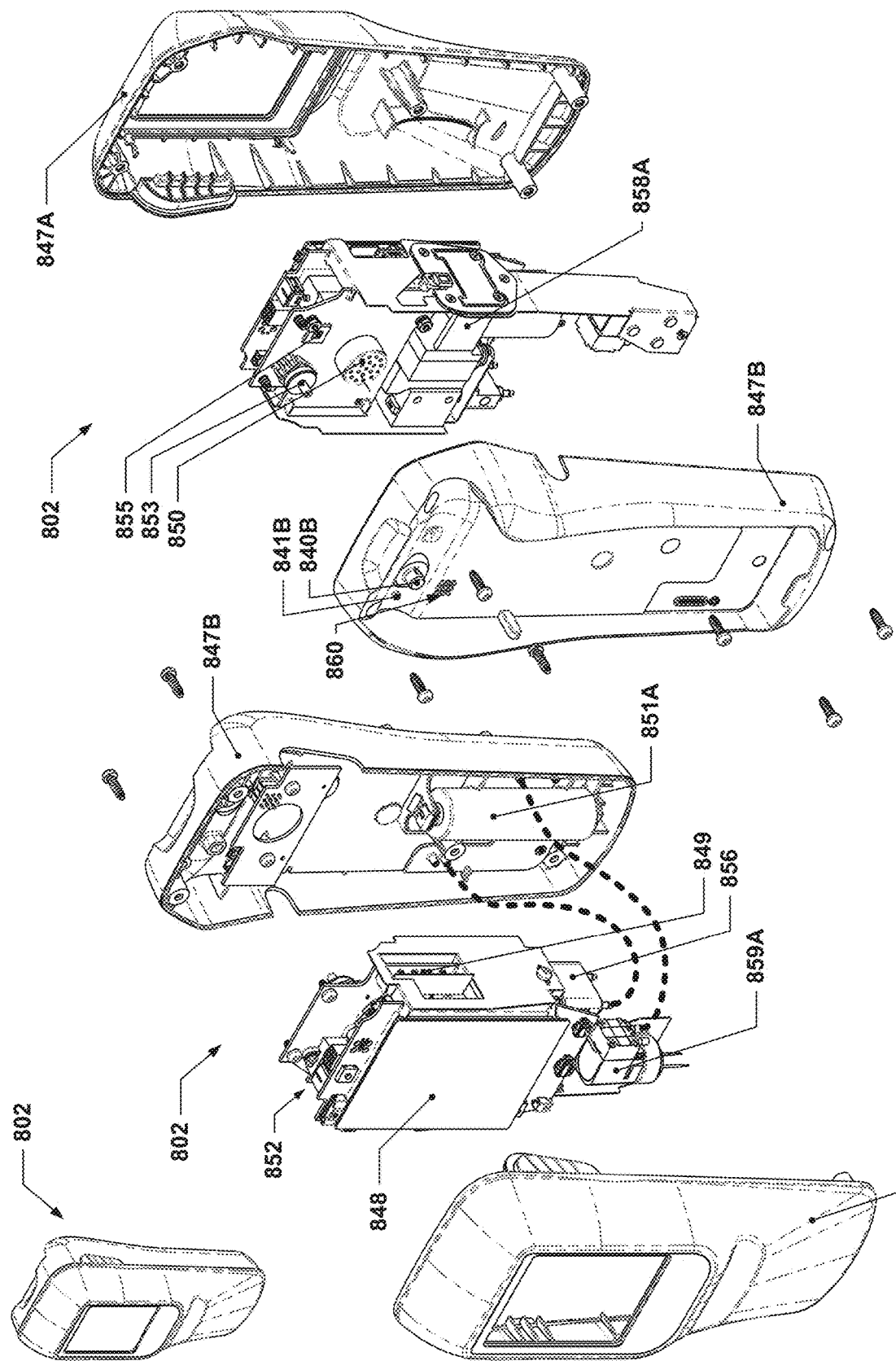
FIGS. 12A and 12B depict exploded views of an example handheld unit of the example breath sampling and analysis system of FIG. 8.
Figure 12B:
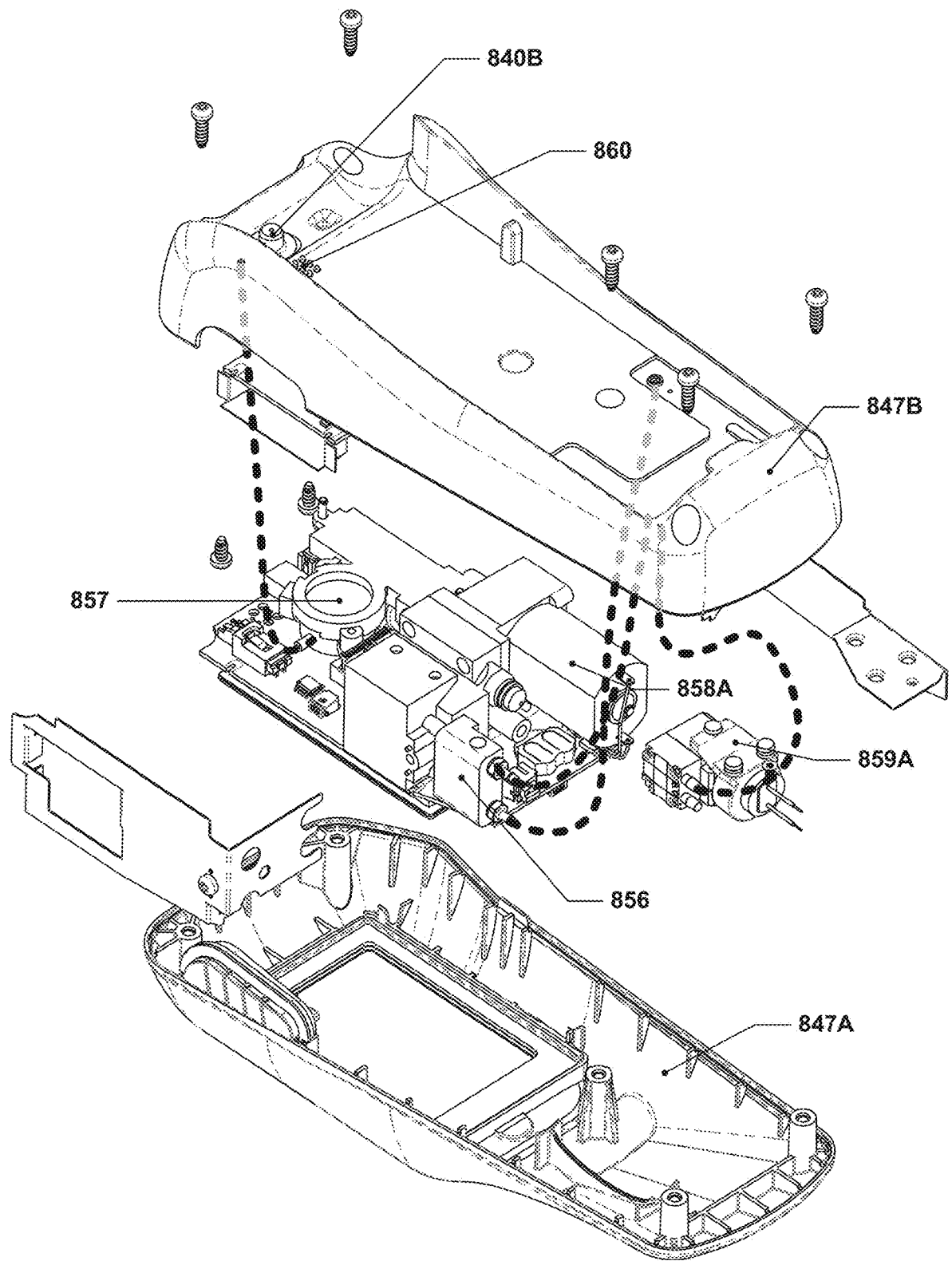

FIGS. 12A and 12B depict exploded views of an example handheld unit of the example breath sampling and analysis system of FIG. 8. Three views of the handheld unit 802 are shown in FIG. 12A; isometric exploded views of the handheld unit from the front (left) and back (right) and an isometric assembled view of the front (upper left). The handheld unit 802 may be sized to comfortably be held in a person's hand, e.g., in a one-handed grip, to facilitate use as a portable sampling device that may be maintained in the grip of the operator while the subject exhales into the mouthpiece 842. The handheld unit 802 may include, for example, a handheld housing 847, e.g., handheld housings 847A and 8476, which house a variety of components. The handheld unit 802 may further include a controller 852A, e.g., one or more processors, memory, and other electronic components, that may be configured to control one or more components of the handheld unit 802 to provide various functionalities. The controller 852A may, for example, be operatively and/or communicatively connected with a variety of user interface elements, e.g., a display 848 (which may, for example, be a touch-sensitive display to allow for user inputs to be received and communicated to the controller 852A), an annunciator (speaker or other audio output device) 850, and/or an indicator 849 (e.g., one or more LEDs or other visual indicators), to facilitate communications of system status, sample collection status, test results, and so forth.

The controller 852A may also be communicatively connected with a variety of sensors that may be active at least during sample detection. For example, the controller 852A may be communicatively connected with a pressure sensor 853, a humidity sensor 855, a BAC sensor 857, and a flow sensor 856. The pressure sensor 853 may be configured to measure pressure within the plenum 837 of the cartridge 803 when the cartridge 803 is mounted to the handheld unit 802; the controller 852A may monitor data from the pressure sensor 853 to determine, for example, what the ambient pressure conditions are prior to (and/or after) the collection of a breath sample from a subject, as well as what the pressure conditions are within the plenum 837 of the cartridge 803 during breath sample collection. To facilitate such measurements, the handheld housing 8476 may include a pressure port 840B that may seal to the pressure port 840A in the cartridge 803; the pressure sensor 853 may be configured to measure pressure in the plenum 837 via the pressure ports 840A and 840B when the cartridge 803 is installed and the two pressure ports 840A and 8406 are sealed together. As the pressures being measured may be quite low, e.g., 1-2 psi, based on the average pressure that human lungs typically are capable of generating, the seal interface between the pressure ports 840A and 840B may be a relatively light seal, e.g., a lightly compressed elastomeric seal.

In implementations with a BAC sensor 857, the BAC sensor 857 may be used to measure an amount of alcohol present in the breath sample. In such implementations, the BAC sensor 857 may have an air inlet port or ports that are fluidically connected with a BAC port 841B on the handheld housing 847B which interfaces with the BAC port 841A on the cartridge 803, thereby allowing a portion of the breath sample flowing through the plenum 837 to be siphoned off and passed through the BAC sensor 857. The BAC sensor 857 may, for example, be a fuel cell sensor equipped with a solenoid pump and a resistive heater, although other types of BAC sensor may be used as well.

The handheld unit 802 may also include one or more pumps, e.g., a vacuum pump 858A and a pressurization pump 859A, which may be used to actuate valves within the microfluidic plate when the cartridge 803 is installed in the handheld unit 802. The vacuum pump 858A may also be used to provide vacuum/negative pressure to the vacuum assist port 811 on the microfluidic plate 804 when the cartridge 803 is installed in the handheld unit 802 and while a breath sample is being obtained. It will be understood that such pumping functionality may be consolidated into a single pump or spread across multiple pumps. For example, a single pump may have an outlet that produces positively pressurized air and a corresponding inlet that generates negatively pressurized air—through the use of appropriate valves (not shown) in the handheld unit 802, the positively pressurized air and the negative pressurized air may be selectively routed to the various ports on the microfluidic plate 804 in order to selectively activate/deactivate features within the microfluidic plate 804 such as the vacuum assist and the isolation valves, e.g., isolation valves 819. In implementations such as the one depicted, separate pumps may be used to provide the vacuum assist (negative pressure) and valve actuation (positive and/or negative pressure). In yet further implementations, one pump may be supplied to provide negative pressure for the vacuum assist feature, a second pump may be supplied to provide negative pressure for valve actuation, and a third pump may be supplied to provide positive pressure for valve actuation. There may also be one or more additional pumps, as needed, for functionality unrelated to sample flow through the microfluidic plate 804. For example, the BAC sensor 857, if present, may incorporate a vacuum pump to assist with drawing breath sample through the BAC sensor 857.

As noted above, the handheld unit 802 may also incorporate a flow sensor 856, which may be fluidically interposed between the vacuum assist port 811 and the vacuum pump 858A (or whatever pump is used to provide vacuum assist functionality). In implementations that may not include vacuum assist functionality (and the attendant hardware), the flow sensor 856 may be configured to receive fluid (breath sample air) that flows through the microfluidic plate during breath sample collection; the flow sensor 856 may measure the amount of such fluid prior to the fluid being released back into the ambient environment. The flow sensor 856 may, for example, be a mass flow sensor or other similar sensor that may quantify the amount of breath sample that is diverted through the microfluidic plate 804 during breath sample collection. The data from the flow sensor 856 may, for example, be monitored by the controller 852A and when the data indicates that a predetermined amount of air (breath sample) has passed through the flow sensor 856 subsequent to the start of breath sample collection, then the controller 852A may cause one or more changes in operational status of the handheld unit 802. For example, the controller 852A may cause the vacuum pump 858A to cease applying negative pressure to the vacuum assist port 811 in the cartridge 803 and may concurrently cause the pressure pump 859A to apply positive pressure to the pneumatic control port(s) leading to the isolation valves 819, thereby causing the isolation valves to seal within the reaction channels 805' and 805A whatever breath constituents may have adsorbed onto the walls thereof while the breath sample was flowing therethrough. The controller 852A may also monitor the flow sensor 856 to determine what percentage of the predetermined amount of air has already passed through the microfluidic plate 804 and to provide progress indicators to the operator/subject, e.g., by providing visual and/or audio output indicative thereof. For example, in the example handheld unit 802, the indicator 849 may include a plurality of different light-emitting diodes (LEDs) that may be illuminated in different quantities and/or colors to indicate progress.

The handheld unit 802 may also include a communications interface 860 that may be configured to communicate electrical signals to the memory device 843 on the cartridge 803. The communications interface 860 may also be configured to communicate with the base station 801 when the handheld unit is docked with the base station 801, and may also include charging ports that may be used to electrically connect a battery 851A of the handheld unit 802 with a charger. The battery 851A may, for example, provide a portable power source for the handheld unit 802.

Figure 13:
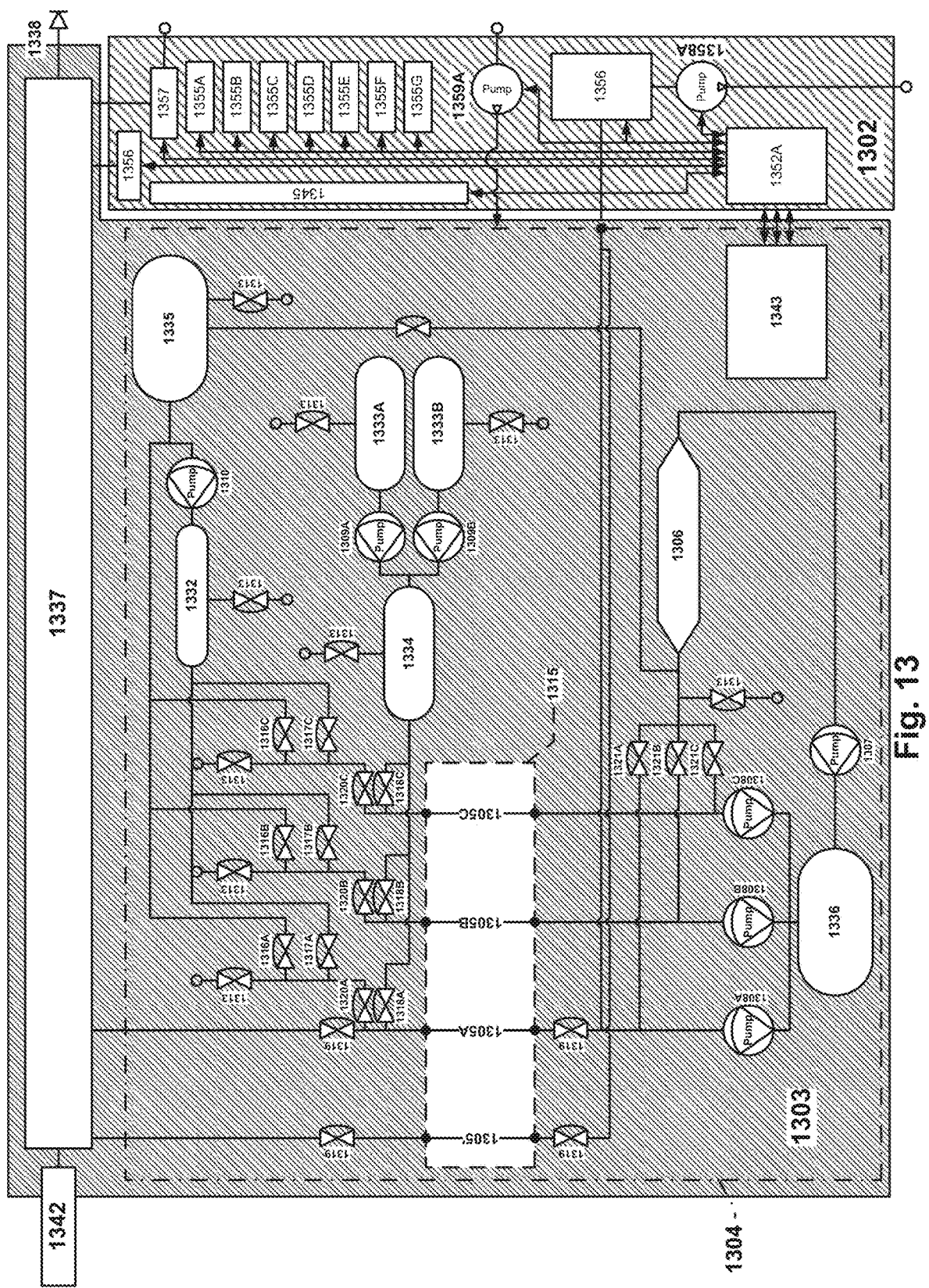
FIG. 13 is a schematic of an example disposable, or cartridge, and an example handheld unit.

FIG. 13 is a schematic of an example disposable, or cartridge, and an example handheld unit. In FIG. 13, a cartridge 1303 is docked to a handheld unit 1302. The cartridge 1303 includes a plenum 1337 that is fluidically connected with a mouthpiece 1342 and reaction channels 1305' and 1305A. The plenum 1337 is also fluidically connected, when the cartridge 1303 is installed in the handheld unit 1302, with a pressure sensor 1353 and a BAC sensor 1357. The cartridge 1303 may also have a microfluidic plate 1304 that includes a vacuum assist port that is fluidically interposed between a vacuum pump 1358A/flow sensor 1356 and the reaction channels 1305' and 1305A when the cartridge 1303 is installed in the handheld unit 1302. The microfluidic plate 1304 may also include a plurality of pressure control ports (not shown) that may interface with pressure pump 1359A.

The handheld unit 1302 may also include a controller 1352A that is communicatively connected with the pressure sensor 1353, the BAC sensor 1357, the flow sensor 1356, the pressurization pump 1359A, and the vacuum pump 1358A, as well as memory device 1343 on the cartridge 1303.

The microfluidic plate 1304 of the cartridge 1303 may optionally include a separate sub-module 1315 that includes the reaction channels 1305' and 1305A/B/C (in implementations without the sub-module 1315, such reaction channels may be provided directly in the microfluidic plate 1304). It is to be assumed that, unless otherwise indicated, the valves shown in FIG. 13 have a default state of "closed" or "sealed," but during sample collection, the isolation valves 1319 may be actuated to an "open" state, e.g., by applying negative pressure to a membrane at locations corresponding to the isolation valves 1319 within the microfluidic plate 1304 (see FIG. 11, for example). In conjunction with opening the isolation valves 1319, the vacuum pump 1358A may be operated to apply a negative pressure to the reaction channels 1305' and 1305A, thereby increasing the pressure differential between the reaction channels 1305' and 1305A and the plenum 1337. This causes a disproportionate amount of exhaled breath to be drawn into the reaction channels 1305' and 1305A (disproportionate in terms of cross-sectional area of the sample ports 1312 as compared with the cross-sectional areas of other ports or openings fluidically connected with the plenum 1337 through which the exhaled breath may pass).

The increased amount of breath sample that is diverted through the reaction channels 1305' and 1305A by virtue of the vacuum assist may allow for more breath constituents to be adsorbed (collected) on the walls of the reaction channels 1305' and 1305A from the same overall volume of exhaled breath as compared with systems that may not utilize a vacuum assist feature during sample collection. In the context of THC detection, the present inventors determined that a measured amount of about 1-10 picograms (pg) of THC in a breath sample of 0.5 liters was indicative of recent usage of THC, e.g., usage within the three hours prior to breath sample collection. As the amount of THC (or other analytes) to be measured is quite small compared to the amounts of "normal" breath constituents, e.g., air and/or carbon dioxide, a practically useful breath sampling system must be able to concentrate the breath constituents in a very small region while separating out the non-analyte breath constituents in order to facilitate sample collection and post-collection processing and measurement. For example, the 1-10 picogram range for THC discussed above may be approximately 1 billion times less than the amount of alcohol that may be present in the same volume of breath if the subject has recently been drinking.

There are at least two challenges that arise in collecting a breath sample for analyte detection. The first is pre-processing the breath sample to prepare it for analysis. The goal of such pre-processing is to alter or augment the analyte that is present in the breath sample so that it is in some way detectable, e.g., by binding a fluorescent or luminescent marker molecule to each molecule of analyte that is present. If there is a large volume, e.g., 0.5 liters, in which a relatively microscopic amount of analyte is present, whatever marker molecules are bound to or react with the analyte in such pre-processing must be present in sufficient quantity that the desired reaction between the analyte and the marker molecules occurs, from a statistical standpoint, for generally all analyte molecules (any analyte molecule that is "missed" during the pre-processing operations may fail to be detected during a later detection operation, thereby producing undesirable results). In a large volume, e.g., 0.5 liters, a large quantity of such marker molecules may be needed in order to ensure that all of the analyte molecules in the volume are bound to marker molecules (this may also depend on the amount of time allowed for the marker molecules to interact with the analyte molecules—the longer the two types of molecules are allowed to coexist within the same volume, the greater the chance that all of the analyte molecules will eventually encounter, and bind with, corresponding marker molecules—this, however, may require waiting for periods of time that are logistically undesirable, e.g., multiple minutes, or even hours). Another issue that may be encountered with marker binding to the analyte is that many markers remain in liquid phase at atmospheric conditions, making it difficult to adequately distribute the marker molecules throughout a gas volume.

Even if the above issues regarding pre-processing of the analyte within a large sample volume are addressed, the issue of then detecting the analyte within a large sample volume would persist. As most markers are visual in nature, e.g., giving off visible or detectable light, either on an ongoing basis driven by a chemical reaction or in response to some external excitation, e.g., photostimulation by a particular wavelength of light, any signal produced by a microscopic amount of analyte such as the amounts discussed above may be volumetrically diluted by the overall volume of the sample. Detectors that may be needed for measuring such volumetrically dilute signals may require very large apertures and extremely sensitive detection elements—such detectors may be beyond the limit of current technology or may be prohibitively expensive.

Accordingly, the present inventors determined that flowing the desired breath sample volume through reaction channels having particular geometries and dimensional characteristics would generally cause the analytes for which measurement is sought to be adsorbed onto walls of the reaction channels, thereby becoming trapped within the reaction channel, while most of the remainder of the breath sample exited the reaction channel. By sizing the reaction channels small enough, the analyte in question may be concentrated in a very small volume or volumes compared to the overall volume of breath that is flowed through those reaction channel collection volumes during sample collection. For example, in the microfluidic plate 804, the reaction channels 805' and 805A may be sized, for example, to be 1 mm by 0.6 mm in cross-section, e.g., each having a cross-sectional area of 0.6 mm$^2$, and having a nominal length of approximately 57 mm, thus having an overall volume of ~34 mm$^3$ (or 4); such channels are designed to each have at least approximately 0.5 L of exhaled breath sample flowed through them during breath sample collection. This has the effect of concentrating the analytes (which generally adsorb onto the walls of the reaction channels 1305' and 1305A) into a volume within each reaction channel 1305' and 1305A that is ~1450 times smaller than the approximately 0.5 liter breath sample that passes through each such channel. While some analyte may pass through the reaction channels 1305' and 1305A without adsorbing onto a wall surface of those reaction channels, at least a measurable amount of the analyte may nonetheless be captured within such reaction channels. Such less-than-perfect capture efficiency may simply be ignored or assumed to be zero, in some instances, or may be accounted for statistically, e.g., by assuming that some empirically derived quantity of analyte per unit volume of sample flowed through the reaction channels 1305' and/or 1305A will be lost and adjust for such loss accordingly (such as by multiplying the measured amount of analyte determined in later steps by a scaling factor based on such a loss ratio).

By capturing analyte directly within the reaction channels 1305' and 1305A in the microfluidic plate 1304, the analyte may be contained within a very small volume that lends itself to being filled with marker molecules in liquid phase or suspended in liquid media, thereby allowing every surface of the reaction channel 1305A onto which the analyte has adsorbed to be wetted with the marker molecule solution/liquid. This helps increase the chances that adsorbed analyte will react or bind with the marker during the pre-processing of the collected sample. Subsequent optical measurement of the bound marker may be limited to detecting an optical signal in a volume of fluid less than or equal to the volume of the reaction channel 1305A. For example, an optical detector may be used to determine the signal strength from a portion of the fluid in the reaction channel, and the resulting measurement may be scaled up based on the ratio of the volume of the portion of fluid measured as compared to the volume of the reaction channel as a whole from which it was obtained.

It will be understood that accurately detecting or measuring the amount of analyte in a breath sample may be dependent on a large number of different factors, including, but not limited to, the amount of breath sample collected (which may, in turn, be dependent on the duration and flow rate of the breath sample), the capture efficiency of the reaction channels, the amount of analyte that is needed to ensure that a measurable quantity of analyte, if present, is obtained, how difficult it is for a subject to provide an adequately sized sample, and various other factors.

In particular implementations, the cartridge may be specially adapted for obtaining adequately sized breath samples within a 60 to 90 second sampling interval for an average human male. In such implementations, the reaction channels may be sized so as to each have hydraulic diameters of 0.8 mm or less, 0.75 mm or less, 0.7 mm or less, 0.65 mm or less, or 0.6 mm or less and be approximately, e.g., within ±5 mm of, 40 mm, 50 mm, 60 mm, or 70 mm in length, although longer channel lengths may also be used. Reaction channels with such hydraulic diameters may result in capture efficiencies of 30%-40% (i.e., 30% to 40% of analyte within the breath sample flowed through such a reaction channel would be adsorbed onto the channel walls) or higher in reaction channels on the order of 60 mm in length. In implementations in which 0.5 liters or more of breath sample are to be passed through each reaction channel, the subject's lung capacity may limit the flow rate achievable through the reaction channels. For example, a typical adult male may be capable of exhaling with a pressure of approximately 1-2 psi. Such a pressure may result in only a small portion of each exhalation being diverted through the reaction channel, and it may take several minutes of exhaling, e.g., 5 minutes, to flow the desired volume (e.g., 0.5 liters) of breath sample through the microfluidic plate under such conditions. If breath sample flow through the reaction channels is augmented by providing a vacuum assist feature, however, much higher flow rates through the reaction channels may be achieved. For example, applying suction from a vacuum pump, e.g., one capable of drawing 7-9 psi of vacuum, to the reaction channels may significantly reduce the time needed to flow the desired volume through each reaction channel. For example, in an implementation having a reaction channel with a 0.7 mm hydraulic diameter, the volumetric flow rate achieved by a test subject through the reaction channel may be on the order of 0.1 L per minute without such a vacuum assist, but potentially as high as 0.7 L per minute with vacuum assist.

In developing the disclosed breath sampling system, the present inventors identified various parameters based on various relationships between a large number of variables that contribute to achieving a desired mass concentration (average density) of analyte within the volume of one or more reaction channels (which will also directly correlate with a desired quantity of analyte within the volume of each reaction channel). To start with, the concentration of analyte collected may be determined according to:

$$c = \frac{m}{nd^2 l}$$

In which c=desired, final concentration of analyte in reaction channels (e.g., picograms/µL, m=total mass of analyte collected in reaction channels (e.g., picograms), n=number of reaction channels, d=hydraulic diameter of each reaction channel (e.g., millimeters), and l=length of each reaction channel (e.g., millimeters) (this assumes that the reaction channels are of equal size and length; if not, then similar analyses may be performed with suitable modification). It will be understood that the example units used in this example are for discussion purposes only, and similar techniques may be used with units from other measurement systems as well, if desired, with appropriate conversions. The target concentration of analyte collected in the reaction channels may be determined, for example, based on the parameters of the detection and measurement protocol to be used, e.g., as determined by the sensitivity of the measurement device, the optical response of the biomarkers used, the analyte being detected, and various other factors.

In order to determine how much analyte mass will be collected in the reaction channels, various factors may come into play, including, for example: what the mass concentration of analyte is in the subject's exhaled breath, what the exhaled breath flow rate is through the reaction channels, what the dimensions of the reaction channels are, the total duration of breath sample flow through the reaction channels, and the diffusion coefficient of the analyte in exhaled breath. In some instances, there may be little flexibility in these factors, e.g., the mass concentration of the analyte in the subject's exhaled breath is the parameter of which quantification is ultimately sought, and there is therefore no flexibility in changing it—it is what it is. In another example, the diffusion coefficient will be determined based on what diffusion coefficient is for the analyte in exhaled breath (or, for example, atmospheric air). In other instances, there may be ergonomic factors at play, e.g., the duration of breath sample flow may largely be governed by a desired maximum duration for the sampling process—sampling that lasts too long may be physically demanding for some test subjects, and may result in the sampling and analysis process being perceived as too time-consuming in terms of test-subject's and the tester's time. Other parameters, such as the exhaled breath flow rate through the reaction channels and the dimensions of the reaction channels, may offer more flexibility in terms of tuning the achieved collected analyte concentration in the reaction channels.

By way of further example, the analyte mass exhaled from the test subject may be quantified by:

$$m_{ex} = c_{ex} \cdot n \cdot Q \cdot t_{ex}$$

where $m_{ex}$=total mass of exhaled analyte that passes through reaction channels (e.g., picograms), $c_{ex}$=mass concentration of exhaled analyte per unit volume of exhaled breath (e.g., picograms/μL), Q=volumetric flow rate through each reaction channel (e.g., μL/s) (assumed to be equal for each reaction channel here; see discussion above for situations in which reaction channels are not dimensionally equivalent), $t_{ex}$=duration of exhaled breath(s) (e.g., seconds) (does not include inhaling). Summarized more generally, the mass of analyte that is exhaled through the reaction channels is equal to the product of the total flow rate of exhaled breath through the reaction channels times the exhalation time (to determine total volume flowed through the reaction channels) multiplied by the concentration of the analyte in the exhaled breath.

The present inventors also conceived of a dimensionless constant, referred to herein as the "Hound" number, quantified by:

$$H \propto \left(\frac{\sqrt{2Dt}}{\frac{d_1}{2}}\right)^2 + \left(\frac{\sqrt{2Dt}}{\frac{d_2}{2}}\right)^2 \cong 2 \cdot \left(\frac{\sqrt{2Dt}}{\frac{d}{2}}\right)^2$$

where D=diffusion coefficient (e.g., square millimeters/second), t=residence time for breath sample in reaction channel (e.g., seconds), $d_1$=width of each reaction channel, $d_2$=height of each reaction channel, and d=hydraulic diameter of each reaction channel (e.g., all in millimeters). The Hound number, more succinctly, may be thought of as the dimensionless ratio of the mean diffusion distance to half the width and height of the reaction channel. As a simplification, the distinct height and width variables $d_1$ and $d_2$ may be approximated using the hydraulic diameter d of the reaction channels. This simplification is propagated into the discussion below, although it will be recognized that a more exact calculation may be obtained if this simplification is avoided. However, it should also be recognized that the more exact calculation involving $d_1$ and $d_2$ may be applicable only to rectangular-cross-section reaction channels; the hydraulic diameter may therefore be a more flexible parameter to use since it may be easily determined for a wide variety of different channel cross-sections.

The total mass of analyte actually collected in the reaction channel(s) may be determined using:

$$m \propto 2K \cdot \frac{\sqrt{2Dt}}{\frac{d}{2}} \cdot m_{ex}$$

in which K=collection efficiency (dimensionless factor) relating the amount of analyte that is actually captured by each reaction channel to the total amount of analyte flowing through that reaction channel. Put more simply, the total mass of analyte actually collected in the reaction channel(s) is the product of the collection efficiency times the total mass of analyte exhaled through the reaction channel(s).

The residence time of each breath sample within each reaction channel (assuming a constant flow rate) may be determined according to:

$$t = \frac{d^2 l}{Q}$$

This relationship, in turn, may be substituted into the relationship for total mass analyte actually collected in the reaction channels set forth above to arrive at the following restated relationship for total mass analyte actually collected in the reaction channels:

$$m \propto 2K \cdot \frac{\sqrt{2D \frac{d^2 l}{Q}}}{\frac{d}{2}} \cdot m_{ex} \propto 4K \cdot \sqrt{2D \frac{l}{Q}} \cdot m_{ex}$$

The total mass of analyte actually collected in the reaction channel(s) may be rewritten to substitute out $m_{ex}$ for the relationship for the total mass of analyte exhaled set forth earlier to yield:

$$m \propto 4K \cdot \sqrt{2D \frac{l}{Q}} \cdot c_{ex} \cdot n \cdot Q \cdot t_{ex} \propto 4K \cdot \sqrt{2DlQ} \cdot n \cdot c_{ex} \cdot t_{ex}$$

The above expression may be substituted into the expression for the concentration of analyte collected set forth earlier to yield:

$$c \propto \frac{4K \cdot \sqrt{2DlQ} \cdot n \cdot c_{ex} \cdot t_{ex}}{nd^2 l} \propto \frac{4K}{d^2} \sqrt{\frac{2DQ}{l}} \cdot c_{ex} \cdot t_{ex}$$

This relationship may be further simplified using $Q_p=nQ$ (where $Q_p$=total volumetric flow rate (e.g., µL/second) out of all of the reaction channels; in systems with vacuum assist, this flow rate may be equivalent to the flow rate through the vacuum pump) and $V_d=nd^2l$ (where $V_d$=total volume (e.g., µL) of the reaction channels) to yield:

$$c \propto \frac{4K}{d} \cdot \sqrt{\frac{2DQ_p}{d^2nl}} \, c_{ex}t_{ex} \propto \frac{4K}{d} \cdot \sqrt{\frac{2DQ_p}{V_d}} \, c_{ex}t_{ex}$$

With some rearrangement of terms, the concentration of analyte actually collected in the reaction channel(s) may be thus be expressed by:

$$c \propto 8Kc_{ex}\left[\underbrace{\left(\frac{Q_p t_{ex}}{d^2 l}\right)}_{\substack{\text{total number of} \\ \text{channel passes}}}\underbrace{\left(\frac{d^2 l}{V_d}\right)}_{\substack{i \\ \text{total number} \\ \text{of channels}}}\underbrace{\left(\frac{t_{ex}}{d^2/2D}\right)}_{\substack{\text{exhale time} \\ \text{diffusion time}}}\right]^{1/2} \propto$$

$$8Kc_{ex}\left[\frac{\text{\# of passes}}{\text{channel}} \cdot \frac{\text{Exhale time}}{\text{Diffusion time}}\right]^{1/2}$$

As can be seen, the concentration of analyte collected in the reaction channels may be generally controlled by the three terms within the square root demarcated above. The first term represents the total number of channel passes, e.g., the total number of times the volume of breath sample within each reaction channel is replaced with a new volume of breath sample. The second term represents the inverse of the total number of channels. The third term represents the exhalation time divided by the diffusion time.

In view of the above, it will be apparent that the various factors governing analyte concentration in the reaction channels may be grouped into three categories. In the first category are variables that are generally unable to be changed, e.g., variables such as $c_{ex}$ and D. For $c_{ex}$, such a variable is dependent on the subject and the level of analyte in the subject's breath. From a practical standpoint, $c_{ex}$ may be set to the lowest expected concentration of the analyte in a person's breath that may need to be detectable in order to achieve diagnostic or evidentiary requirements governing the analysis. Such $c_{ex}$ values may, for example, be determined empirically using laboratory equipment such as a mass spectrometer (i.e., performed under conditions in which all or nearly all of the analyte in a given breath sample volume may actually be captured and analyzed—conditions that are, in the present state of the art, not practical to replicate in a handheld or portable field-measurement unit). For D, the diffusion coefficient may be determined based on the composition of the specific analyte being collected and the exhaled breath. Thus, once a target analyte has been selected, the diffusion coefficient may essentially be viewed as static.

In the second category are, for example, variables that are more flexibly alterable. For example, the total volumetric flow rate $Q_p$ may, from a practical standpoint, have little in the way of flexibility in the microfluidic context if solely dependent on unassisted human breath, as the pressure differential achievable by an unaided human may only be on the order of 1-2 psi. As a result, the flow rates achievable with unaided subject breathing may have little in the way of flexibility. However, if vacuum assist is used, the total volumetric flow rate $Q_p$ may be greatly enhanced over that achievable with unaided human breath, e.g., up to 7-8 times higher (based on a theoretical maximum pressure differential of 14.7 psi (atmospheric)+2 psi (contributed by subject lung pressure) for a vacuum assist that draws a complete vacuum, as opposed to a theoretical maximum pressure differential of ~2 psi relative to atmospheric for human breath without vacuum assist). The hydraulic diameter and length, and thus the volumes, of the reaction channels may be tuned as well.

In the last category are factors like collection efficiency K, as well as potentially various constants (some of which are omitted in the above equations in the interest of simplicity, e.g., n is omitted in calculations relating hydraulic diameter to area or volume) that may act to linearly scale the analyte concentration achieved. The collection efficiency may be calculated or may be assigned a value based, for example, on empirical data. For example, for a reaction channel of a given hydraulic diameter, a known quantity of analyte may be passed through and the amount of the analyte that exits the reaction channel may be measured to determine how efficiently the reaction channel of that hydraulic diameter collected the analyte.

The present inventors identified the reaction channel dimensions and the total volumetric flow rate through the reaction channels as providing the most effective way of adjusting the concentration of analyte collected within the reaction channels for a given sampling duration. Absent external constraints, the sampling duration may, in theory, be extended for as long as is necessary in order to obtain a desired concentration of analyte. However, for a breath sampling and analysis system capable of both capturing a breath sample and then performing analysis of that breath sample in the field, it may be desirable to limit the sampling duration to 1 to 2 minutes, e.g., 60 seconds, 90 seconds, or 120 seconds, or less. Such sampling durations may be determined based on a variety of factors, e.g., operator fatigue (assuming that the operator needs to hold/support a handheld unit while a subject breathes into it), overall time necessary to obtain a breath sample and complete the analysis, operator and subject patience, and various other factors. Thus, the present inventors focused on reaction channels that would provide desired concentrations of analyte within the reaction channels for exhalation durations of approximately 60 to 90 seconds or, in some cases, 60 seconds.

As discussed earlier, $c_{ex}$ is not a tunable variable, D is set based on what the analyte being measured is, and $t_{ex}$ is, under the assumptions set for above, fixed at a value such as 60 seconds. Per the last relationship set forth in the paragraphs above, this leaves K, $Q_p$, $V_d$, d, and l as variables in which there is a realistic potential for being able to tune the analyte concentration c to a desired level. Generally speaking, reducing d and l to as low a value as possible will cause $V_d$ to shrink to an infinitesimal volume, thereby achieving the desired concentration of analyte in a vanishingly short period of time. However, $V_d$ may generally be set to a level that is largely determined by the limitations of other equipment used, e.g., by the minimum volume needed in order to obtain an optical measurement using an optical measurement device. In some implementations, this may be approximately 15λ (based on a typical minimum sample volume needed for many commercially available optical measurement devices), although such volumes may be increased depending on the specific optical detector used, the amount of fluid dead volume that may be expected in moving the sample fluid from the reaction chamber to the optical measurement chamber, and/or any potential losses due to pumping efficiency or other factors. For example, $V_d$ of between about 15 µL and 35 µL, 15 µL and 45 µL, 15 µL and 55 µL, 15 µL and 65 µL, 15 µL and 75 µL, and 15 µL and 85 µL are some example volumes that may be used, although increasing $V_d$ will generally increase the amount of time needed to obtain the desired analyte concentration in that $V_d$.

In view of the above, K, $Q_p$, and d (1 may be factored out) represent the variables most useful for tuning c. Of these, only $Q_p$ and d are readily and easily adjusted. $Q_p$, as discussed earlier, may be easily adjusted using a vacuum assist feature, although the ability to do so is atmospherically limited, e.g., the analyte concentration may only be increased up to about 8× more than is achievable without vacuum assist. This leaves d, in which decreasing d may generally cause the analyte concentration in the reaction channels to increase. While d could, in theory, be reduced to infinitesimally small amounts, practical considerations such as flow resistance, the possibility of blockage, the corresponding increase in length needed in l in order to maintain an acceptable $V_d$, manufacturing tolerances, and so forth may limit the degree to which d may be reduced. In the context of THC detection systems, the present inventors determined that reaction channels with hydraulic diameters between about 0.1 mm and 1 mm may be effective in collecting a desired (and detectable) concentration of analyte within each reaction channel within a 60 second sampling window and with a vacuum assist feature provided (e.g., drawing down to 5-7 psi or lower). In some implementations, corresponding reaction channel lengths (the length of the reaction channels in between the isolation valves for each reaction channel) were determined to range between about 15 µL/d² and 45 µL/d².

The calculations and analysis discussed above assume straight reaction channels. However, additional implementations may utilize other reaction channel geometries that follow zigzag, spiral, wave, or other path types to capture particular kinds of particles more efficiently. Moreover, the reaction channel geometries may be further customized based on the size, shape and form of the analyte (molecule, particle, etc.). The discussion above focuses on examples that may be particularly effective at capturing molecular THC (although such examples may also be effective at capturing other types of analytes as well) through molecular diffusion. However, for aerosolized THC where the THC molecule may be in stuck to lung-lining surfactant or water in a vapor phase, the analyte may effectively be much larger than a purely molecular analyte (by virtue of being attached to a much large molecule or molecules), in which case curved, spiral, or otherwise non-linear reaction channels may more effectively capture the analyte due to inertial effects, e.g., a spiral reaction channel may, in effect, centrifuge the analyte towards the walls of the reaction channel, thereby increasing the chance of adsorption or binding of the analyte. In some implementations, multiple reaction channels of different designs, each optimized or designed to capture a different analyte with high efficiency, may be included in a single microfluidic plate so as to allow the different analytes (or different forms of the same analyte, e.g., molecular THC and aerosolized THC, to be captured from the same breath sample. In some implementations, a large number of different analytes may be captured on a single microfluidic plate using different reaction channels that are each tuned to most efficiently capture a different analyte; such examples may allow for a large panel of measurements of different analytes to be made, thereby allowing for a variety of different potential diseases to be identified from a single breath sample. It will be understood as well that in systems that utilize a separate sub-module to house the reaction channels, the same underlying main portion of the microfluidic plate may be interfaced with any of a variety of different sub-modules, each of which may have reaction channel geometries that are tuned for a particular type of analyte, as discussed above.

In systems with vacuum assist, the controller 1352A may monitor data from the pressure sensor 1353 to determine when a breath sample is being collected, e.g., when data from the pressure sensor 1353 indicates a positive pressure above a particular threshold (and possibly below a second particular threshold), and may control operation of the vacuum assist based on such data. Such thresholds may be set to be consistent with pressures experienced within the plenum 1337 during breath sample collection. For example, if the pressure sensor data indicates that the gauge pressure within the plenum 1337 is 0.03 psi (0.2 kPa) or higher, this may be indicative that a test subject is exhaling into the cartridge and that a sample is being collected. In some implementations, too high a pressure may be indicative of misuse of the system, e.g., if more than 0.6 psi gauge pressure (4 kPa) is observed within the plenum 1337, this may be indicative of an attempt to misuse the system. In systems with vacuum assist, the controller 1352A may control the vacuum pump 1358A and/or other components so that the vacuum pump 1358A is only active (or only applying a vacuum to the reaction channels) when the data from the pressure sensor indicates that a breath sample is being collected, as discussed above. In some implementations, such vacuum pump control may include shutting off the vacuum pump (or causing vacuum assist to otherwise not be applied to the microfluidic plate) when the pressure measured by the pressure sensor drops below a predetermined threshold associated with breath sample collection. In some further implementations, the vacuum pump may also be turned off (or vacuum therefrom caused not to be applied to the microfluidic plate) when the pressure measured by the pressure sensor exceeds a different predetermined threshold, such as 0.6 psi gauge pressure (or any pressure selected from the range of 0.5 to 2.0 psi gauge) or the like. In implementations with pressure monitoring, such vacuum assist control may also be accompanied by the generation of auditory and/or graphical cues, e.g., if the pressure falls outside of the thresholds associated with valid breath sample collection, warning tones and/or lights may be caused to activate, or a verbal or visual cue, such as auditory or visual messages such as "blow harder" or "blow less" may be provided. In the case of an over-pressurization of the plenum, the auditory or visual feedback may be provided, but the vacuum assist may be left functional so that the sample continues to be drawn (in an overpressure scenario, the main risk may not be to sample collection, but overexertion of the subject, so the breath sample collection may continue, but the subject may be cautioned to breath less aggressively so as to avoid potentially hyperventilating or otherwise suffering adverse effects. Such implementations may thus avoid having the vacuum assist operating while the subject, for example, is not exhaling into the plenum 1337. This avoids the possibility that negative pressure may develop within the plenum 1337, which could potentially draw ambient air into the plenum 1337 through the flow restrictor 1338, thereby introducing undesirable contaminants into the reaction channels. In such implementations, the vacuum assist, e.g., vacuum pump 1358A, may only be activated by the controller 1352A during periods of time when the pressure data from the pressure gauge is above the threshold indicating that a subject is exhaling into the plenum 1337. Thus, when a subject pauses to inhale, for example, the vacuum assist may be temporarily deactivated and only reactivated once the subject starts to exhale into the plenum 1337 again. As an alternative to activating/deactivating the vacuum pump 1358A, some implementations may simply keep the vacuum pump 1358 active and may instead incorporate a bypass valve that may be controlled to divert suction from the vacuum pump from the reaction channels to a bleeder port or other ambient air source when the vacuum assist is to not be applied to the reaction channels.

In particular, systems including vacuum assist features may, in some implementations, be specifically configured to only initiate vacuum assist after the isolation valves 1319 have been actuated into an "open" state. This avoids a scenario in which the vacuum assist may interfere with the operation of diaphragm valves used as isolation valves 1319. For example, in order to open such isolation valves 1319, a vacuum may be applied to the diaphragm membrane on the side of the membrane opposite the reaction channels, thereby pulling the membrane away from the reaction channels and allowing fluid flow into or out of the reaction channels. However, if the reaction channels are themselves under vacuum due to the vacuum assist when actuation of the isolation valves 1319 is attempted, then the vacuum applied to the isolation valves 1319 to actuate them may have no effect, leaving the isolation valves 1319 in the closed state. Thus, the controller 1352A may be specifically configured in some vacuum assist implementations to only enable the vacuum assist feature after the isolation valves have been opened.

In some implementations, the handheld unit 1302 may also include a heater component 1345, e.g., a thermoelectric cooler (one side of which may be the "hot" side and the other the "cold"; the hot side may be used as a heater) or a resistive heater, that may be positioned to apply heat to the microfluidic plate to prevent freezing within the reaction channels. The active heating area of the heater component 1345 may be at least coextensive, or nearly coextensive, with the area occupied by the reaction channels 1305' and 1305A and the vacuum assist flow path(s) within the microfluidic plate 1304 so that the reaction channels 1305' and 1305A, and the vacuum assist flow path(s) may be heated to prevent condensate from breath sample flowed therethrough from freezing and potentially clogging or obstructing the reaction channels and/or vacuum assist flow path. In implementations with the heater component 1345, the controller 1352A may be configured to activate the heater component 1345 responsive, for example, to data from a temperature sensor, e.g., temperature sensor 1355A, indicating that ambient temperatures are below a threshold amount, e.g., below zero Celsius, and/or data that indicates that a breath sample is about to be obtained, e.g., if the controller 1352A determines that the cartridge 1303 has been docked to the handheld unit 1302, or that the handheld unit 1302 has been turned on or placed into a sample collection mode.

Returning to FIG. 13, once the flow sensor 1356 indicates that a sufficient quantity of breath sample has flowed through the reaction channels 1305' and 1305A, the vacuum pump 1358A may be caused by the controller 1352A to stop supplying negative pressure to the vacuum assist port of the cartridge 1303, and the pressurization pump 1359A may be caused by the controller 1352A to apply positive pressure to the isolation valves 1319, thereby sealing whatever analytes and gas remain within the reaction channels 1305' and 1305A into those reaction channels 1305' and 1305A. In this example, the reaction channel 1305' is intended for long-term sample preservation, e.g., for evidentiary purposes or for later analysis in a fully equipped laboratory; the sample that is collected in the reaction channel 1305' is thus left alone after collection and is not subjected to any of the subsequent processing that the sample collected in reaction channel 1305' is subjected to, as discussed in more detail below. It will be understood that some implementations may omit the reaction channel 1305' or may, for example, include more than one instance of the reaction channel 1305A, allowing for multiple tests of the same sample, which may provide additional confidence in the measurement result.

In implementations that include additional breath sampling systems, e.g., such as the BAC sensor 1357, a portion of the breath sample passing through the plenum 1337 may be diverted to such additional breath sampling systems. In this implementation, the BAC sensor 1357 may generate a BAC reading that is then caused by the controller 1352A to be stored in the memory device 1343.

Additionally, as discussed earlier, the controller 1352A may monitor data from the pressure sensor 1353, the flow sensor 1356, a temperature sensor 1355A, a humidity sensor 1355B, and so forth and to store such data, or data derived therefrom, on the memory device 1343. The handheld unit 1302 may also include additional components that may produce data, or data derived from such data, that may be stored on the memory device 1343. For example the handheld unit 1302 may include an internal clock 1355C that may provide date and time information associated with a particular breath sample collection event, a global positioning system (GPS) receiver 1355D that may provide date, time, and location information associated with a particular breath sample collection event, a fingerprint or other biometric sensor 1355E that may provide biometric information about a subject in associated with a breath sample collection event involving that subject, and/or an imaging sensor 1355F that may generate video or image data regarding a breath sample collection event (such as video of the person blowing into the mouthpiece 1342). Any or all of such information may be stored on the memory device 1343 for later retrieval. It will be understood that some such information may be obtained from an external device that is communicatively coupled with the handheld unit. For example, the handheld unit may include a wireless communications interface 1355G, e.g., Bluetooth, that may be configured to communicate with a cell phone or smartphone having a camera, GPS device, and fingerprint sensor. In such instances, the cell phone or smartphone may have functionality, e.g., an app, that allows the handheld unit 1302 to obtain information relating to a breath sample collection event to be collected from the cell phone or smartphone, e.g., the GPS location of the cell phone or smartphone at the time of sample collection may be used as the GPS location of the handheld unit at that same time, and images or fingerprints captured by the smartphone or cell phone at that time, or immediately before or after sample collection occurs, may be obtained by the handheld unit 1302 and stored on the storage device in association with that sample collection event.

The remainder of FIG. 13 will be discussed later in the context of interactions with a base station.

Figure 14:
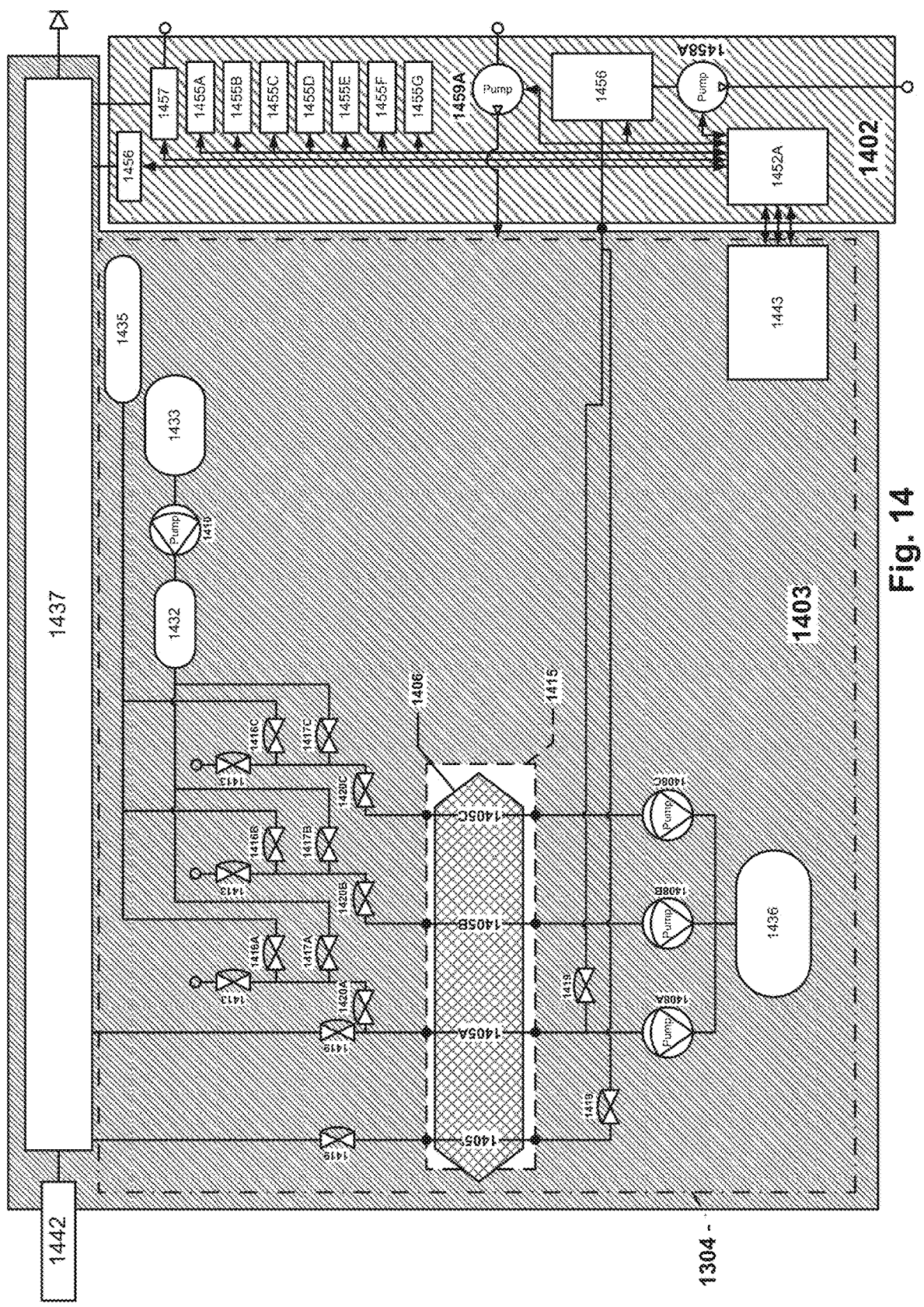
FIG. 14 is a schematic of another example disposable, or cartridge, and the example handheld unit.

FIG. 14 is a schematic of another example disposable, or cartridge, and the example handheld unit. In the implementation of FIG. 14, the components with similar last two digits in their callouts to components in FIG. 13 may be generally similar in purpose and operation as those corresponding elements in FIG. 13, unless described otherwise below.

The system of FIG. 14 may include a handheld unit 1402 that is generally the same as the handheld unit 1302. The cartridge 1403 may also be similar to the cartridge 1303, although the microfluidic plate 1404 may differ in several respects from the microfluidic plate 1304. Additionally, the reagents and liquids stored within the cartridge 1403 may differ from those discussed above in the discussion of the cartridge 1303.

The microfluidic plate 1404 may be designed for use with, for example, a diazofunctionalized fluorophore, e.g., rhodamine-123, that may be stored within an indicator reservoir 1432 in a dried, powderized form or in solution. Other indicators may be used depending on the analyte being sought; diazofunctionalized fluorophore indicators such as the rhodamine-123 indicator noted above may be useful for detecting THC, however). When analysis is to be performed (which would occur when the cartridge 1403 is interfaced with a base station instead of the handheld unit 1402), an indicator solvent may be flowed into the indicator reservoir 1432 from an indicator solvent reservoir 1433 by actuating an indicator pump 1410. While the indicator is dissolving in the indicator solvent in the indicator reservoir 1432, the reaction channel 1405A may be flushed with a wash fluid from the wash reservoir 1435 by actuating the reaction channel pumps 1408A/B/C and opening the reaction channel valves 1420A/B/C and the wash fluid valves 1416A/B/C. In this particular implementation, the reaction channels 1405A/B/C and 1405' may have antibodies immobilized on the interior surfaces thereof that are specific to the analyte of interest, e.g., THC in this example. Thus, when a breath sample is flowed through the reaction channels 1405A and 1405', the analytes specific to the antibodies may bind to the immobilized antibodies and remain fixed in plate within those reaction channels. Similarly, when known control amounts of the analytes are placed in the reaction channels 1405B and 1405C, those control amounts may also bind to the immobilized antibodies in those reaction channels as well. Thus, when the reaction channels 1405A/B/C are flushed in the wash operation, the analyte will remain behind since it is immobilized by being bound to the immobilized antibody. Any other contaminants, e.g., tobacco smoke particulates, saliva, etc., will be generally washed away, however.

After sufficient time has elapsed for the indicator to dissolve within the indicator solvent and after the wash operation has completed, the indicator solution may be flowed into the reaction channels 1405A/B/C, where it may react with whatever analyte is present in those reaction channels 1405A/B/C to produce, for example, a fluorescent adduct that may fluoresce when stimulated with a particular wavelength of light. After the indicator solution is allowed to incubate in the reaction channels 1405A/B/C for a sufficient period of time, the indicator solution in each reaction channel 1405A/B/C may be separately stimulated with excitation light and the resulting emitted light may be measured to determine a relative quantity of adduct, and thus analyte, present in that reaction channel. The amount of analyte in the breath sample may be determined by interpolating between known amounts of the control amounts of analyte in the reaction channels 1405B and 1405C based on the relative fluorescence intensity of the breath sample indicator and that measured for the indicator for the control amounts.

Figure 15:
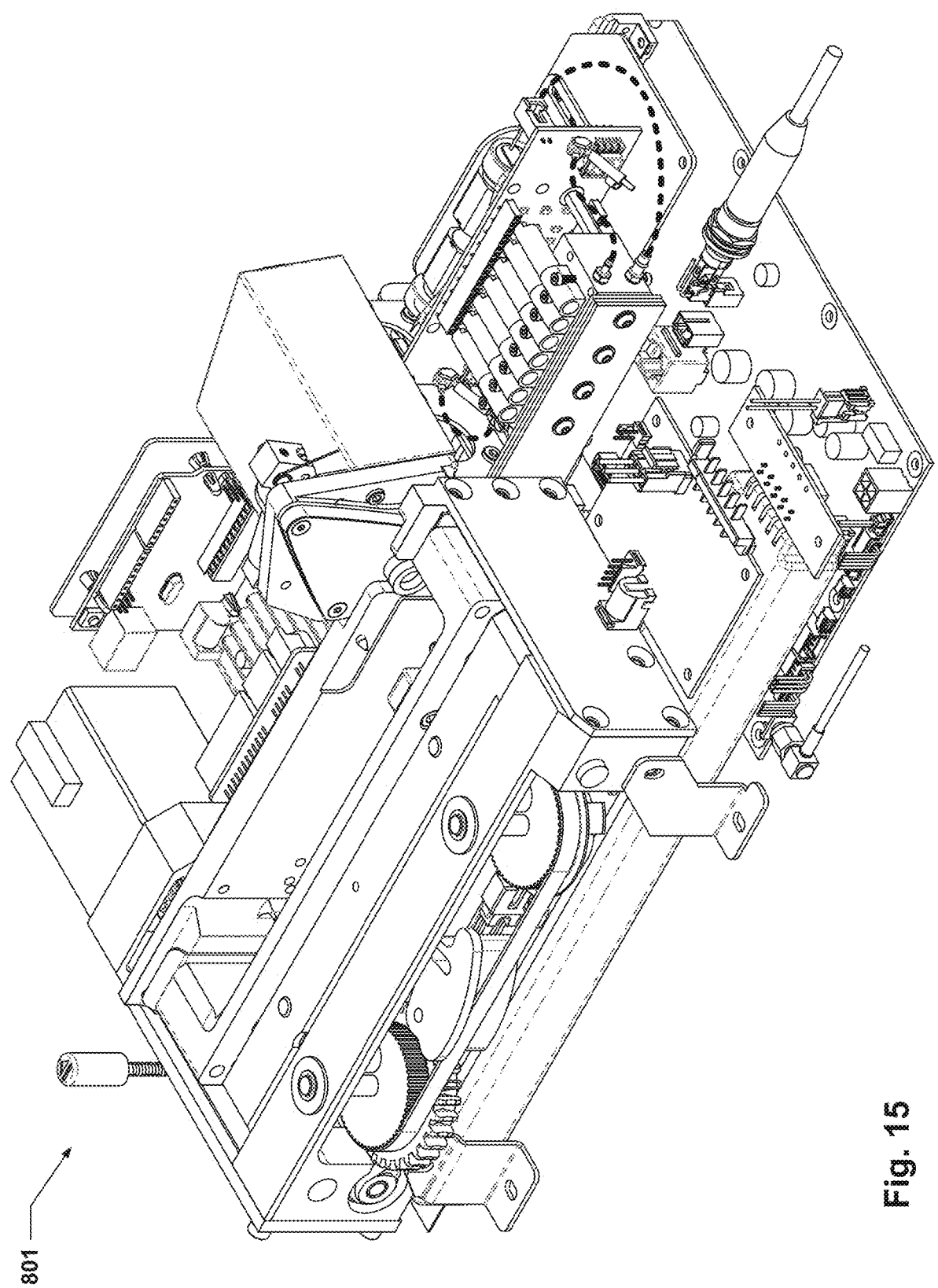
FIG. 15 depicts an example base station of the example breath sampling and analysis system of FIG. 8.
Figure 16:
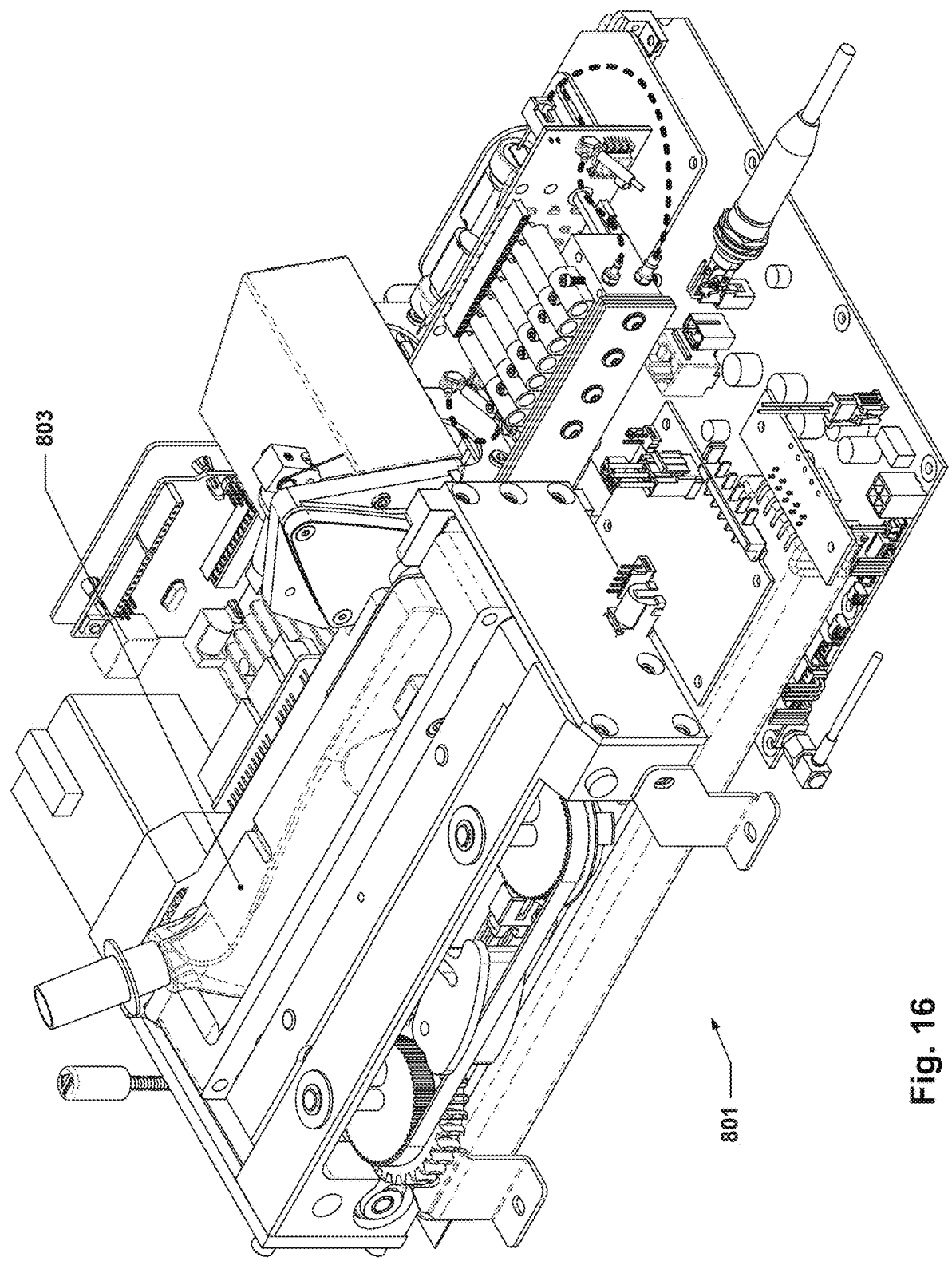
FIG. 16 depicts the example base station of FIG. 15 with the example disposable or cartridge of FIG. 9.
Figure 17:
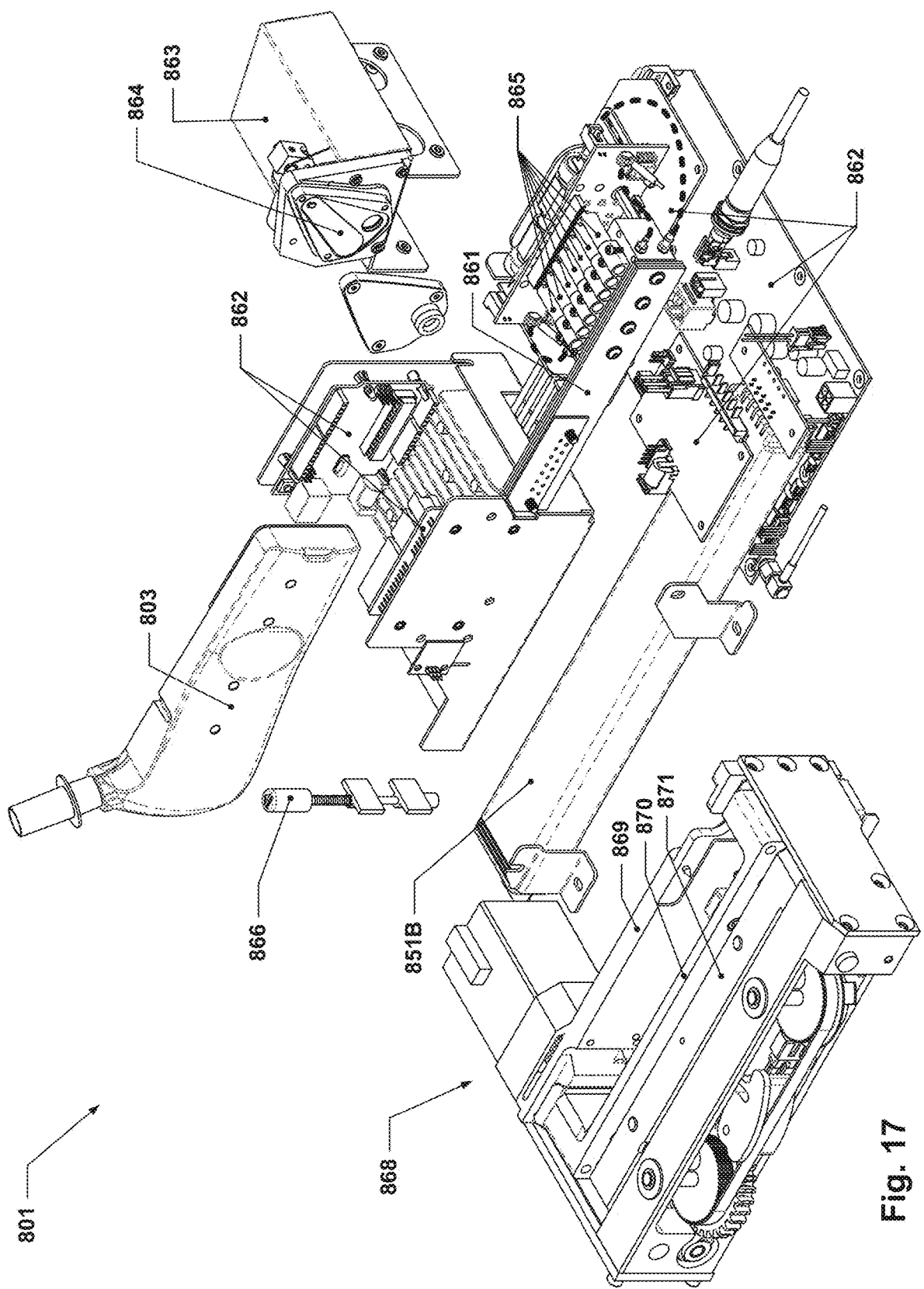
FIG. 17 depicts an exploded view of the example base station of FIG. 16.

FIG. 15 depicts an example base station of the example breath sampling and analysis system of FIG. 8. FIG. 16 depicts the example base station of FIG. 15 with the example disposable or cartridge of FIG. 9. FIG. 17 depicts an exploded view of the example base station of FIG. 16.

The depicted example base station 801 is shown without cabling, wires, external housing, and various other components unnecessary for this discussion. As can be seen from FIGS. 15 and 16, the base station 801 may include a slot that may receive the cartridge 1303, as shown in FIG. 16. Such a slot may be housed, for example, beneath a fold-down door (see system 800 in FIG. 8, in which the door is shown in an open state with the cartridge installed) that may be closed to help optically isolate the cartridge 1303 from stray environmental light. The base station 1301 may have multiple subsystems and components that may act in concert to perform analysis and measurement operations. For example, an actuation mechanism 868 may be provided to receive and prepare the cartridge 803 for analysis, an eject button 866 may be provided to allow for a user to initiate cartridge ejection and retrieval, a battery 851B may be provided to allow the base station 801 to operate independent of an external power source for limited periods of time, e.g., in the field, and one or more control boards 862 may be provided with electronics, e.g., a processor or processors, signal conditioners, driver circuits, communications interfaces, power conditioners, memory, etc., that provide control functionality for enabling the control of the various other subsystems in the base station 801. The base station may also include an optical measurement module 863, which may be equipped with an optional shutter mechanism 864 and which may be located so as to be able to measure an optically detectable signal arising from the cartridge 803, e.g., such as may be produced by marker-bound analytes trapped within the cartridge 803. The base station 801 may also include a pneumatic control system that may include a pressurization pump 8596 and a vacuum pump 858B that may provide positive and negative pressure, respectively, to a plurality of individually controllable valves 865 that may each be fluidically connected to a different flow path in a pneumatic transfer manifold; each such flow path may terminate in a pneumatic port that may interface with a corresponding pneumatic control port 814 on the cartridge 803 when the cartridge 803 is loaded into the base station 801.

When the base station 801 is used to process a captured breath sample, the actuation mechanism 868 may be among the first systems to be activated. The cartridge 803 (containing a sample) may be inserted into the actuation mechanism 868 in between a heat spreader plate 869 and a cartridge clamp 870; the cartridge clamp 870 and a blister compression frame 871 may both be semi-independently movable relative to the heat spreader plate 869, as will be explained in more detail later.

Figure 18:
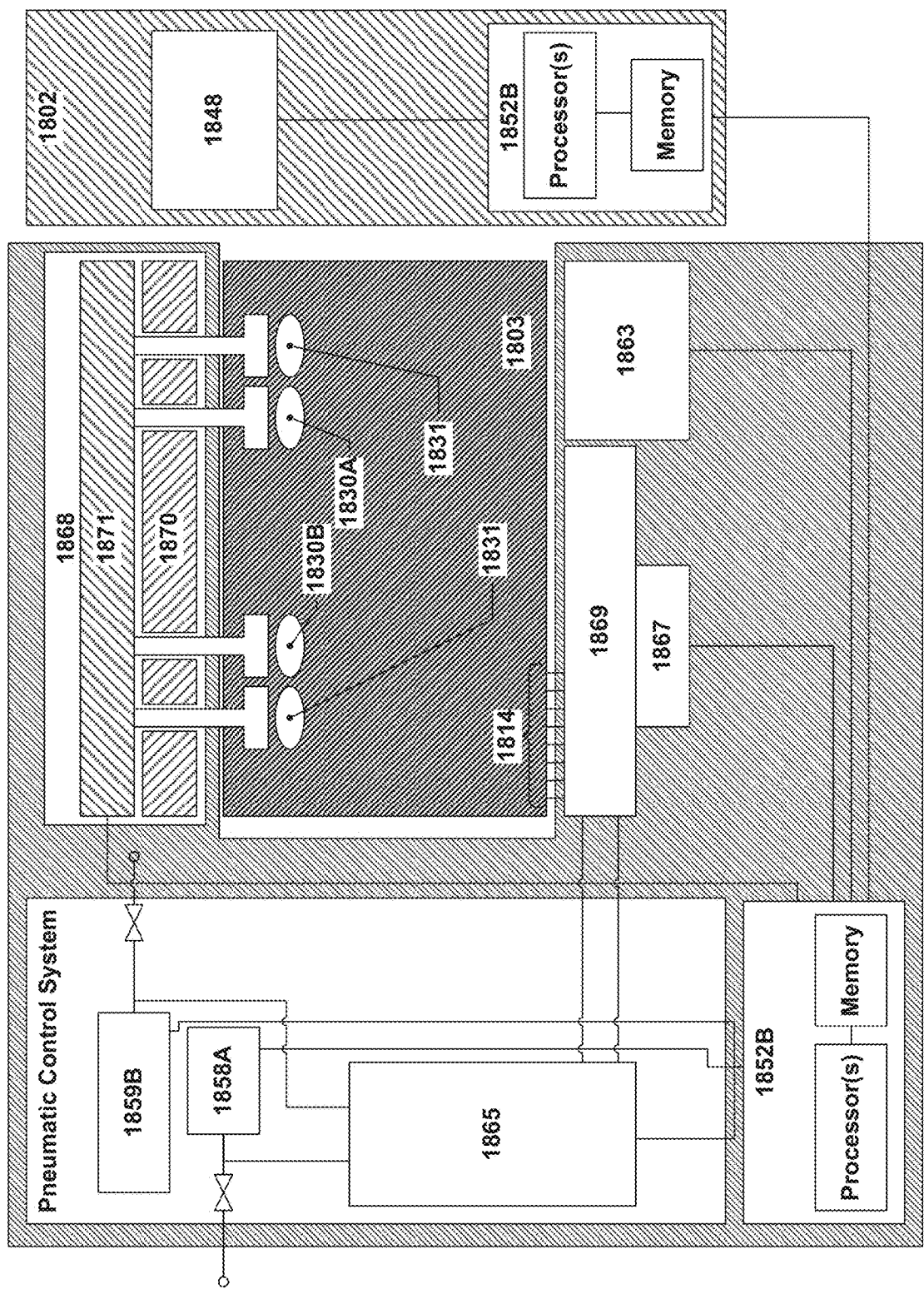
FIG. 18 is a schematic of an example disposable, or cartridge, and an example base station.

FIG. 18 is a schematic of an example disposable, or cartridge, and an example base station. The example base station 1801 may be configured to receive a cartridge 1803 and a handheld unit 1802, which may both be removably inserted into or docked with the base station 1801. The handheld unit 1802 may be similar to the handheld units discussed earlier in this disclosure, e.g., the handheld units 802, 1302, or 1402, and the cartridge 1803 may be similar to the cartridges discussed earlier in this disclosure, e.g., the cartridges 803, 1303, or 1403. The base station 1801 may include, for example, a controller 1852B that, like the controller 1852A of the handheld unit 1802, includes one or more processors, a memory or memories, communications interfaces, and other electronic components configured to control various aspects of the operation of the base station 1801. The base station 1801 may include an optical measurement module 1863 that may be communicatively coupled with the controller 1852B and positioned so as to obtain optical signal measurements from one or more locations of the cartridge 1803. In some implementations, the cartridge 1803 may have a single optical measurement site and the optical measurement module 1863 may be fixed in space in a position that aligns with this optical measurement site when the cartridge 1803 is loaded into the base station 1801. In other implementations, the cartridge 1803 may include multiple optical measurement sites and one or both of the actuation mechanism 1868 and/or the optical measurement module 1863 may be configured to translate relative to the other to allow the optical measurement module to obtain a separate measurement from each optical measurement site. In such implementations, additional hardware, e.g., linear movement actuators, rotational indexers, or the like, may be provided to allow the components in question to be repositioned relative to each other to allow the optical measurement module 1863 to obtain measurements from each optical measurement site. In yet other implementations, each measurement site may have its own dedicated optical measurement module associated therewith.

The base station 1801 may include a heat spreader plate 1869 that may be, for example, a dual-purpose device. As the name suggests, the heat spreader plate 1869 may provide heat conduction functionality by spreading heat provided by a heater component 1867, e.g., a thermo-electric cooler (TEC), which may be used to pump heat into the heat spreader plate 1869. The heater component 1867 may thus be mounted directly to the heat spreader plate 1869 or in a manner that provides a low-loss thermally conductive path between the heater component 1867 and the heat spreader plate 1869. The other functionality that may be provided by the heat spreader plate 1869 is to transfer pneumatic control signals from valves 1865 of the pneumatic control system of the base station 1801 to pneumatic control ports 1814 of the cartridge 1803. The valves 1865 may be provided both positive and negative pressure from pressurization pump 1859B and vacuum pump 1858B, respectively, and each valve 1865 may be individually controlled by the controller 1852B to select between positive or negative (or neutral) pressure to be applied to a given pneumatic control port 1814.

The actuation mechanism 1868 may include a cartridge clamp 1870 that may secure the cartridge 1803 in place and preload it against the heat spreader plate 1869, thereby causing the pneumatic control ports 1814 in the cartridge 1803 to be sealed against pneumatic ports in the heat spreader plate and for the microfluidic plate (not separately shown) of the cartridge 1803 to be pressed into thermal contact with the heat spreader plate 1869.

Operation of the base station 1801 will now be discussed with respect to FIG. 18 and with the assumption that the cartridge 1803 includes a microfluidic plate that is similar to the microfluidic plate 1304 of FIG. 13.

When the cartridge 1803 is loaded into the actuation mechanism 1868, an initial clamping operation may be performed in which the cartridge clamp 1870 is caused to move towards the heat spreader plate 1869 to cause the cartridge 1803 to be compressed against the heat spreader plate 1869. This may secure the cartridge 1803 in place and establish sealed pneumatic interfaces between the pneumatic control ports 1814 and corresponding ports on the heat spreader plate 1869.

In implementations with a heater component 1867, the heater component 1867 may be activated to heat the heat spreader plate 1869 which may then subsequently distribute such heat across the microfluidic plate 1304 which may, in turn, conduct heat to the buffer blisters 1831 and the substrate blisters 1830A/B. Such heating may be performed in order to thaw any liquids that may have frozen within the cartridge 1803 due to environmental conditions. For example, if the breath sampling and analysis system is a field unit intended for use by law enforcement officials in detecting THC and alcohol in a subject's breath, such tests may frequently be performed as part of a traffic stop at night, when temperatures are coldest. In many locales, such temperatures may, depending on the season, drop below freezing, and the quantities of liquid within the cartridge 1803 may be small enough that even a short duration exposure to the cold, such as may be experienced during breath sample collection, may cause the liquids housed therein to freeze solid. In order to address such circumstances, the base station 1801 may be equipped with the heater component 1867 and heat spreader plate 1869, as shown in FIG. 18, and the controller 1852B may be configured to cause the heater component 1867 to be activated for some duration of time before causing any processes to initiate that involve the movement of fluid within the microfluidic plate 1304. The heater component 1867 may be caused by the controller 1852B to start heating up prior to insertion of the cartridge, e.g., responsive to a wireless signal received by the base station 1801 from the handheld unit 1802 during breath sample collection by the handheld unit 1802, in response to insertion of the cartridge 1803 into the actuation mechanism 1568, or any other suitable trigger event. The heater component 1867 may be kept operative, if desired, during the analysis to prevent possible freezing or re-freezing of the liquids within the cartridge 1803. In some implementations, the heater component 1867 may be omitted. For example, if a breath sampling and analysis system is to be used in a controlled environment, e.g., in a hospital setting, it is extremely unlikely that below-freezing temperatures will be experienced, making it unlikely that the cartridge 1803 will need to be pre-heated or heated. In such instances, the heater component 1867 may be omitted, although the heat spreader plate 1869 may nonetheless be included to provide a pneumatic port interface with the microfluidic plate 1304, although in such cases, the name "heat spreader plate" may be somewhat of a misnomer—it will be recognized that the heat spreader plate in such instances may be more accurately thought of as a load spreader plate (a phrase which may be used to refer to either implementation, as in either case the plate in question distributes the load of the cartridge 1803 across a large area).

After the cartridge 1803 is loaded into the actuation mechanism 1868 and, if cartridge heating is provided, the cartridge 1803 heated to a desired temperature (as evidenced, for example, by temperature data from a temperature sensor within the cartridge or within the cartridge 1803) or for a desired period of time (e.g., such as a time period established to be long enough to ensure that the liquid within the cartridge has thawed), the blister compression frame 1871 may be actuated to compress the buffer blisters 1831 and the substrate blisters 1830A/B against the microfluidic plate 1304 to force the contents of each through an associated rupture valve and into the microfluidic plate 1304 to fill the buffer reservoir 1335 and the substrate reservoirs 1333A/B, respectively. In other implementations, other mechanisms for storing the buffer and substrates A/B may be used, e.g., such liquids may be stored directly in their respective reservoirs, thereby eliminating the need for blisters such as those discussed, and avoiding the need for the portions of the actuation mechanism directed towards activating such liquid storage devices. In other implementations, the liquids housed in the blisters may instead be stored in metering dispensers located in the base station 1801, or in a removable, replaceable reagent cartridge (not shown) that is insertable into the base station 1801. In such implementations, the base station 1801 may have additional functionality that may be activated to cause the reagent cartridge to deliver predefined quantities of each reagent to the microfluidic plate 1304 and/or the reservoirs within the cartridge 1803.

In the example microfluidic plate 1304, the reaction channels 1305A/B/C may each be coated during manufacture of the microfluidic plate 1304 with, for example, an antigen, e.g., THC or a derivative thereof, that is immobilized on the interior surfaces of the reaction channels 1305A/B/C. The "evidence" reaction channel 1305' may, in some implementations, be similarly coated, but may be uncoated in other implementations—as the sample collected in the "evidence" reaction channel 1305' may be analyzed using other analysis techniques from those used by the base station 1801, the sample collected therein may not be exposed to the same processing steps as performed on the samples within the other reaction channels 805A/B/C. A similar or identical (or near-identical) amount of antigen may separately be immobilized on the interior surfaces of each reaction channel 1305A/B/C. The antigen, generally speaking, may be the same as, or functionally equivalent to, the analyte of interest. Thus, if THC is the analyte, the antigen may also be THC.

In one such example implementation, the antigen may be THC conjugated to a support protein such as BSA or covalently bonded to the surface of the reaction channels.

After a breath sample is flowed through the reaction channel 1305A, the reaction channel 1305A may include analyte from two sources—the immobilized analyte and then any analyte that was contained within the breath sample and that adsorbed onto the interior surfaces of the reaction channel 1305A.

The reaction channels 1305B and 1305C, as suggested earlier, may not be configured to have breath sample flowed through them, but may instead contain control amounts of the analyte of interest for calibration purposes. In implementations that include immobilized antigen in each reaction channel 1305A/B/C, the control amounts of analyte that may be included in the reaction channels 1305B and 1305C will be "free" analyte, e.g., not immobilized, but either suspended in liquid form or adsorbed onto the interior surfaces of the reaction channels 1306B and 1305C in a manner that allows them to be eluted through introduction, for example, of buffer from the buffer reservoir so that they are no longer necessarily adsorbed onto the interior surfaces of those reaction channels.

After the buffer reservoir 1335 has been filled with buffer, an antibody pump 1310 may be actuated to cause a predefined amount of the buffer to be drawn from the buffer reservoir 1335 and delivered to the antibody reservoir 1332. The antibody reservoir 1332 may have a predefined quantity of lyophilized (freeze-dried) antibody contained within it that is allowed to mix with the introduced buffer in order to reconstitute the antibody; the buffer/antibody mixture may be allowed to rest for a predetermined time interval, e.g., ~30 seconds, to allow for sufficient antibody reconstitution. Once the predetermined time interval has elapsed, the controller may cause the reconstituted antibody to be moved into the reaction channels 1305A/B/C by causing positive pressure to be applied to antibody valves 1317A/B/C and to reaction channel valves 1320A/B/C to actuate them to an open state; once the antibody valves 1317A/B/C and the reaction channel valves 1320A/B/C are open, the controller may then cause reaction channel pumps 1308A/B/C to be cycled one or more times to draw equal amounts of reconstituted antibody into each of the reaction channels 1305A/B/C. It will be understood that, with the exception of optical site valves 1321A/B/C, which are independently actuable, the other valves and pumps depicted in FIG. 13 that share a common numeric designator followed by A/B or A/B/C may, for each such A/B or A/B/C cluster, be driven in unison responsive to a common pneumatic input. Thus, for example, the reaction channel valves 1320A/B/C may all open or close generally simultaneously responsive to a single pneumatic input. This may simplify the control system and reduce the number of pneumatic valves that must be provided in the base station 1801 in order to control valve and pump operation in the microfluidic plate 1304. In other implementations, of course, there may be more granular control of valves within the microfluidic plate, including, in an extreme case, implementations in which every valve and pump may be separately controllable or addressable by the base station 1801.

In one example implementation, the antibody may be a horseradish peroxidase (HRP) conjugated monoclonal antibody that is specific to cannabinol.

Once the predetermined amount of reconstituted antibody is delivered to each reaction channel 1305A/B/C, the reconstituted antibody may be allowed to incubate within the reaction channels 1305A/B/C for a predetermined time interval, e.g., 55-65 seconds, e.g., 60 seconds, or longer. The amount of reconstituted antibody that is introduced into each reaction channel 1305A/B/C may be generally equal (it will be recognized that the goal is to introduce equal amounts of reconstituted antibody to each reaction channel 1305A/B/C but that manufacturing variation in the reaction channel pumps 1308A/B/C, slight non-homogeneities in the reconstituted antibody solution, and other sources of variation may result in some variation in the amount of reconstituted antibody that is delivered to each reaction channel 1305A/B/C, although the amounts delivered will generally be understood within the art as being "substantially equal" despite such variations; such variations may range ±10% to ±20%).

During this incubation time, the antibody, which is selected to specifically bind to the analyte for which measurement is sought (and to the immobilized antigen in each reaction channel 1305A/B/C), will bind to the analyte and antigen. The antibodies may, for example, be conjugated antibodies, e.g., having enzymes or other additional or alternative molecules bonded thereto. The amount of reconstituted antibody that is provided to each reaction channel 1305A/B/C may be selected such that there are fewer antibodies delivered to each reaction channel 1305A/B/C than there are immobilized antigen sites for the antibody to bind to. Thus, if there is only immobilized antigen present in a given reaction channel 1305, then a high fraction of the antibody introduced into that reaction channel 1305 may bind with the immobilized antigen and may, itself, become immobilized. However, if the breath sample caused a quantity of analyte to be introduced into that same reaction channel 1305, the antigen and the introduced sample analyte may compete for antibodies, and the antibodies may bind to the sample analyte and the immobilized antigen in quantities proportionate to the amount of sample analyte and the immobilized antigen relative to the combined amount of sample analyte and immobilized antigen within that reaction channel 1305. Thus, if there is half as much sample analyte introduced into the reaction channel 1305 as there is immobilized antigen present in the reaction channel 1305, then about ⅓ of the antibody will bind to the sample analyte, and the other ⅔ of the antibody will bind to the immobilized antigen and, itself, become immobilized.

After the antibody has been allowed to incubate within the reaction channels 1305A/B/C, the reaction channels 1305A/B/C may be flushed or purged, e.g., by first pumping air through them, followed by a liquid wash using buffer from the buffer reservoir, and then again by pumping air through them. For example, the controller 18526 may cause the reaction channel valves 1320A/B/C to be opened and the reaction channel pumps 1308A/B/C to be actuated to draw fluid from the reaction channels 1305A/B/C and to dump the drawn fluid into the waste reservoir 1336. While the reaction channel pumps 1308A/B/C are applying negative pressure to the reaction channels 1305A/B/C, the controller 1852 may first cause the valves for vents 1313 directly fluidically connected with each of the reaction channel valves 1320A/B/C to be opened to allow air to be drawn into each of the reaction channels 1305A/B/C through the respective vent 1313. After a sufficient air purge interval, the controller 1852B may case the valves of the valves 1313 that were open to close while causing the buffer valves 1316A/B/C to open. With the buffer valves 1316A/B/C open, the negative pressure provided by the reaction channel pumps 1308A/B/C may draw buffer from the buffer reservoir 1335 and into the reaction channels 1305A/B/C, which may sweep sample analyte remaining in the reaction channels 1305A/B/C into the waste reservoir 1336. After a suitable interval of time, the controller 1852B may cause the buffer valves 1316A/B/C to close again, and may re-open the valves for the vents 1313 to repeat the air flush operation discussed previously for a similar interval of time.

After these washing/flushing operations, the reaction channels 1305A/B/C may generally contain only immobilized antigen and whatever antibodies have bonded to the immobilized antigen; the antibodies that bonded with the sample analyte will all generally have been flushed to waste.

During the time that the above operations are being performed, the controller 18526 may cause other operations to occur with other portions of the microfluidic plate 1304. For example, the vents 1313 fluidically connected with the substrate reservoirs 1333A/B and the substrate mixing reservoir 1334 may be caused to be actuated by the controller 1852B, and the substrate pumps 1309A/B may be actuated to cause substantially equal amounts of substrate to be dispensed from each of the substrate reservoirs 1333A/B into the substrate mixing reservoir 1334. It will be appreciated that in the example system, the substrates are stored in binary form to avoid prematurely triggering a reaction between the two reagents that are stored in the substrate reservoirs 1333A/B. Once analysis of a sample has begun, however, the substrate components stored in the substrate reservoirs 1333A/B may be pumped into the substrate mixing reservoir 1334 and allowed to mix, thereby reacting to form the substrate. In one example implementation, the substrate may be a luminescent substrate which is provided in a two-part binary form that, when mixed, will remain stable for approximately 8 hours and steadily luminesce for about 5 minutes after adding the substrate to the analyte of interest.

After the breath sample analyte and the antibodies bound thereto have been washed away, the substrate may be distributed to the reaction channels 1305A/B/C. For example, the controller 1852B may cause the substrate valves 1318A/B/C to be actuated to an open state (the valves of vents 1313 actuated during the wash and purge operations discussed above may be caused to be actuated to a closed state by the controller 1852B, and the valve of vent 1313 connected with the substrate mixing reservoir 1334 may be caused to be actuated to an open state by the controller 1852B) and may cause the reaction channel pumps 1308A/B/C to be cycled so as to draw predetermined amounts of substrate from the substrate mixing reservoir 1334 into each of the reaction channels 1305A/B/C; the predetermined amounts of substrate distributed to each reaction channel 1305A/B/C may be substantially equal. After the predetermined amounts of substrate have been dispensed to each reaction channel 1305A/B/C, the reaction channel pumps 1308A/B/C may be deactivated and the substrate valves 1318A/B/C and the valve associated with the vent 1313 connected with the substrate mixing reservoir 1334 may be caused to be actuated to a closed state by the controller 952B. The substrate may then be allowed to incubate within the reaction channels to allow the marker molecules in the substrate to be activated by any of the antibodies that are present in the reaction channels 1305/A/B/C. For example, if conjugated antibodies are used, the conjugate may be an enzyme such as horseradish peroxidase (HRP) that activates the marker molecules in the substrate and causes them to start luminescing. The higher the concentration of conjugated antibodies, the larger the luminescent response of the marker molecules will be.

At this stage, the breath sample preparation operations associated with analyses conducted with such an example microfluidic plate 1304 are substantially complete, and actual measurement of the analyte in each sample or control may begin.

In this example implementation, the measurement of analyte may be performed in an indirect manner, as the analyte itself was flushed to waste earlier in the process discussed above. However, an estimation of how much analyte was present within each reaction channel prior to the flushing operation may be indirectly obtained by measuring the luminescent response of the substrate from each separate reaction channel 1305A/B/C. In order to do so, the substrates within each reaction channel 1305A/B/C may be separately pumped to the optical measurement site 1306 (or to separate optical measurement sites 1306 if measurement is to be done, for example, in parallel) and measurements of emitted light from the substrate for each reaction channel 1305A/B/C may be obtained; the amount of light measured for each such sample will be directly influenced by the concentration of antibodies in the reaction channel 1305A/B/C from which each sample was drawn. If each optical measurement is taken with respect to an identically-sized portion of the substrate from each reaction channel 1305A, then the relative intensities of the emitted light from each measured portion will generally indicate the relative quantities of antibodies within the reaction channel 1305A/B/C for each measured portion. If the reaction channels 1305B and 1305C contain known control amounts of the analyte, then the amount of analyte in the reaction channel 1305A, in turn, may be determined through, for example, interpolation between the known control amounts of analyte based on the measured light intensities.

In some implementations, the lower control amount may be selected to be close to a pre-established threshold amount of analyte that is deemed to be indicative of a particular physiological state. In the case of THC as the analyte, the threshold amount may, for example, be the lower limit of the amount of THC that must be present in a breath sample in order to consider the subject to be under the influence of THC and/or to consider the subject as having ingested or inhaled THC within, for example, the last two or three hours; in the latter case, this may be on the level of 2-2.5 picograms per 0.5 liters of breath sample volume, although perhaps higher. In other implementations, the lower control amount may be set to other values, e.g., no analyte at all. The upper control amount may be selected to be higher than the lower control amount; in some implementations, the upper control amount may be selected to be near the maximum expected quantity of analyte within a given breath sample.

After the antibodies introduced into each reaction channel 1305A/B/C have been allowed to bind to the antigen and/or analytes in each reaction channel 1305A/B/C, the non-immobilized analyte (breath sample analyte and control amounts of analyte) and antibodies bound thereto in each reaction channel 1305A/B/C may be flushed out and the reaction channels 1305A/B/C purged and washed. Equal quantities of substrate may then be dispensed into each reaction channel 1305A/B/C; the marker molecules in the substrate may preferentially bind with any antibodies that are present in each reaction channel 1305A/B/C. Following an incubation period to allow the marker molecules in the substrate to bind with whatever antibodies are present within each reaction channel 1305A/B/C, the substrate and unbound marker molecules within each reaction channel 1305A/B/C may be drawn, e.g., by actuating the respective optical site valve 1321A/B/C and the optical measurement site pump 1307, into the optical measurement site 1306, at which point an optical measurement may be obtained of a portion of the substrate present within the optical measurement site. It will be understood that in systems in which the same optical measurement site 1306 is used to separately obtain measurements from each substrate, the optical measurement site 1306 may be purged with air and washed with buffer (and optionally purged with air again), in a manner similar to how the reaction channels 1305A/B/C were purged/washed in earlier operations, in between each substrate measurement.

The exact quantity of substrate that is pumped into the optical measurement site 1306 for each measurement need not be identical, although the region of the optical measurement site 1306 that is within the active detection area of the optical measurement module should have equal amounts of substrate within it for each measurement. Thus, while the optical measurement site 1306 may be 2 mm by 6 mm, the active detection area of the optical measurement module may be limited to a 2 mm square region in the middle of the optical measurement site, so only a portion of the light emitted from the substrate within the optical measurement site 1306 may be detected by the optical measurement module. Accordingly, the illumination intensity measurements obtained by the optical measurement module will be representative of an illumination density of the substrate being measured, e.g., the amount of illumination generated by a given volume of the substrate within the active measurement area of the optical measurement module. The illumination density, in turn, is directly proportional to the quantity of antibodies that were present in the reaction channels 1305A/B/C when the substrate was introduced. This amount, in turn, is inversely proportional to the amount of analyte that was present when the analyte and the immobilized antigen competed for antibodies. Thus, such luminescence measurements may allow for two possible types of measurement—(a) a binary measurement, e.g., is the level of analyte above or below a control amount of analyte and (b) an interpolated quantification measurement, in which the actual amount of analyte in the reaction channel 1305A (or a portion thereof) may be determined by interpolating between the known control amounts of analyte in the reaction channels 1305B/C based on where the luminescence measurement of the breath sample substrate falls relative to the luminescence measurements of the control amounts.

It will be appreciated that other types of microfluidic analysis protocols may be implemented in a similar fashion, e.g., on a microfluidic plate modified to suit the particularities of any particular selected analysis protocol, as desired. Regardless of the particular protocol adopted, however, various aspects of the breath sampling and analysis systems set forth herein may be common to such different protocols. For example, the underlying cartridge design may be used to capture breath samples generally regardless of which analysis protocol is later used to then analyze the captured samples (although the number and location of blister packs or equivalent reagent storage volumes may differ depending on the needs of the selected protocol, and the layout of channels, valves, and pumps in the microfluidic plate may be changed depending on the type of analysis selected. The handheld unit may be relatively unaffected by the selection of any particular analysis protocol since the handheld may, in many implementations, play an active, physical role during sample collection and not analysis (although in some implementations, the handheld unit may have a controller that controls operation of the base station during analysis, e.g., via a physical connection while docked or wirelessly, e.g., via a Bluetooth connection). The base station, similarly, may include various subsystems that may generally remain physically unchanged regardless of what analysis protocol is selected for analyte measurement. For example, the actuation mechanism that loads the cartridge and prepares the cartridge for analysis in some implementations may operate in a similar manner regardless of which analysis protocol is selected.

Figure 19:
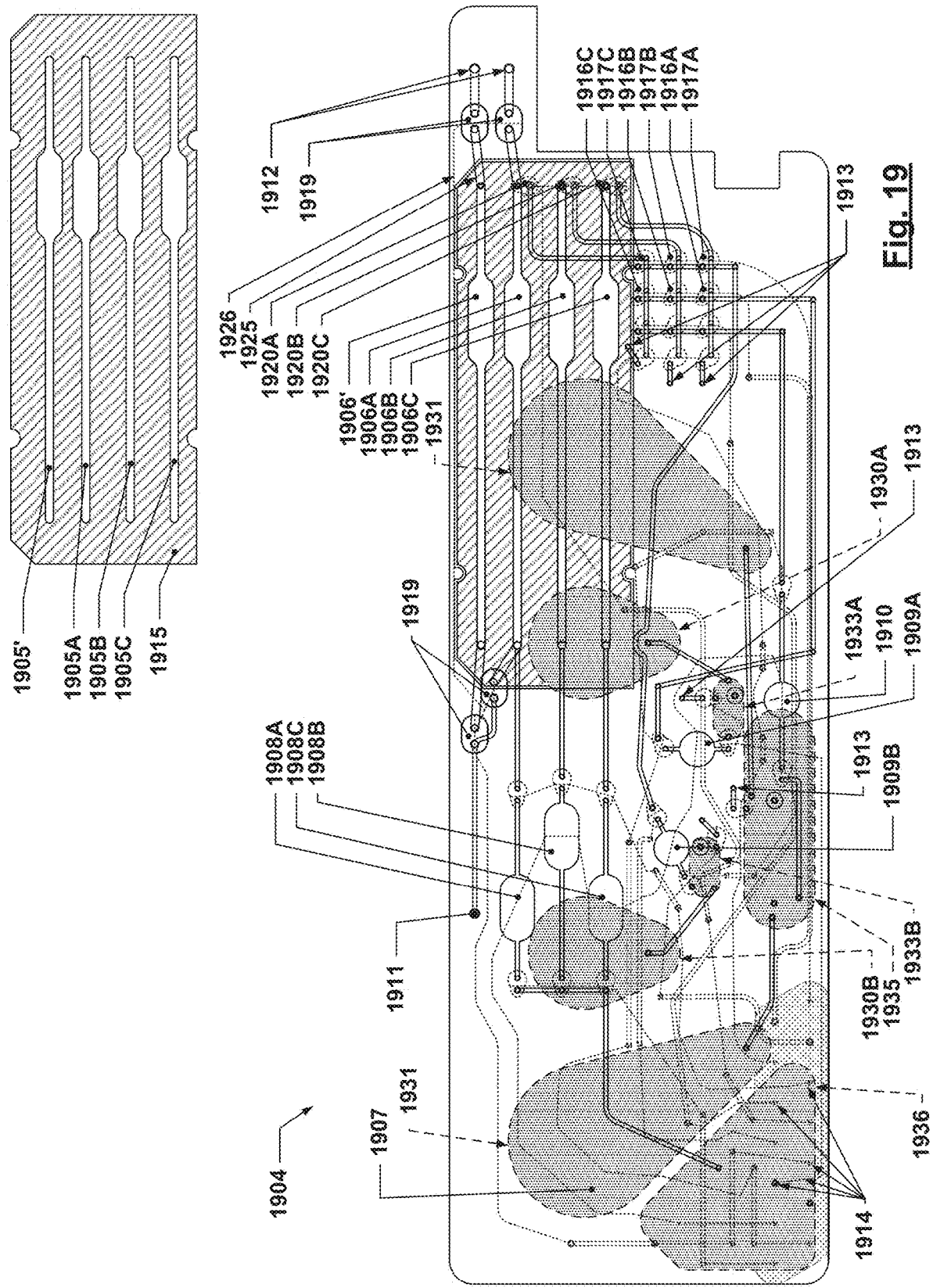
FIG. 19 depicts another example microfluidic plate that may be used with the example breath sampling and analysis system of FIG. 8.
Figure 20:
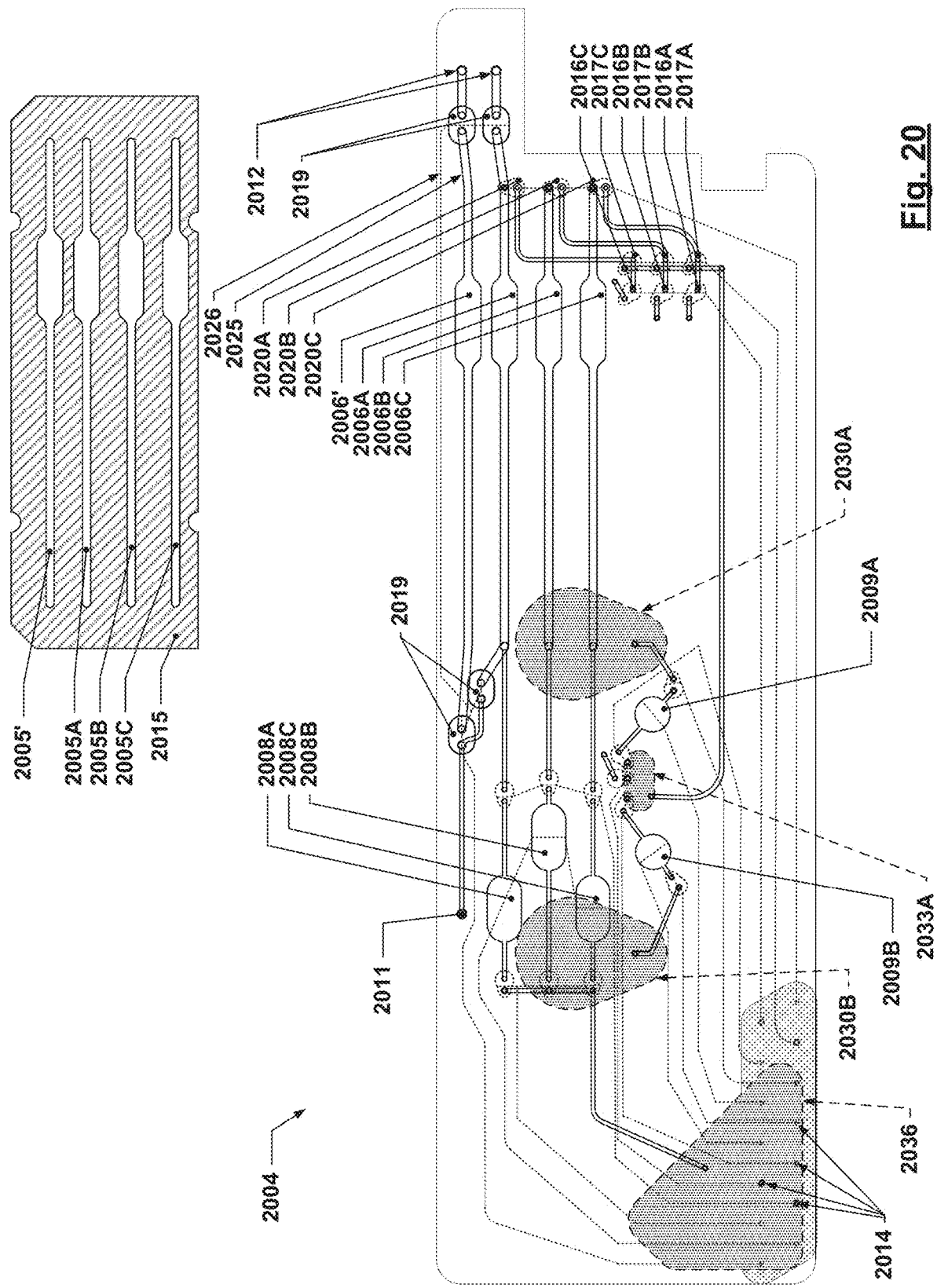
FIG. 20 depicts another example microfluidic plate that may be used with the example breath sampling and analysis system of FIG. 8.
Figure 21:
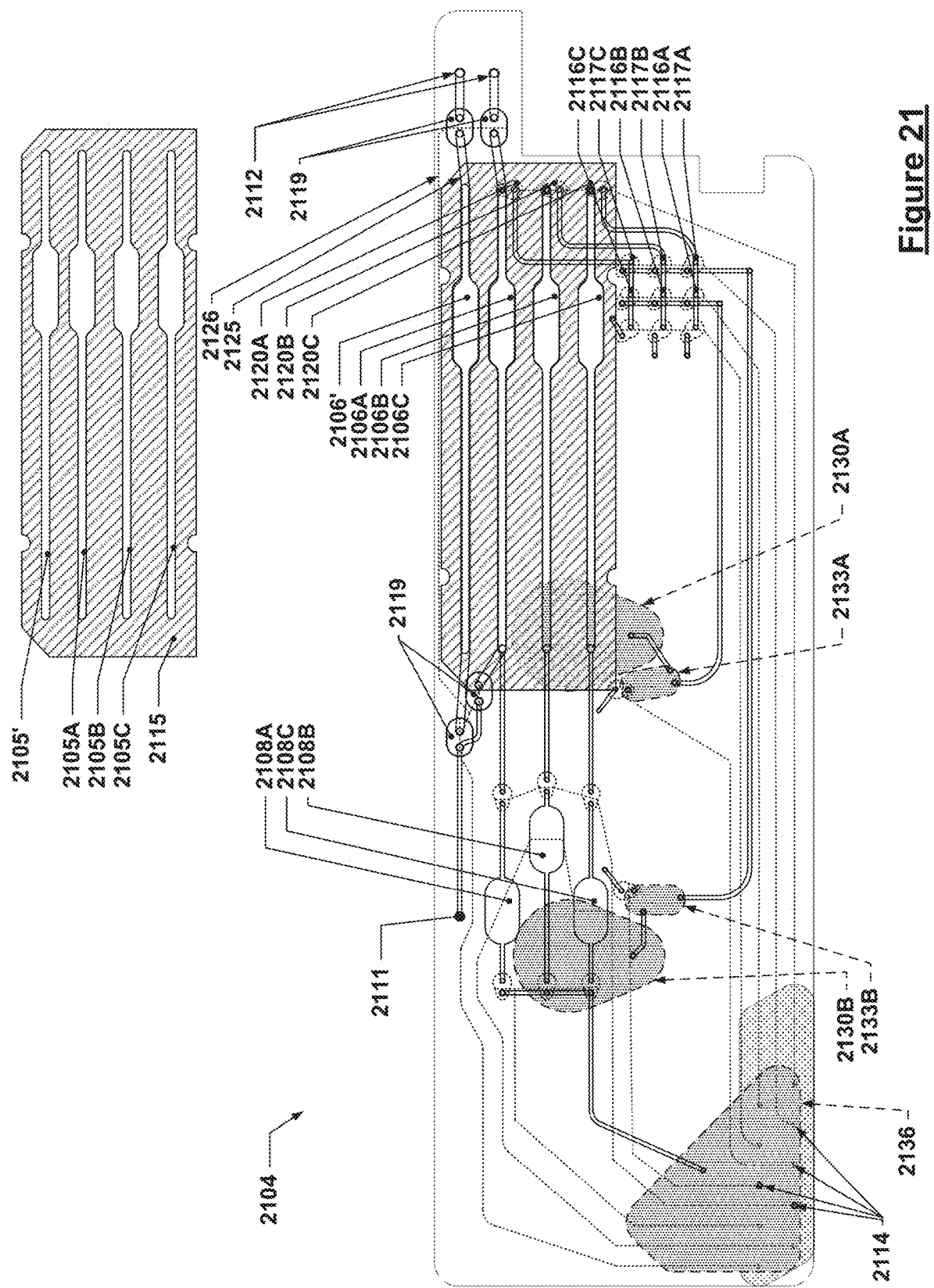
FIG. 21 depicts another example microfluidic plate that may be used with the example breath sampling and analysis system of FIG. 8.

FIGS. 19, 20, and 21 depict other examples of microfluidic plates that may be used to implement additional or alternative types of analysis. For example, FIG. 19 depicts an example microfluidic plate that may be used with the example breath sampling an analysis system of FIG. 8 to perform a functionalized diazofluorophor-based analysis of a breath sample. Microfluidic plate 1904 may be similar in many respects to the microfluidic plate 1004 discussed earlier, but may also differ in several respects. It may be assumed that structures that are referenced by callouts with the same last two digits as callouts in FIG. 10 are similar to the corresponding structures in FIG. 10 unless otherwise indicated.

In FIG. 19, the reaction channels 1905' and 1905A/B/C may be optionally located in a sub-module that may similar to the sub-modules discussed earlier. It will be noted, however, that the reaction channels in this example include the optical measurement sites 1906' and 1906A/B/C instead of a separate optical measurement site to which various fluids must be pumped.

During operation, the microfluidic plate of FIG. 19 may receive indicator solvent from blister 19308 that may be then stored in indicator reservoir 1933B, where it may mix with and dissolve a powderized, granularized indicator, e.g., for THC detection, rhodamine-123 or similar indicator that forms a fluorescent adduct when allowed to react with THC, that is stored within the indicator reservoir to form a liquid indicator.

In the example microfluidic plate 1904, the reaction channels may, prior to sample collection, have had an analyte-specific antibody immobilized on the surfaces thereof. For example, a THC-specific antibody may be immobilized on the surfaces of each reaction channel 1905A/B/C if THC is the analyte in question. When breath sample is flowed through the reaction channel 1905A, analytes in the breath sample may bond with the antibodies immobilized within the reaction channel 1905A and may thereby become immobilized themselves within the reaction channel 1905A. As with the microfluidic plate of FIG. 10, the reaction channels 1905B and 1905C may contain control amounts of the analyte in question (which may bind with the antibodies in those respective reaction channels as well) to provide a baseline against which measurement of analyte may be compared in order to quantify the amount of analyte that is present in the breath sample.

While the indicator is being reconstituted (or earlier, if desired), the reaction channels 1905A/B/C may be flushed and washed with buffer or wash solvent contained within wash reservoir 1935, which may be filled with buffer or wash solvent from buffer or wash blisters 1931, by opening buffer or wash valves (unlabeled, but the three valves immediately to the left of activator valves 1916A/B/C) and activation channel valves 1920A/B/C and then activating wash pump 1910 and/or actuation channel pumps 1908A/B/C to pump wash fluid through the reaction channels 1905A/B/C and into the waste reservoir 1936. This will generally flush whatever breath sample remains in the reaction channel 1905A out of the reaction channel 1905A (and may similarly flush the contents of the reaction channels 1905B and 1905C) and into waste. The analyte in each reaction channel 1905A/B/C that is bound to the immobilized antibody in each reaction channel 1905A/B/C will, however, remain within the reaction channels 1905A/B/C after such flush operations.

After waiting a sufficient period of time for the indicator to dissolve, and after the reaction channels 1905A/B/C have been flushed, indicator valves 1917A/6/C and actuation channel valves 1920A/B/C may be actuated into an open state and indicator pump 1909B and/or reaction channel pumps 1908A/B/C may be activated to pump the indicator solution from the indicator reservoir 1933B into the reaction channels 1905A/B/C. Once in the reaction channels 1905A/B/C, the indicator may react with any analyte, e.g., THC, that is present in the reaction channels. In the example microfluidic plate 1904, the reaction channels may, prior to sample collection, have had an analyte-specific antibody immobilized on the surfaces thereof. For example, a THC-specific antibody may be immobilized on the surfaces of each reaction channel 1905A/B/C if THC is the analyte in question. When breath sample is flowed through the reaction channel 1905A, analytes in the breath sample may bond with the antibodies immobilized within the reaction channel 1905A and may thereby become immobilized themselves within the reaction channel 1905A. As with the microfluidic plate of FIG. 10, the reaction channels 1905B and 1905C may contain control amounts of the analyte in question to provide a baseline against which measurement of analyte may be compared in order to quantify the amount of analyte that is present in the breath sample.

In conjunction with flowing the indicator solution into the reaction channels 1905A/B/C, an activator solution from activator reservoir 1933A may optionally be pumped to the reaction channels 1905A/B/C by opening activator valves 1916A/B/C as well and activating activator pump 1909A and/or activation channel pumps 1908A/B/C.

After the indicator solution and the optional activator have been introduced into the reaction channels 1905A/B/C, they may be allowed to incubate in the reaction channels 1905A/B/C for a sufficient period of time, e.g., 60 seconds, to produce the adduct by reacting with the bound analyte. The activator solution may, for example, be a liquid compound that may react with the adduct formed by the indicator and may enhance the adduct's fluorescent response. In some implementations, the activator may be omitted if the adduct produced already has adequate fluorescent response. The activator solution, like the indicator solvent, may be stored prior to analysis in an activator blister 1930A and dispensed to the activator reservoir 1930A when analysis begins.

Once the adduct has formed and any optional activator added to the reaction channels, optical measurements may be taken from optical measurement sites 1906A/B/C, e.g., by stimulating each optical measurement site with light of a first wavelength selected to stimulate the adduct to produce light of a second wavelength. A measurement may be taken of the intensity of the second wavelength light at each optical measurement site using an optical measurement module to determine the relative quantity of adduct in each measurement site. In such microfluidic plates, the layers of the microfluidic plate 1904 may be made from a light-opaque material, aside from the layers interposed between the measurement sites 1906A/B/C and the optical measurement module. In this instance, the measured light intensity is proportionate to the amount of analyte present in each reaction channel (as opposed to an inverse thereof).

FIG. 20 depicts another example microfluidic plate that may be used with the example breath sampling an analysis system of FIG. 8. Microfluidic plate 2004 may be similar in many respects to the microfluidic plates 1904 and 1004 discussed earlier, but may also differ in several respects. It may be assumed that structures that are referenced by callouts with the same last two digits as callouts in FIGS. 10 and 19 are similar to the corresponding structures in FIGS. 10 and 19 unless otherwise indicated. The microfluidic plate 2004 of FIG. 20 has a simpler architecture than the microfluidic plates of FIG. 10 or 19 and may be used, for example, to perform analysis protocols in which a binary indicator may be stored in two separate blisters 2030A/B for long term storage. The binary indicator may then be transferred to corresponding indicator reservoirs 2033A/B when the cartridge is prepared for analysis, and metered amounts of each component of the indicator may then be pumped into an indicator mixing reservoir 2034 using indicator pumps 2009A/B. For THC detection, for example, one blister may contain a rhodamine-123 dissolved in an acid, e.g., hydrochloric acid, and the other blister may contain a solution of sodium nitrate. The two solutions may then be mixed together in the mixing reservoir 2034 and then, once mixed, transferred to the reaction channels 2005A/B/C and allowed to react with whatever analyte is present. Similar to the implementation of FIG. 19, optical measurements may then be taken from the optical measurement sites 2006A/B/C and analyzed in order to determine a quantity of analyte present in the reaction channel 2005A relative to known control quantities of analyte in reaction channels 2005B and 2005C.

FIG. 21 depicts another example microfluidic plate that may be used with the example breath sampling an analysis system of FIG. 8. Microfluidic plate 2104 may be similar in many respects to the microfluidic plates 2004, 1904, and 1004 discussed earlier, but may also differ in several respects. It may be assumed that structures that are referenced by callouts with the same last two digits as callouts in FIGS. 10, 20, and 19 are similar to the corresponding structures in FIG. 10, 20, or 19 unless otherwise indicated. This implementation includes a microfluidic plate 2104 similar to that shown in FIG. 20, although the mixing reservoir 2034 is omitted and the contents of each reservoir 2133A/B may instead be independently pumpable into the reaction channels 2005A/B/C directly. Such a microfluidic plate structure may be used in analysis protocols such as LOCI (luminescent oxygen channeling) assays. For example, reservoir 2133A may include donor beads for such an assay, and reservoir 2133B may contain acceptor beads for such an assay. The beads in both reservoirs 2133A/B may be stored in a dried format and then reconstituted by flowing a buffer from the blisters 2131A/B into each respective reservoir at the start of analysis. The donor beads and acceptor beads may each be bound or coated with antibodies that may be specific to the analyte of interest. After a sufficient amount of time has elapsed to allow the donor and acceptor beads to be reconstituted, the donor bead and acceptor bead solutions may be pumped to the reaction channels 2105A/B/C. After sufficient incubation time has elapsed, the reaction channels may be optically stimulated to excite the donor beads. Donor beads that are spatially proximate to acceptor beads by virtue of the antibodies on both beads binding to a common analyte molecule will then emit an oxygen molecule that, in turn, causes the acceptor beads to emit light at a different wavelength than the excitation illumination wavelength. This emitted light may then be measured to determine a magnitude of emitted light that is proportionate to the amount of analyte present in the stimulated reaction channel. As with the other analysis protocols discussed herein, such a measured light intensity may be compared to the measured light intensities from similar measurements performed for control amounts of analyte in other reaction channels in order to determine a quantity of measured analyte from a breath sample relative to the known quantities of control analyte.

Figure 22:
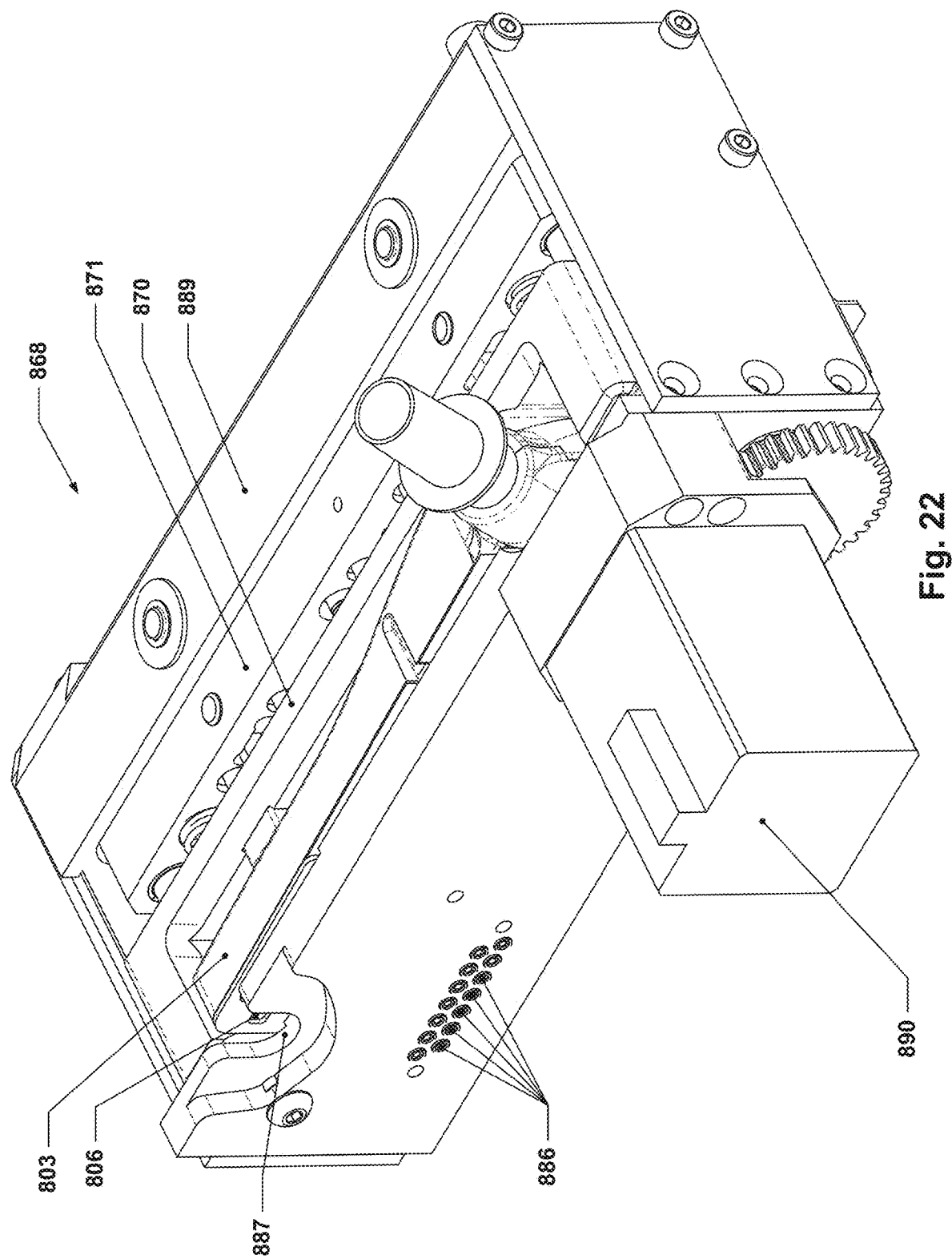
FIG. 22 depicts an example actuation mechanism.
Figure 23:
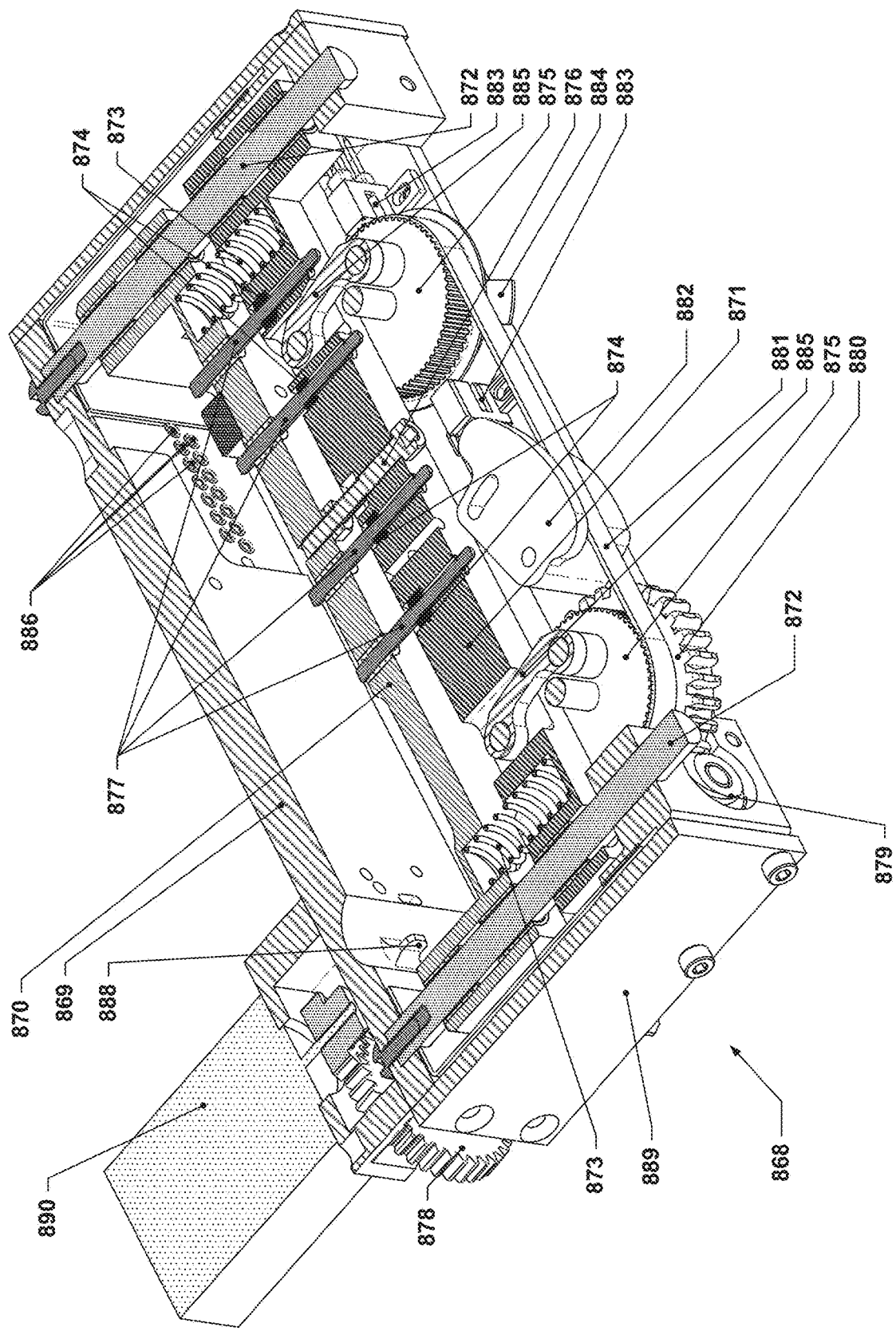
FIG. 23 depicts a cutaway view of the example actuation mechanism of FIG. 22.
Figure 24:
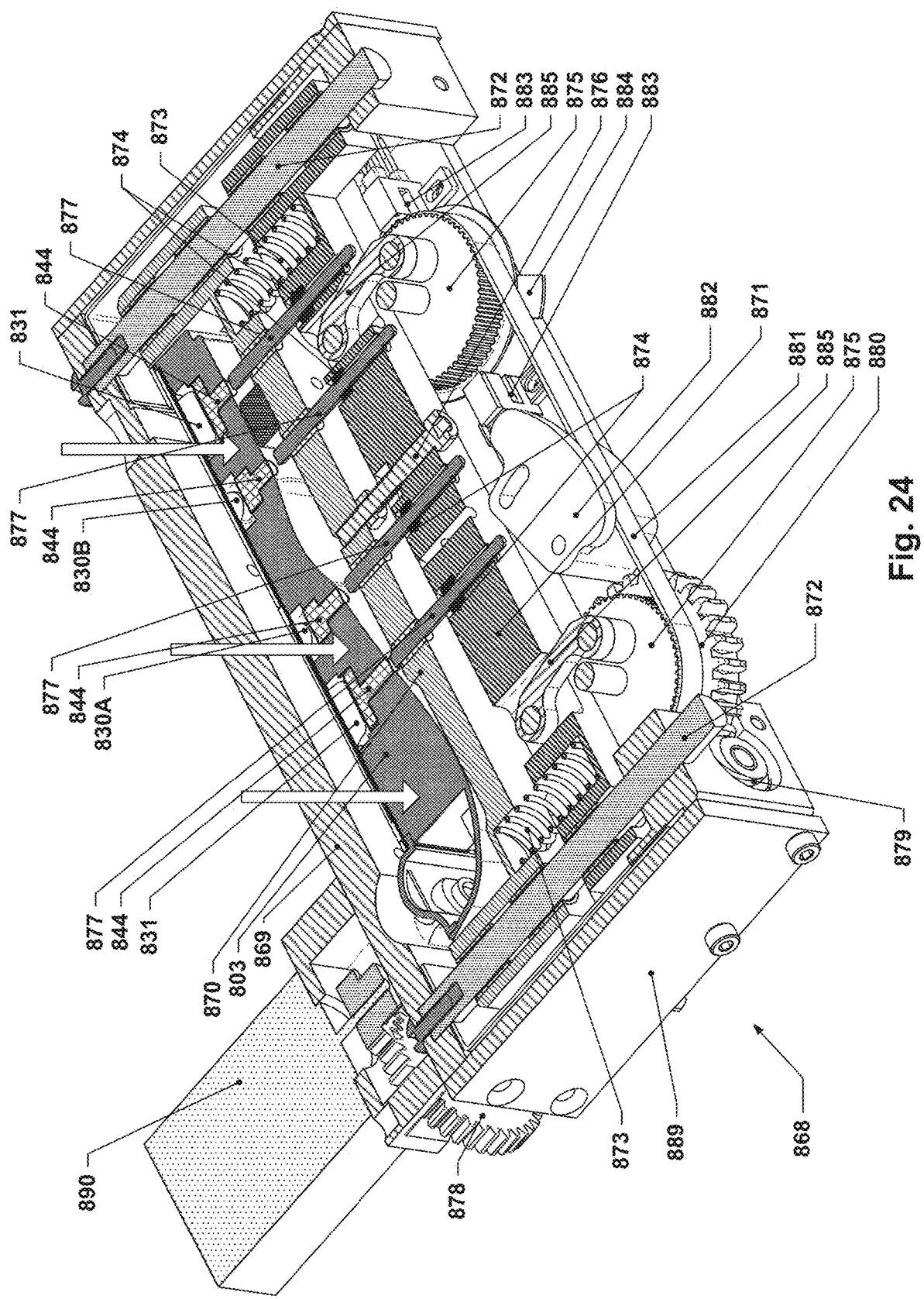
FIG. 24 depicts a cutaway view of the example actuation mechanism of FIG. 22 with an example cartridge inserted.
Figure 25:
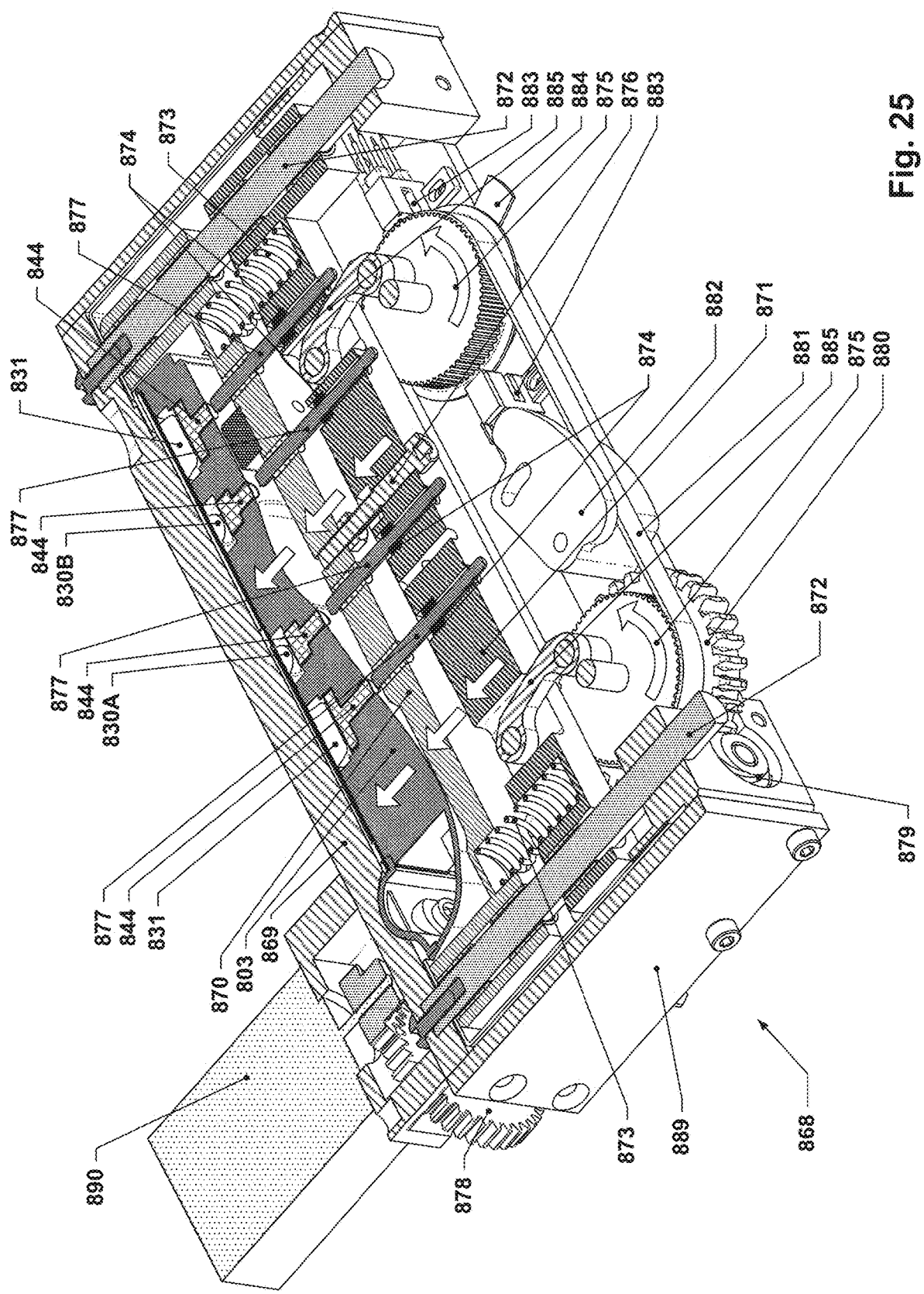
FIG. 25 depicts a cutaway view of the example actuation mechanism of FIG. 22 with the example cartridge clamped.
Figure 26:
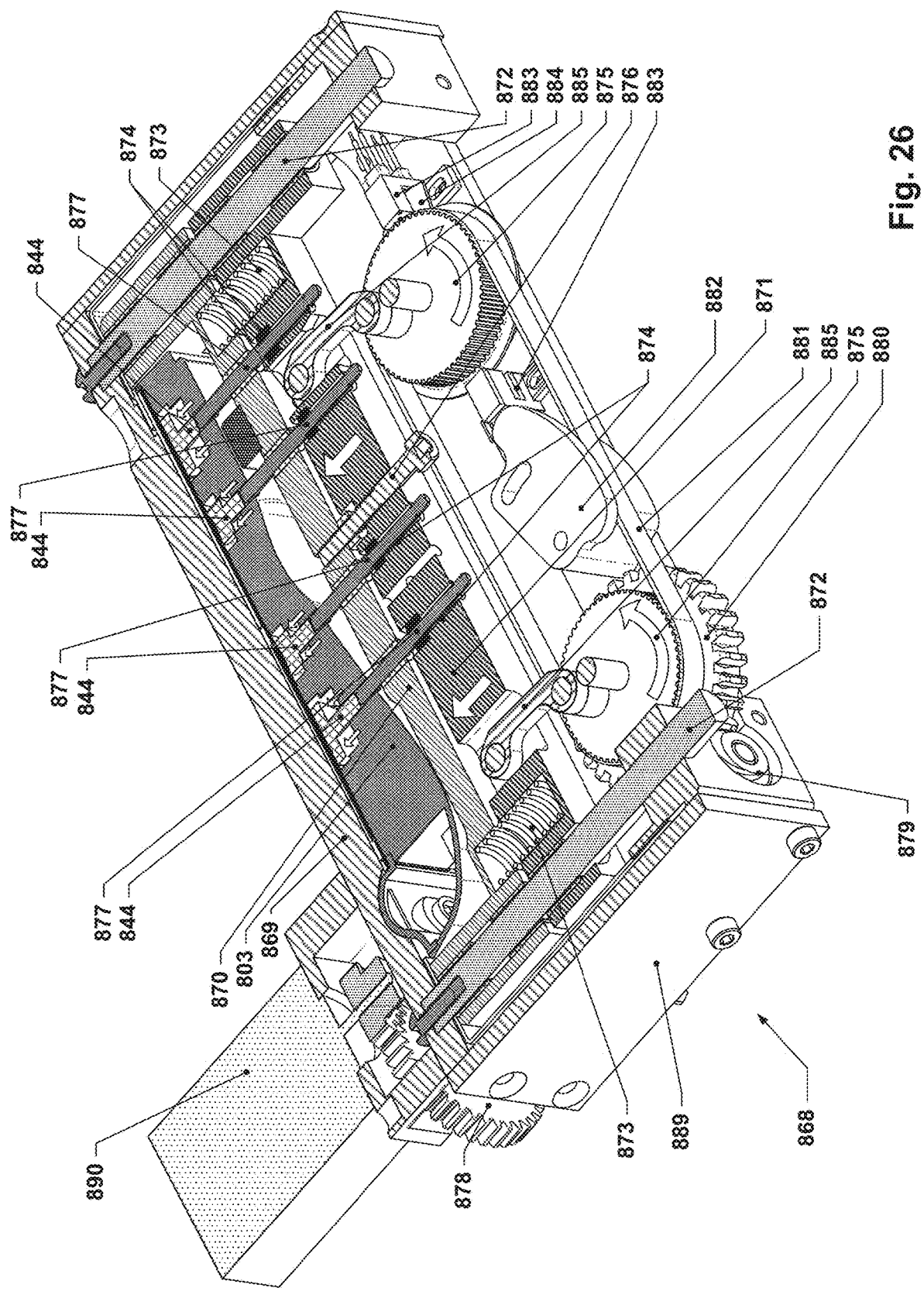
FIG. 26 depicts a cutaway view of the example actuation mechanism of FIG. 22 with the example cartridge ready for analysis to begin.

FIG. 22 depicts an example actuation mechanism. FIG. 23 depicts a cutaway view of the example actuation mechanism of FIG. 22. FIG. 24 depicts a cutaway view of the example actuation mechanism of FIG. 22 with an example cartridge inserted. FIG. 25 depicts a cutaway view of the example actuation mechanism of FIG. 22 with the example cartridge clamped. FIG. 26 depicts a cutaway view of the example actuation mechanism of FIG. 22 with the example cartridge ready for analysis to begin.

As can be seen in FIGS. 22-26, the actuation mechanism 868 may be configured to receive the cartridge 803, and may include an overall support frame 889 that is fixedly mounted to the heat spreader plate 869. A motor 890 may be mounted to the support frame 889 or the heat spreader plate 869; the motor 890 may be controlled to operate the actuation mechanism 868. The heat spreader plate 869 may include, for example, pneumatic supply ports 886 that may interface with the pneumatic control ports 814 on the cartridge 803 when the cartridge 803 is fully loaded into the actuation mechanism 868. The pneumatic supply ports 886, in turn may be interfaced with pneumatic passages in the pneumatic transfer manifold 861 that fluidically connect each pneumatic supply port 886 to one of the valves 865. If a heater component 867 is used, the heater component 867 may be mounted to a surface of the heat spreader plate 869, e.g., to the surface to which the motor 890 is mounted.

The actuation mechanism 868 may include two separately translatable elements—the cartridge clamp 870 and the blister compression frame 871. As can be seen in FIGS. 23-26, the cartridge clamp 870 and the blister compression frame 871 are both constrained to slide along guide rods 872. In the depicted implementation, the cartridge clamp 870 and the blister compression frame 871 are separated by a springs 873 that act to push the two components apart and form a gap between the cartridge clamp 870 and the blister compression frame 871. A floating stop 876 may limit the size of such a gap but may also permit the cartridge clamp 870 and the blister compression frame 871 to be compressed closer to each other, if subjected to sufficient external compressive force. In the depicted implementation, the blister compression frame 871 may be kinematically linked to wheels 875 by links 885 such that rotation of the wheels 875 causes the links to translate the blister compression frame 871 along the guide rods 872. The wheels 875 may, for example, be driven in unison through the use of a belt 881, thus allowed rotational input from the motor 890 to be provided to one of the wheels 875 directly, and then transmitted to the other wheel 875 by the belt 881. Rotational input from the motor 890 may, for example, be provided through drive gears 878, worm gear 879, and driven gear 880. A tensioner 882 may be provided to allow any slack in the belt 881 to be taken out through manual adjustment. It will be understood that other configurations or implementations may feature other mechanisms for translating the blister compression frame 871 along the guide rods 872, and that the present disclosure is not, generally speaking limited to the specific implementations discussed and depicted herein.

As shown in FIG. 24, a cartridge 803 may be inserted into the actuation mechanism 868. The blister compression frame 871 may then be translated towards the cartridge 803 and the heat spreader plate 869, which may, in turn, cause the cartridge clamp 870 to also translate towards the heat spreader plate 869 until it comes into contact with the cartridge 803. At this point, the cartridge clamp 870 may be further translated by the blister compression frame 871, as shown in FIG. 25, so as to push the cartridge 803 into contact with the heat spreader plate 869. Centering features, such as centering feature 888, may engage with corresponding features on the cartridge 803 to guide the cartridge 803 into an aligned state such that, for example, the pneumatic supply ports 886 of the heat spreader plate 869 are aligned with, and seal to, the corresponding pneumatic control ports 814 on the cartridge 803. Once the cartridge 803 is pressed into contact with the heat spreader plate 869, the cartridge housing may resist further compression, resulting in compression of the springs 873 if the blister compression frame 871 is further translated towards the cartridge 803.

As discussed earlier, if a heater component is used to heat the heat spreader plate 869, the actuation mechanism may be paused in the configuration shown in FIG. 25, or driven very slowly, so as to give the heat spreader plate 869 time to thaw any potentially frozen liquids within the cartridge 803.

Once sufficient heating has been performed (assuming that such heating is needed), the blister compression frame 871 may continue to be translated towards the cartridge 803. Actuation posts 877, which may be mounted to the blister compression frame 871, may be caused to insert themselves into the cartridge 803 so as to engage with blister plungers 844 and push them towards the heat spreader plate 869 without further compressing the cartridge 803. The continued translation of the blister compression frame 871 may cause further compression of the springs 873, thereby exerting more pressure on the cartridge 803, but the amount of such compression may be much lower than the compression exerted by the blister compression frame 871 on the blister plungers 844.

As shown in FIG. 26, when the blister compression frame 871 is translated by a sufficient further amount, the buffer blisters 831 and the substrate blisters 830A/B may be compressed by the blister plungers 844, forcing liquid from the blisters into the microfluidic plate. The actuation posts 877 may be mounted to the blister compression frame 871 with some small ability to translate relative to the blister compression frame 871 along the same axis as the blister compression frame 871 translates, thereby allowing some minor variation in the distances traveled by the blister plungers 844 during blister compression. The interfaces between the actuation posts 877 and the blister compression frame 871 may be equipped with Belleville washer stacks, e.g., Belleville washers stacked in alternating directions (a "series" configuration) so as to form a compact, high-stiffness spring that allows the actuation posts 877 to move relative to the blister compression frame 871 only when subjected to a large compressive force, e.g., such as when a blister is completely empty and the associated blister plunger 844 is, in effect, exerting force on incompressible materials between the blister plunger 844 and the heat spreader plate 869.

The actuation mechanism may be equipped with various sensors that may be used to monitor cartridge loading and compression. For example, the actuation mechanism 868 may include one or more photosensors 883, which may be interrupted by an interrupter 884 that is mounted to one of the wheels 875 at different positions, e.g., when the blister compression frame 871 is fully retracted or extended into full compression mode.

It will be understood that other actuation mechanisms may be used as well that provide similar functionality. In some such alternative implementations, the blister compression frame 871 and the cartridge clamp 870 may be separately driven, e.g., by separate motors.

Figure 27:
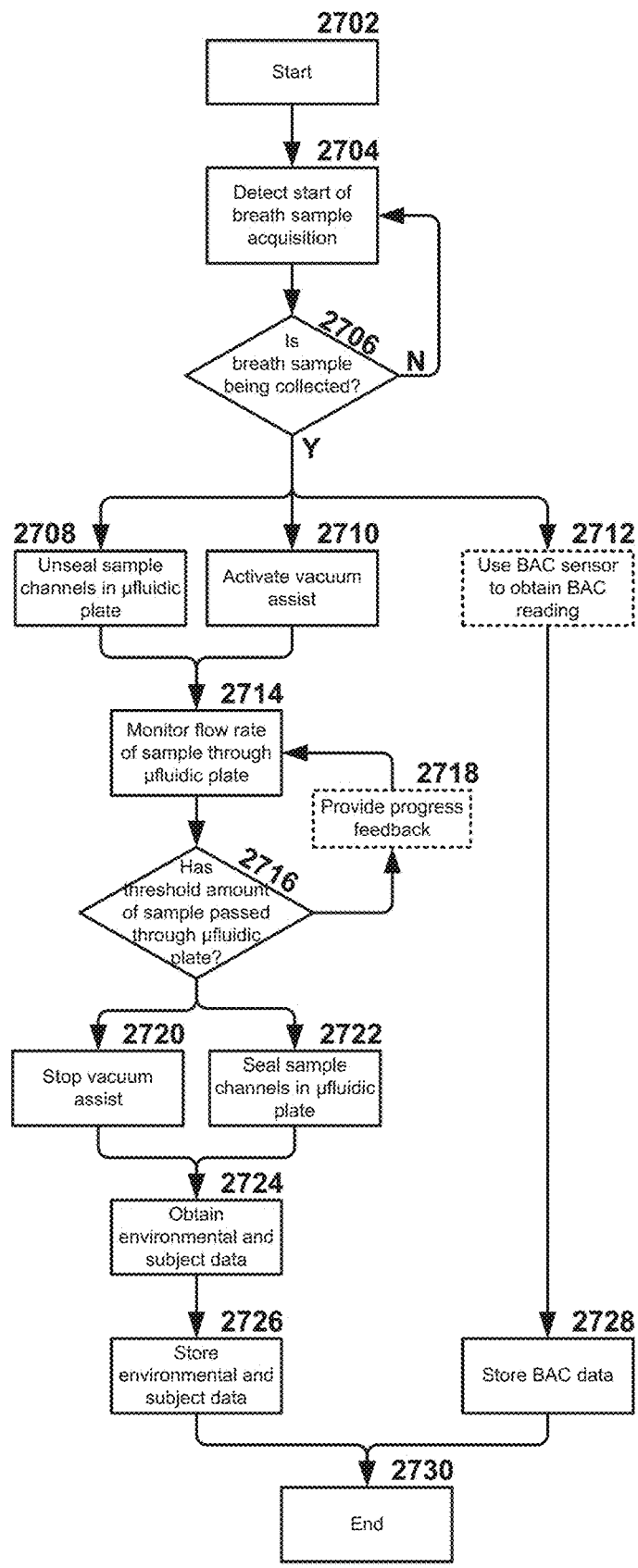
FIG. 27 depicts an example breath sampling technique.
Figure 28:
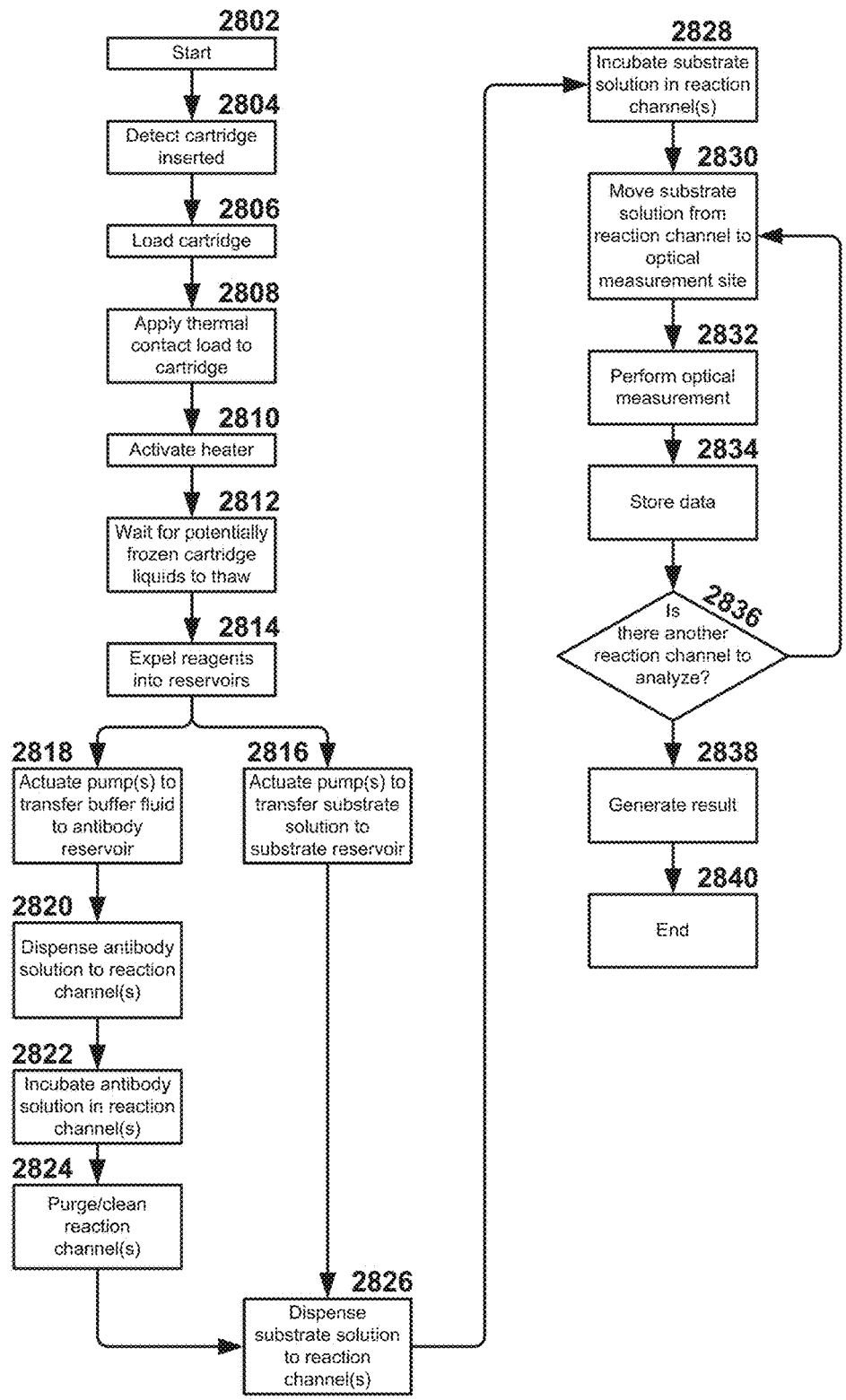
FIG. 28 depicts an example breath sample analysis technique using an insertable cartridge.
Figure 32:
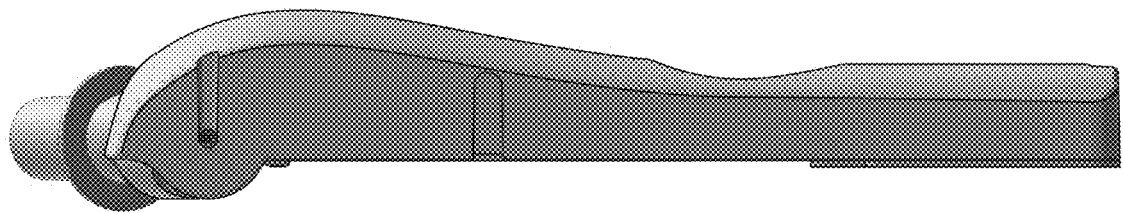
FIG. 32 is an opposite side view of the cartridge of FIG. 29.
Figure 31:
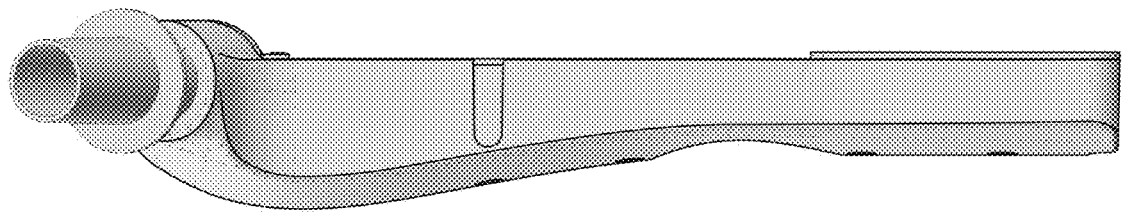
FIG. 31 is a side view of the cartridge of FIG. 29.
Figure 30:
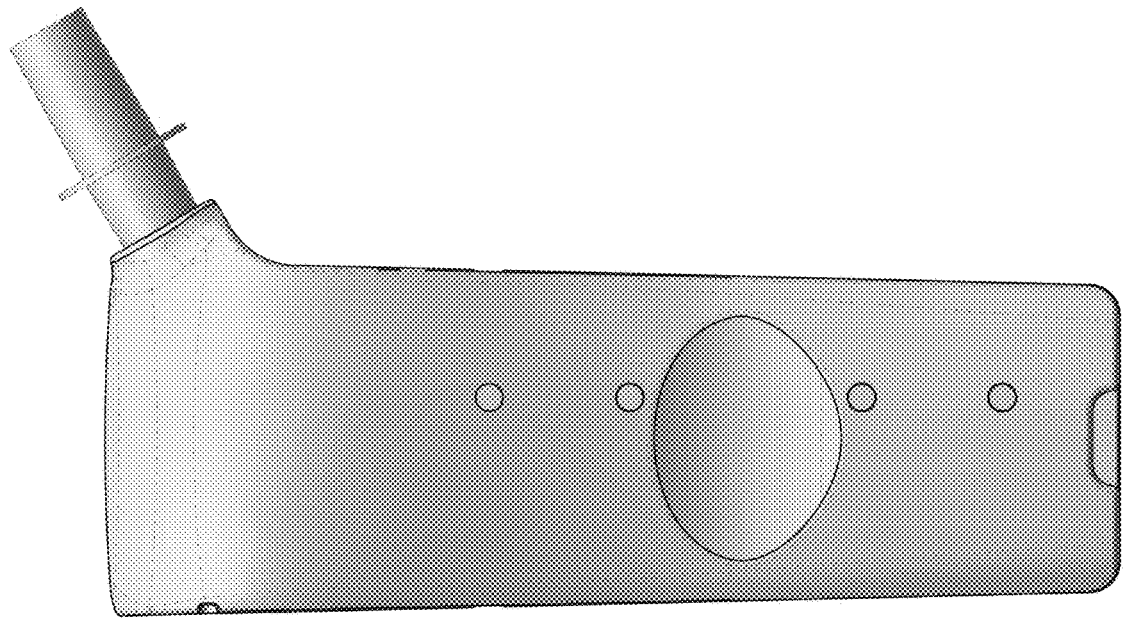
FIG. 30 is a front view of the cartridge of FIG. 29.
Figure 29:
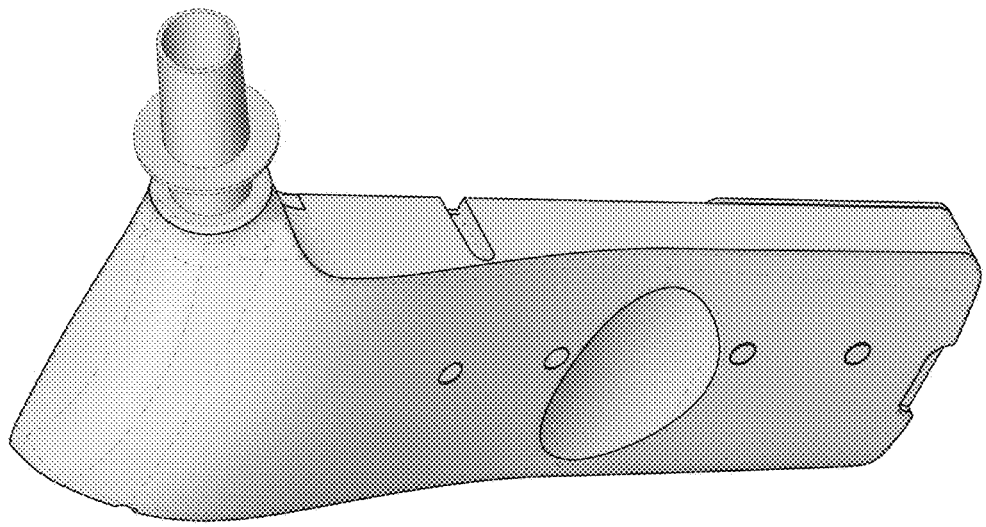
FIG. 29 is an isometric view of a cartridge. As can be seen in FIGS. 29-59, surface renderings are used to convey surface contouring and not texture; the Figures presented herein are not intended to convey any particular color distinctions or contrasts between components, and it is to be recognized that embodiments with a variety of different color schemes may fall within the scope of the depicted embodiments. Applicant reserves the right to changes this surface rendering into line shading and/or stipple shading. Additionally, it is to be understood that many of the surface intersections in the depicted FIGS. 29-59 may intersect such that a blended or lightly-rounded edge is formed. As such, there may be no "hard" edge present at such locations. A virtual edge may nonetheless be defined at such locations, as represented by a "tangent line" or "tangent edge" which are depicted as grey, dash-dot-dot lines in FIGS. 29-59. The tangent edges, for the sake of clarity, represent transitions between a surface and a rounded surface, i.e., where these two surfaces are tangent to one another. Applicant reserves the right to insert a virtual "hard" edge in between adjacent, matched pairs of tangent edges (as shown in various Figures throughout) if deemed necessary by the Office to clarify the drawings. It is to be understood that many of the rounded edges may appear, to the casual observer, to be hard edges due to the small radius of such rounded edges. Applicant also reserves the right to turn such tangent edges, in whole or in part, into solid lines, in part or in whole, in order to clarify any of the drawings; similarly Applicant reserves the right to turn any solid line, in whole or in part, into a tangent line, in part or in whole, in order to clarify any of the drawings. It is to be understood that any shading is provided to show contouring and should not be understood to indicate coloring or contrast between components.
Figure 35:
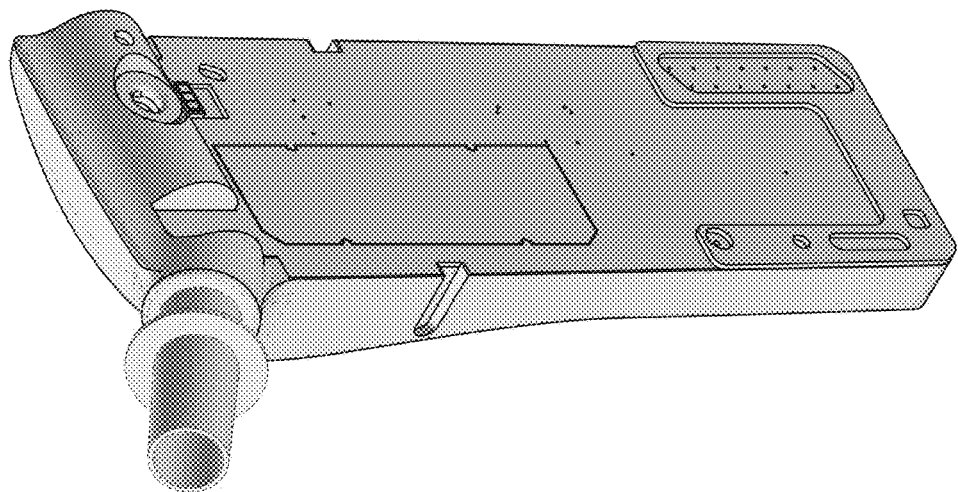
FIG. 35 is another off-angle view of the cartridge of FIG. 29.
Figure 34:
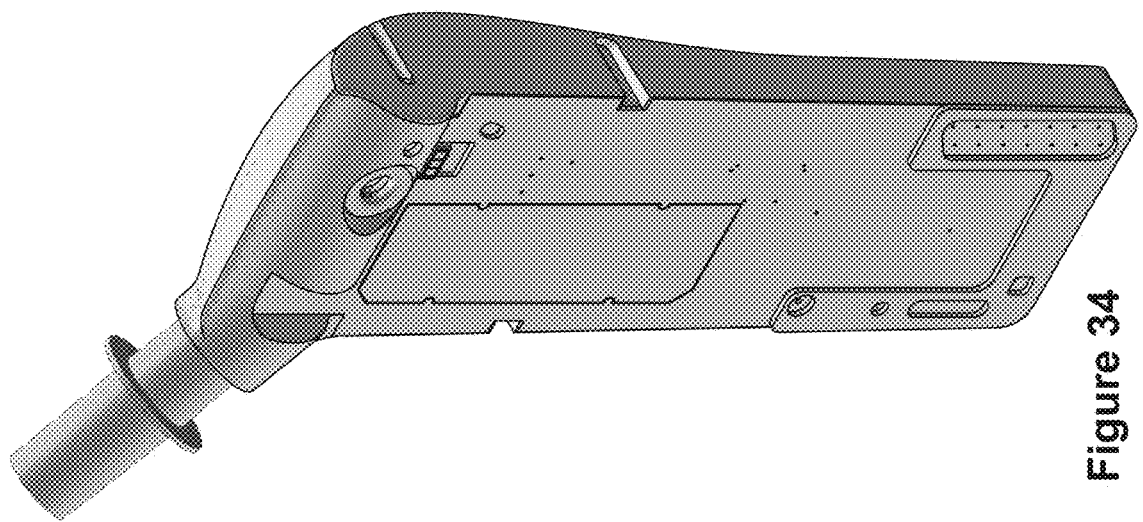
FIG. 34 is an off-angle view of the cartridge of FIG. 29.
Figure 33:
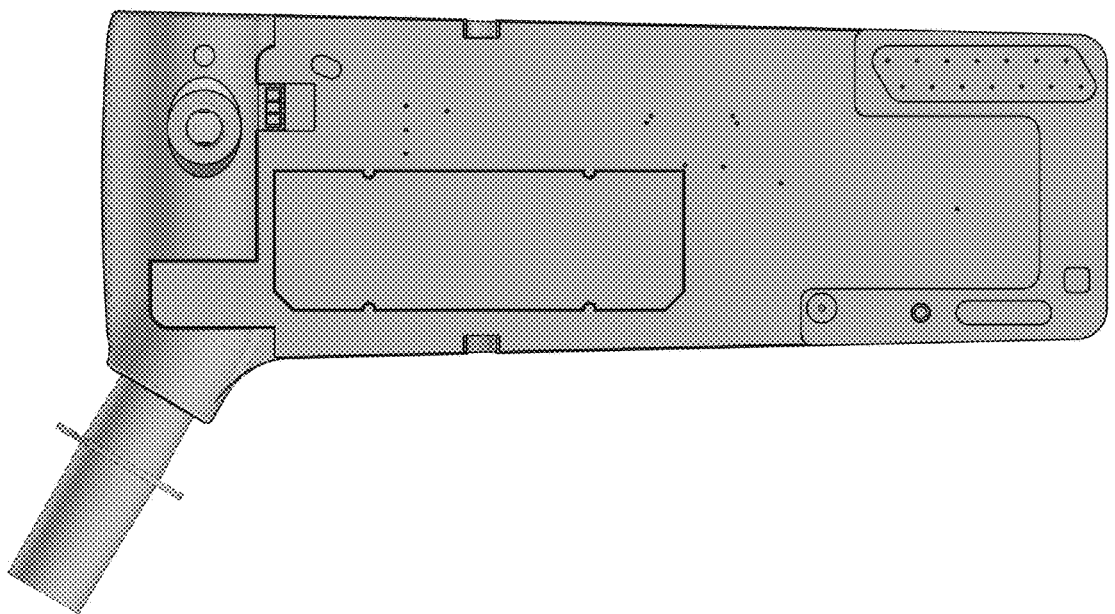
FIG. 33 is a back view of the cartridge of FIG. 29.
Figure 37:
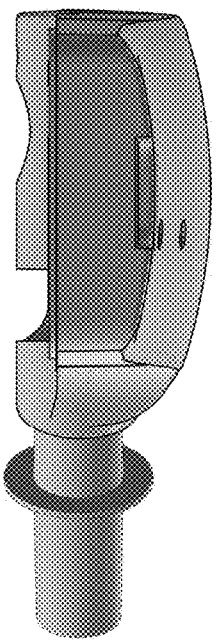
FIG. 37 is a bottom view of the cartridge of FIG. 29.
Figure 38:
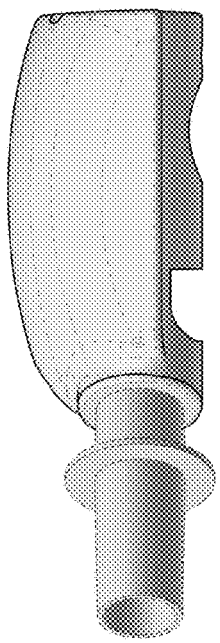
FIG. 38 is a top view of the cartridge of FIG. 29.
Figure 39:
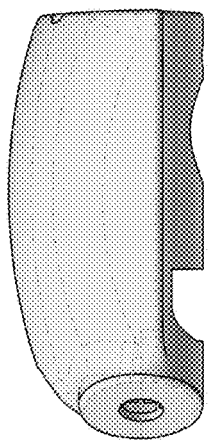
FIG. 39 is a top view of the cartridge of FIG. 29 without a removable mouthpiece.
Figure 36:
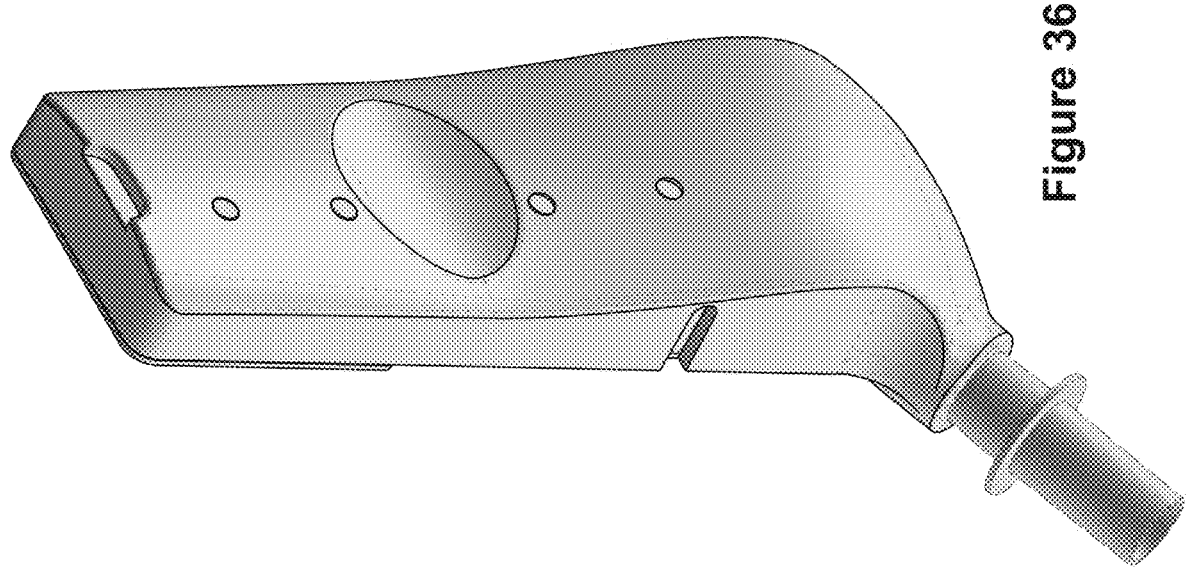
FIG. 36 is yet another off-angle view of the cartridge of FIG. 29.
Figure 42:
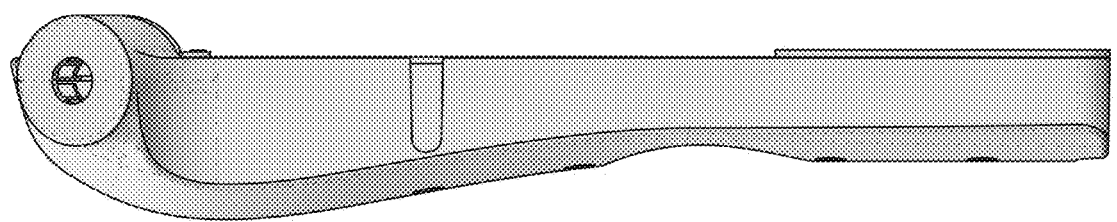
FIG. 42 is an off-angle view of the cartridge of FIG. 39 without the removable mouthpiece.
Figure 41:
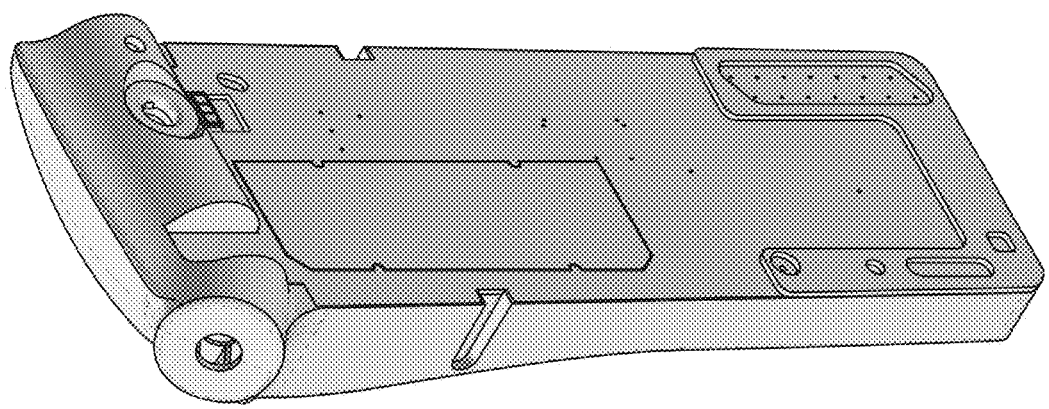
FIG. 41 is an off-angle view of the cartridge of FIG. 39 without the removable mouthpiece.
Figure 40:
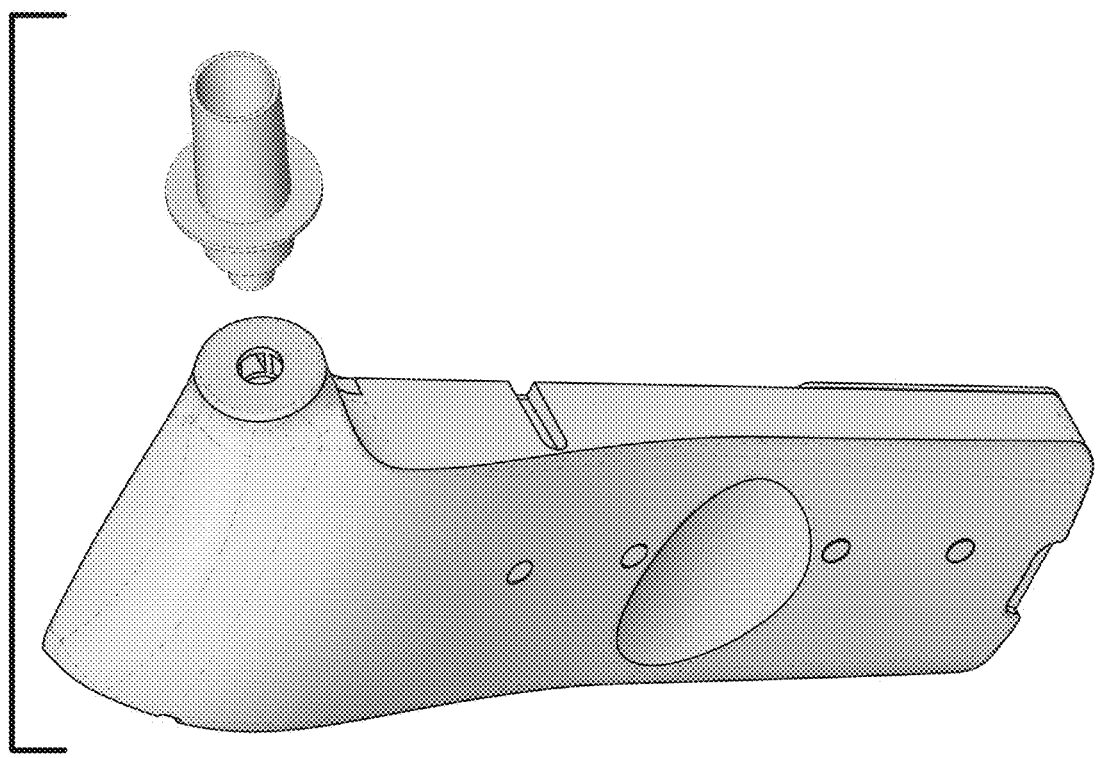
FIG. 40 is an exploded isometric view of the cartridge of FIG. 29.
Figure 45:
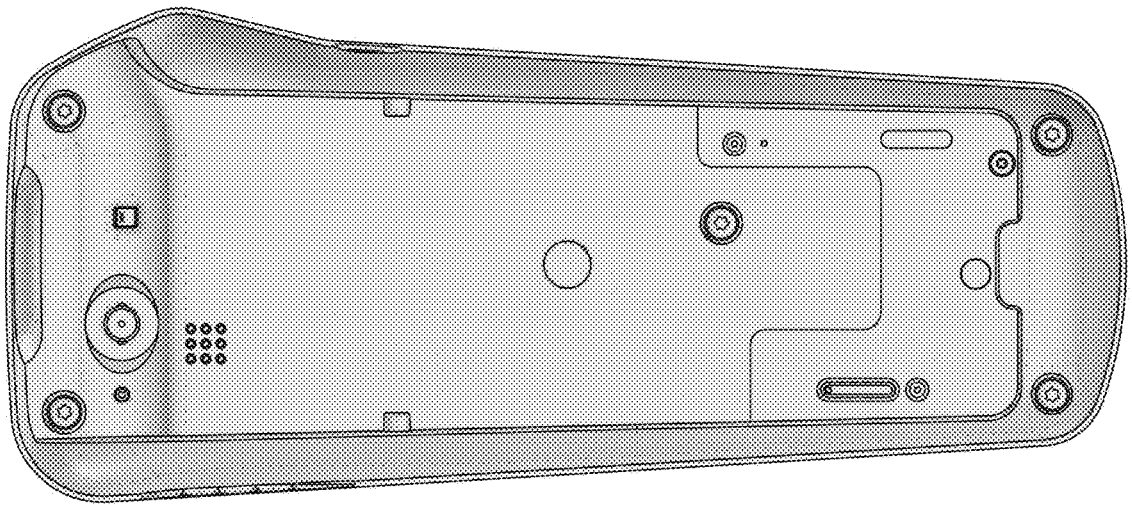
FIG. 45 is a back view of the handheld unit of FIG. 43.
Figure 44:
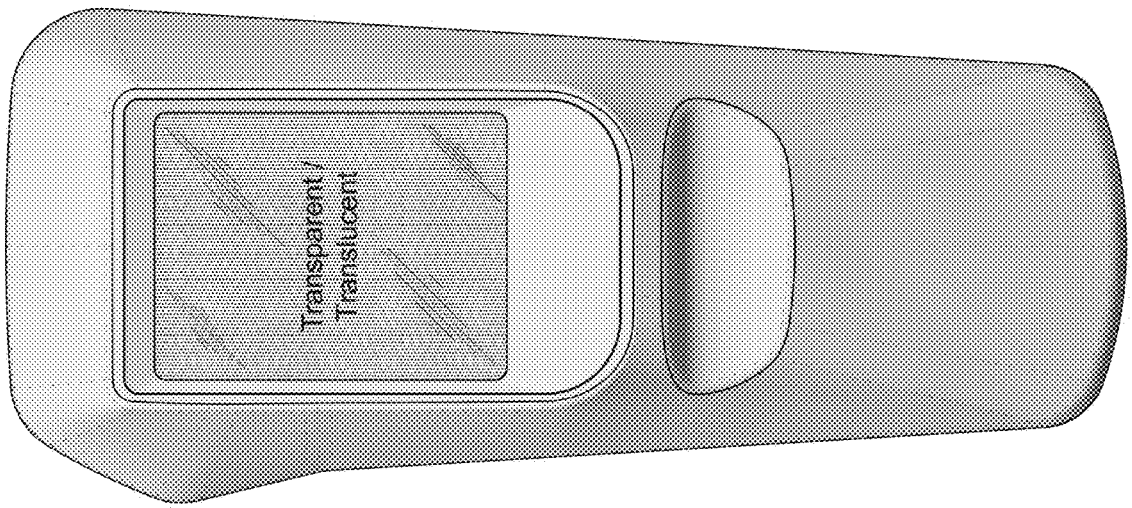
FIG. 44 is a front view of the handheld unit of FIG. 43; the handheld unit includes a screen that is transparent or translucent, as indicated in this Figure by shading and cross-hatching.
Figure 43:
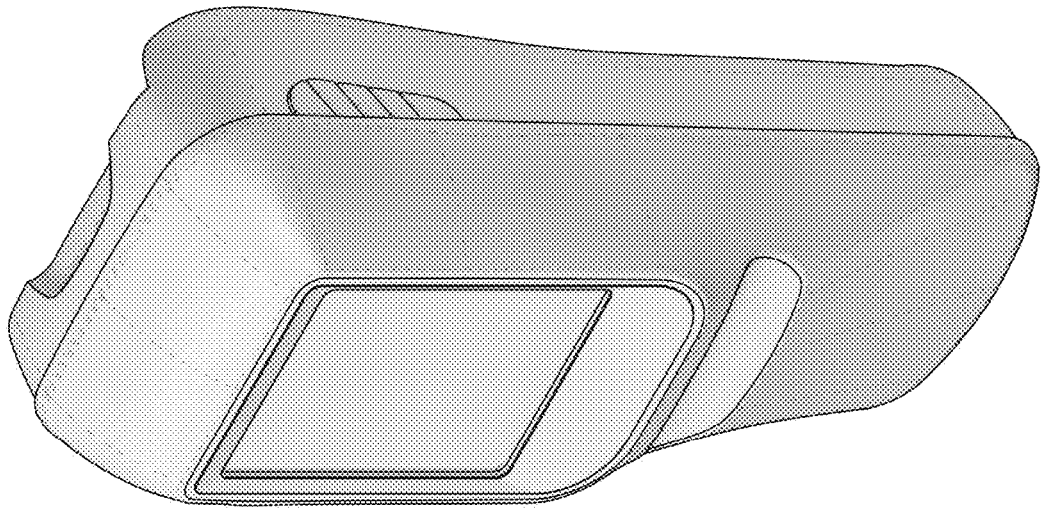
FIG. 43 is an isometric view of a handheld unit.
Figure 48:
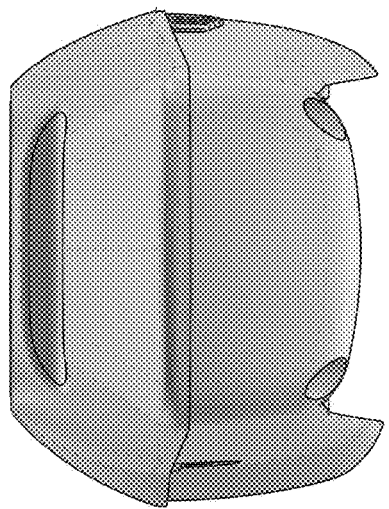
FIG. 48 is a bottom view of the handheld unit of FIG. 43.
Figure 49:
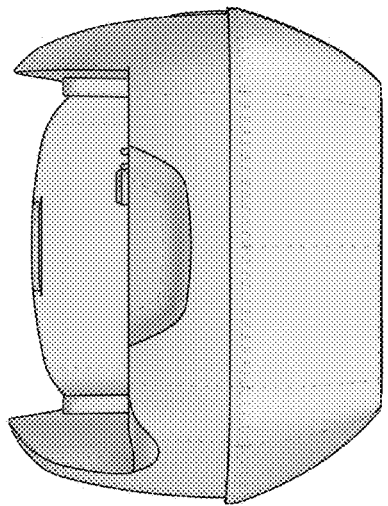
FIG. 49 is a top view of the handheld unit of FIG. 43.
Figure 47:
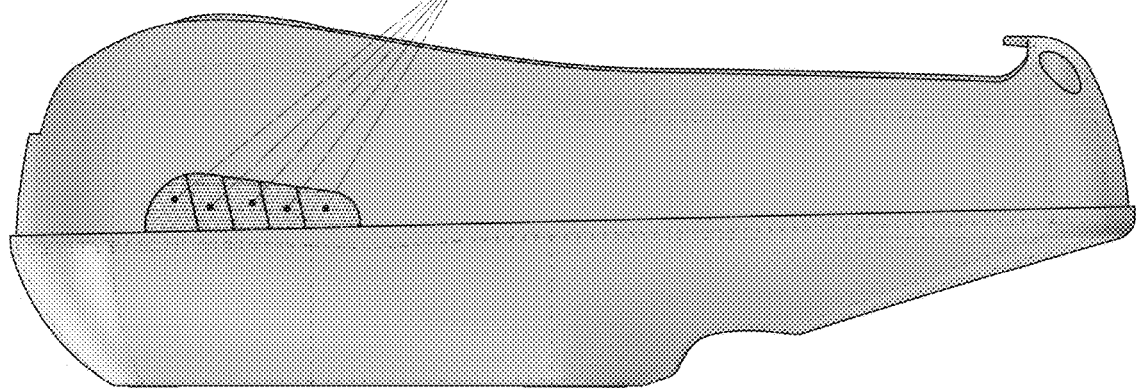
FIG. 47 is an opposite side view of the handheld unit of FIG. 43; the handheld unit includes five surfaces that may be transparent or translucent to allow light transmitted from within the handheld unit and below the surfaces to be emitted and seen outside the handheld unit.
Figure 46:
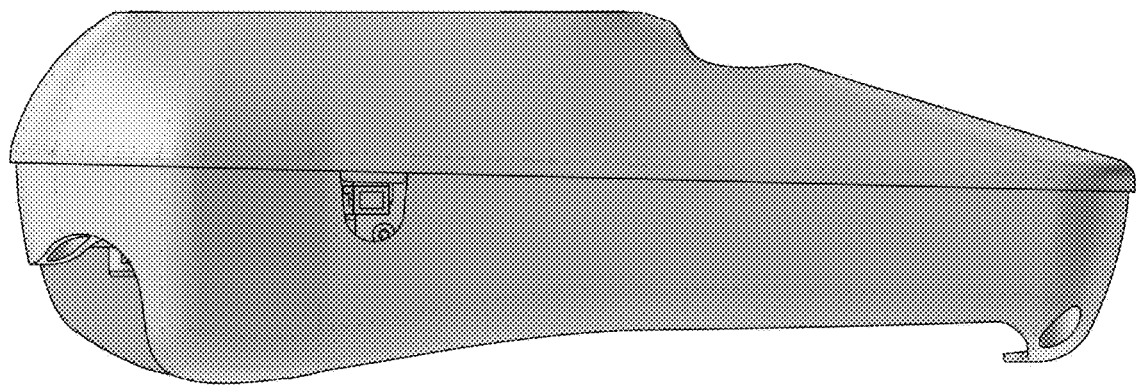
FIG. 46 is a side view of the handheld unit of FIG. 43.
Figure 52:
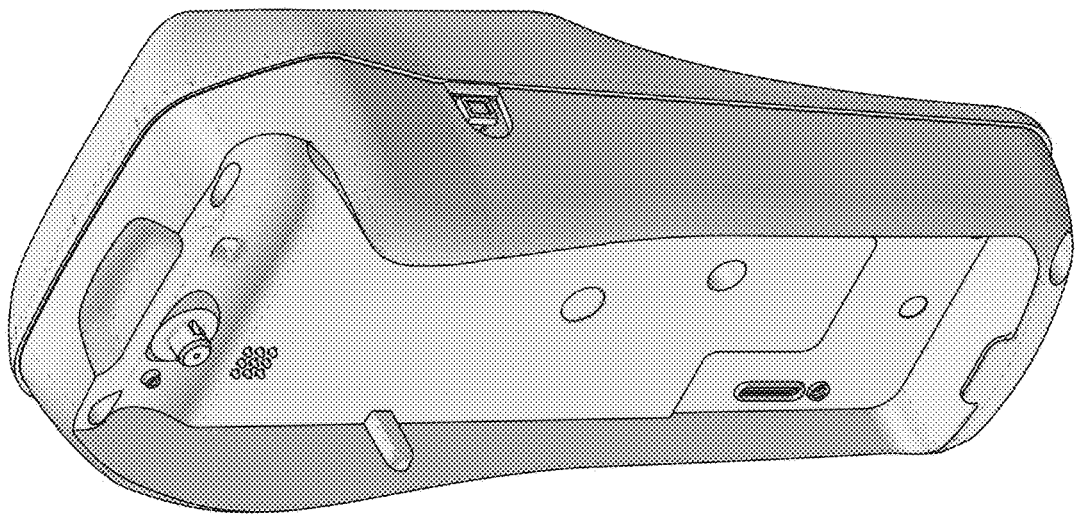
FIG. 52 is yet another off-angle view of the handheld unit of FIG. 43.
Figure 51:
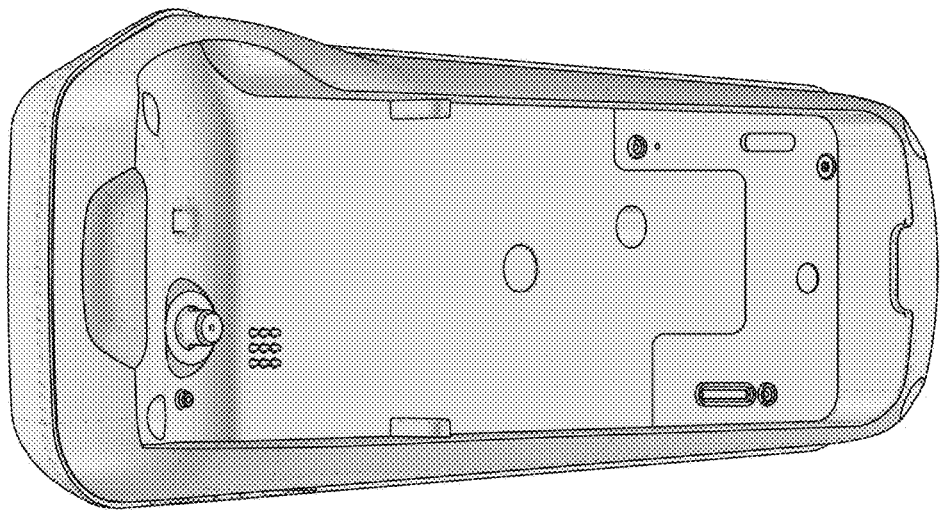
FIG. 51 is another off-angle view of the handheld unit of FIG. 43.
Figure 50:
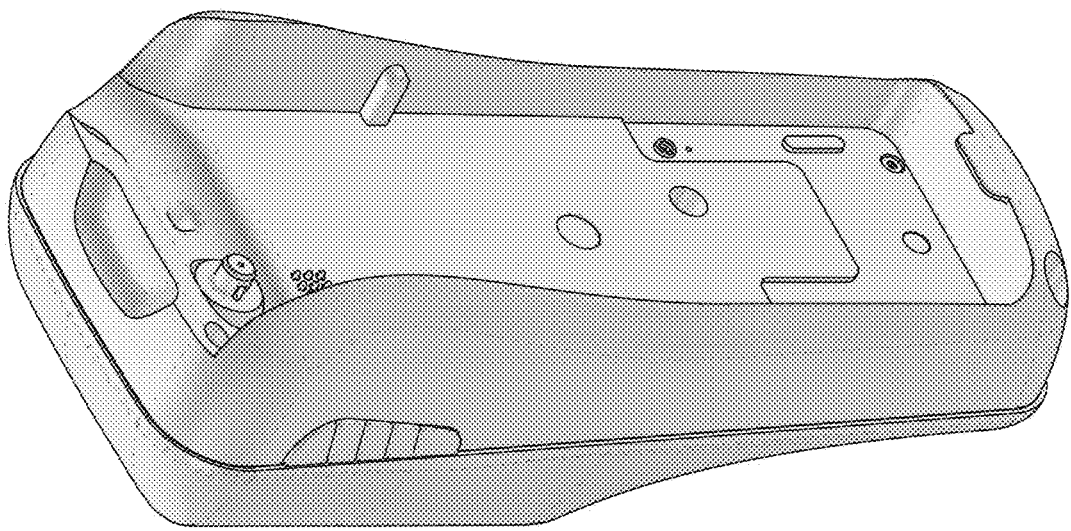
FIG. 50 is an off-angle view of the handheld unit of FIG. 43.
Figure 54:
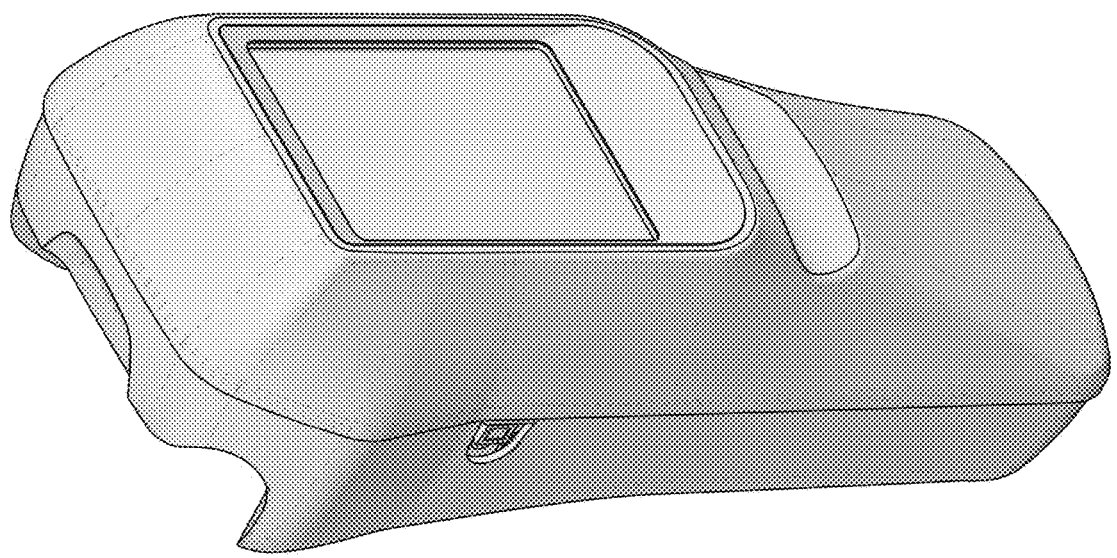
FIG. 54 is different off-angle view of the handheld unit of FIG. 43.
Figure 53:
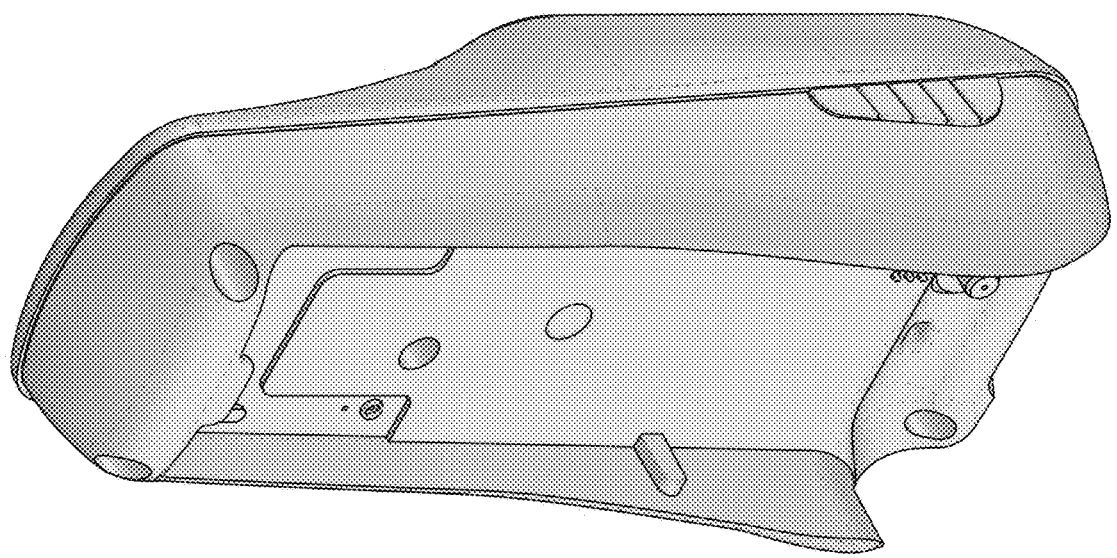
FIG. 53 is another off-angle view of the handheld unit of FIG. 43.
Figure 55:
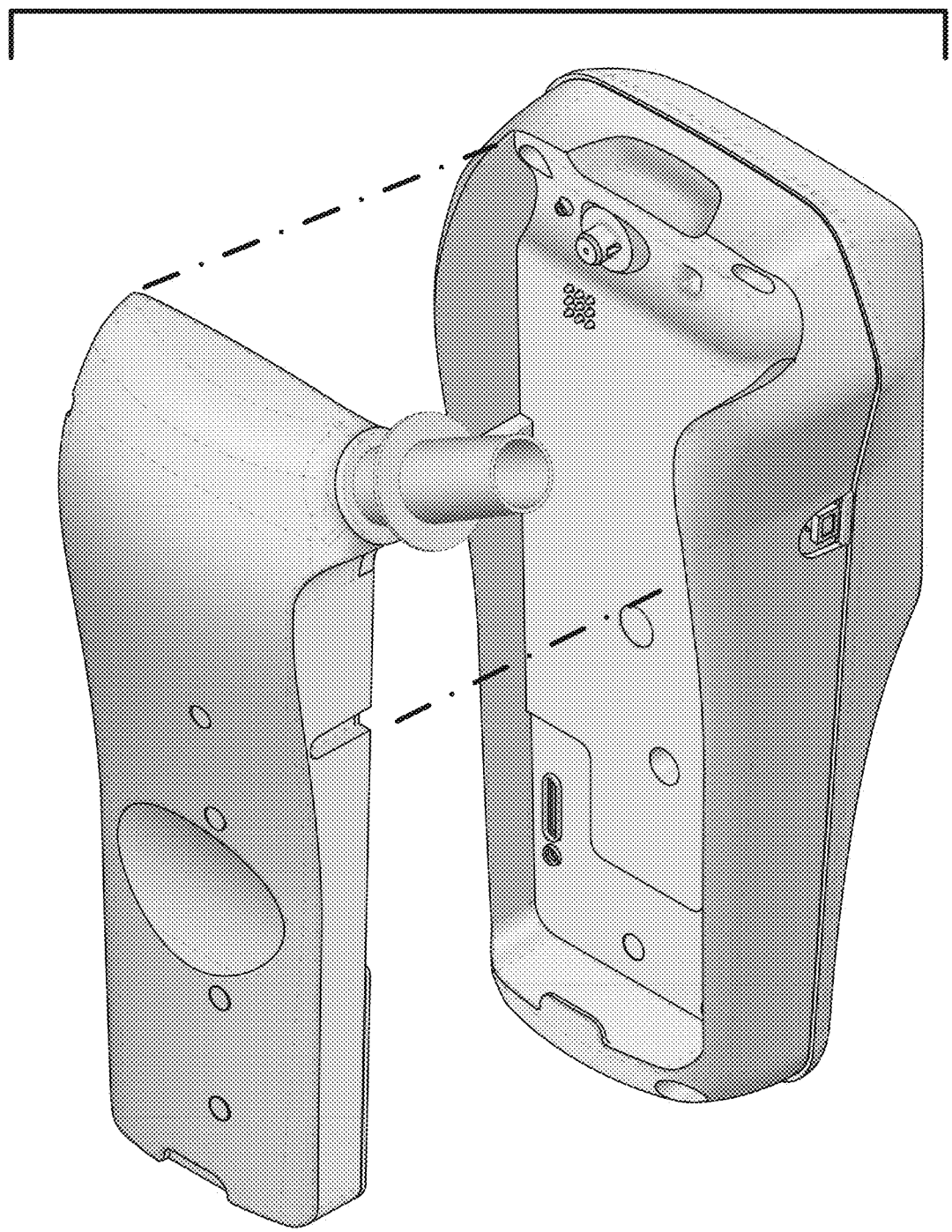
FIG. 55 is an exploded off-angle view of the cartridge of FIG. 29 and the handheld unit of FIG. 43.
Figure 56:
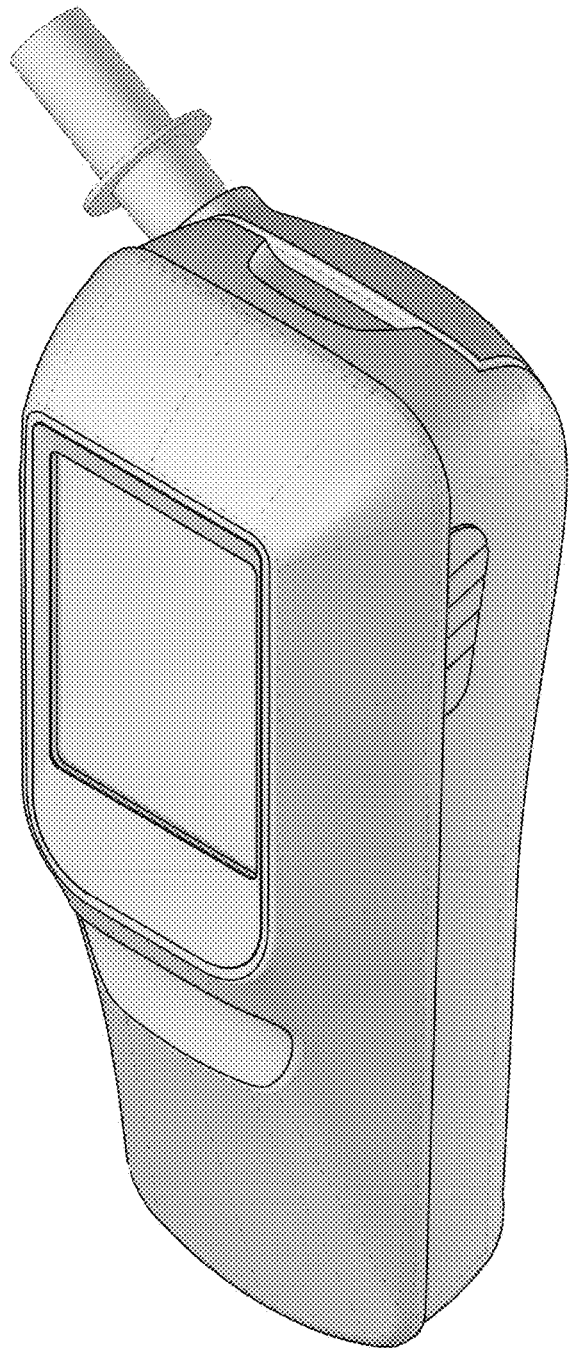
FIG. 56 is an isometric view of the cartridge of FIG. 29 inserted into the handheld unit of FIG. 43; the handheld and cartridge are configured to have the cartridge inserted into a recess of the handheld unit.
Figure 57:
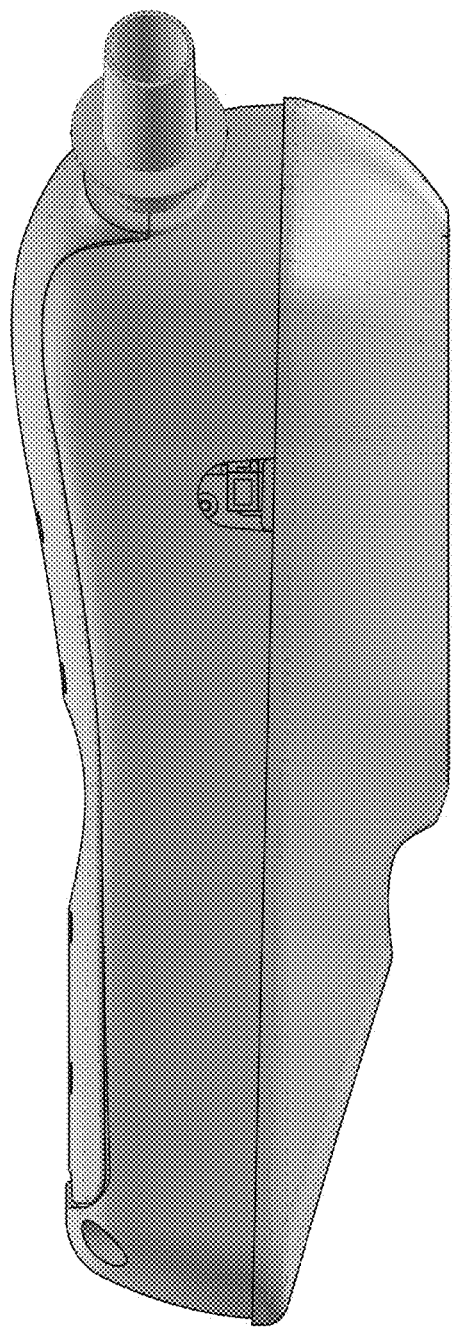
FIG. 57 is a side view of the cartridge and handheld of FIG. 56.
Figure 58:
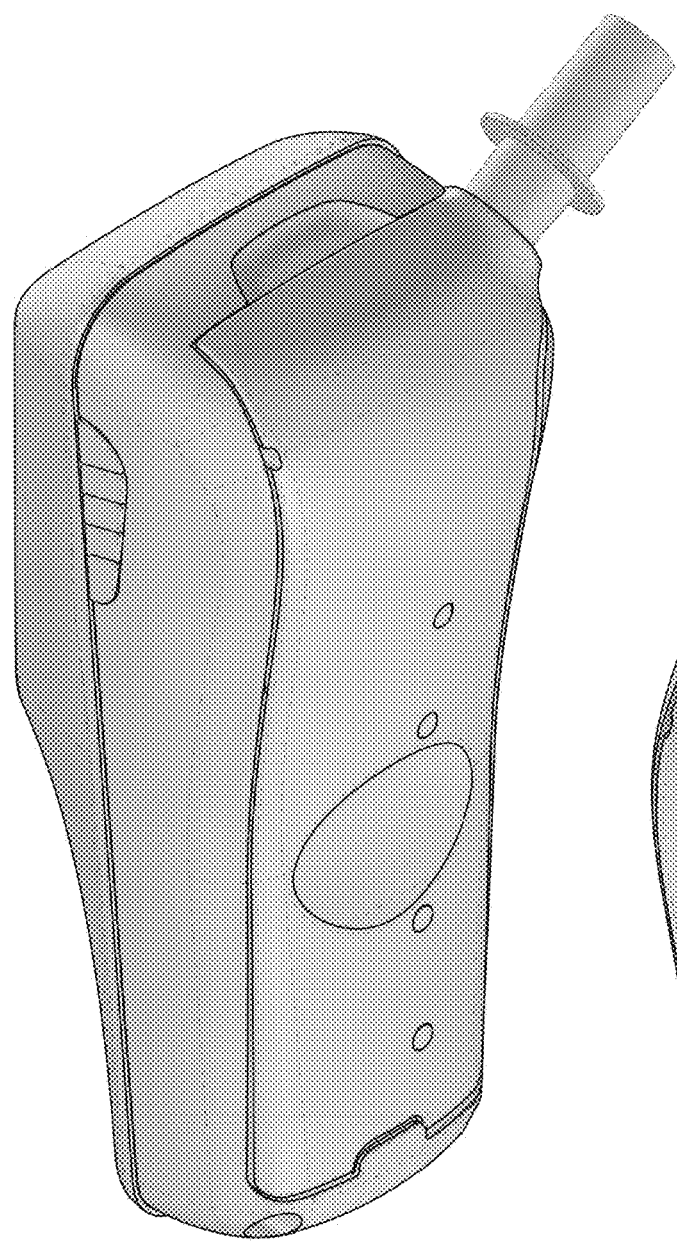
FIG. 58 is an off-angle view of the cartridge and handheld of FIG. 56.
Figure 59:
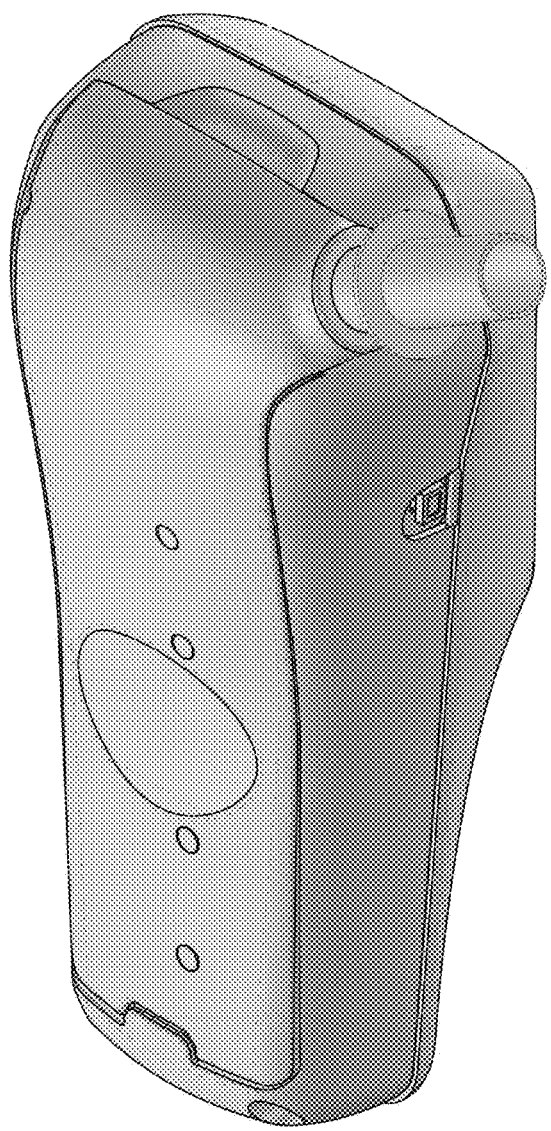
FIG. 59 is another off-angle view of the cartridge and handheld of FIG. 56.
Figure 63:
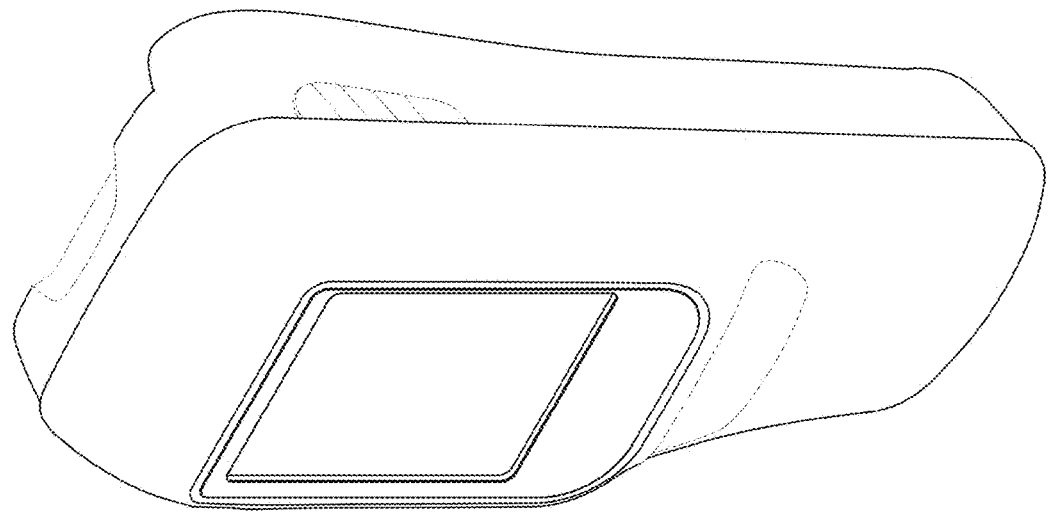
FIGS. 60-69 depict different views of the cartridge of FIGS. 30, 31, and 32, and of the handheld of FIGS. 43, 47, 50, and 52, respectively, but with various lines changed to broken lines to indicate that such lines are disclaimed subject matter. The shading and tangent lines have been removed for ease of viewing. Applicant reserves the right to change any solid line, in whole or in part, to a broken line in any of the Figures depicted herein and to place such boundaries in any locations in any of the embodiments depicted herein. For example, the mouthpiece of the cartridge may be disclaimed or removed, and various features of the handheld unit, including the five surfaces, screen, and features on the back, may be disclaimed in whole or in part.
Figure 62:
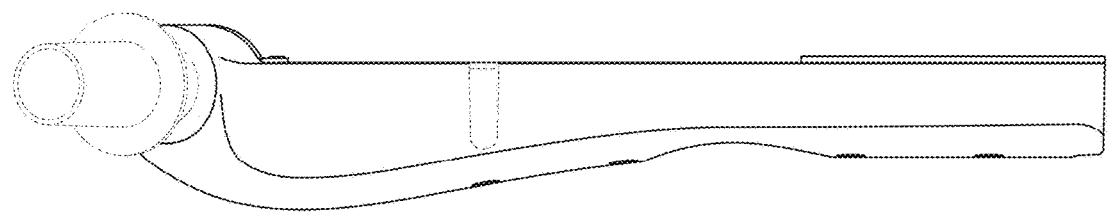
Figure 61:
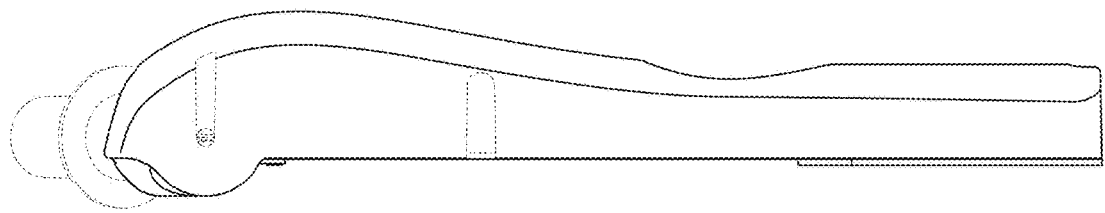
Figure 60:
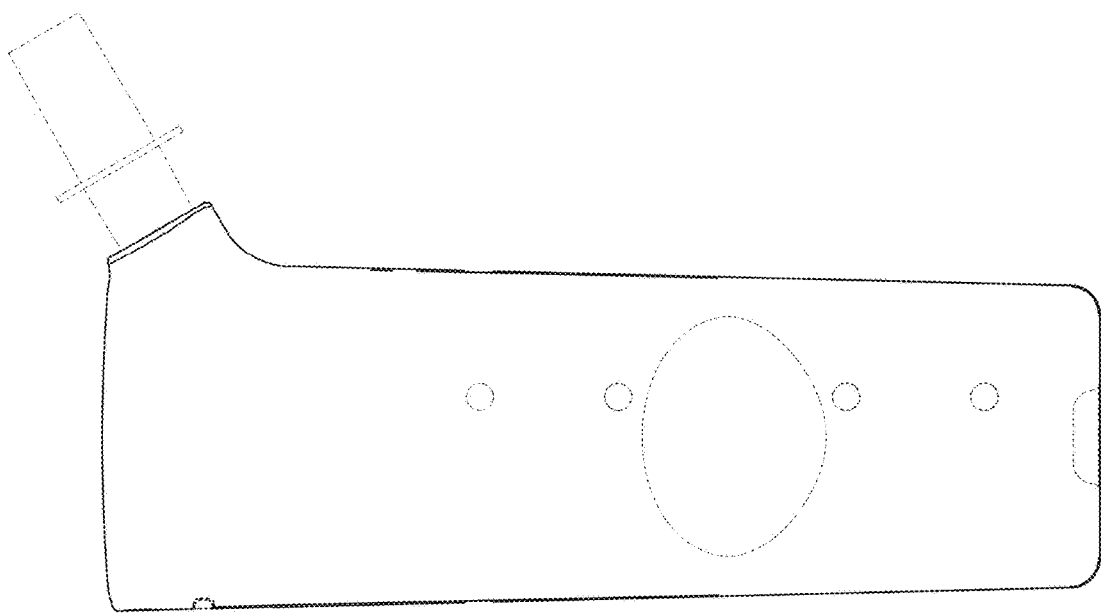
Figure 66:
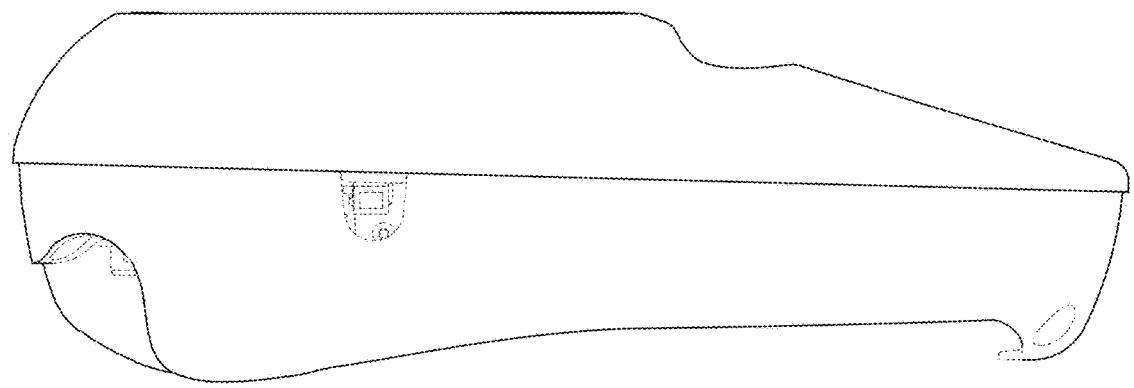
Figure 65:
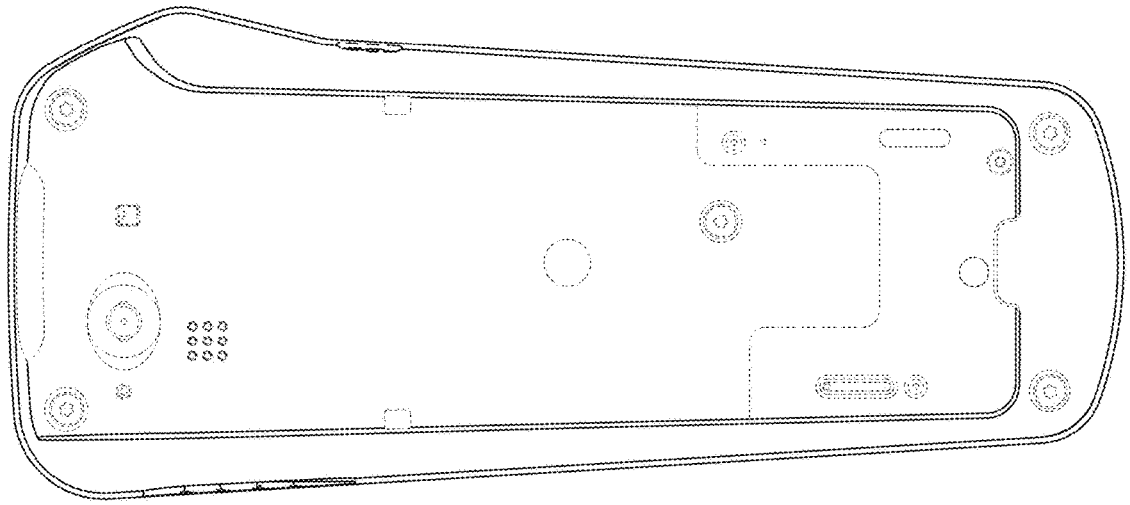
Figure 64:
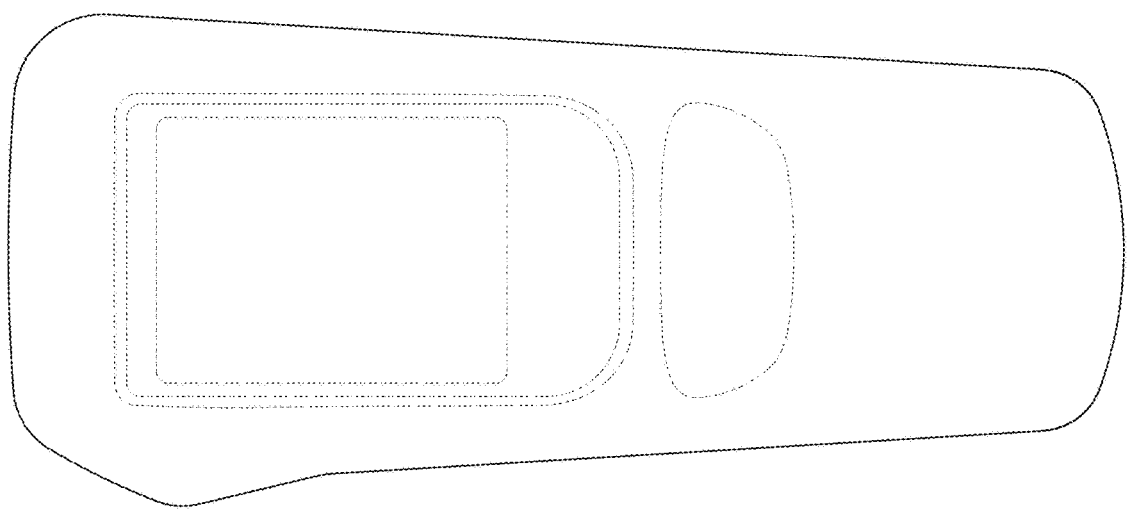
Figure 69:
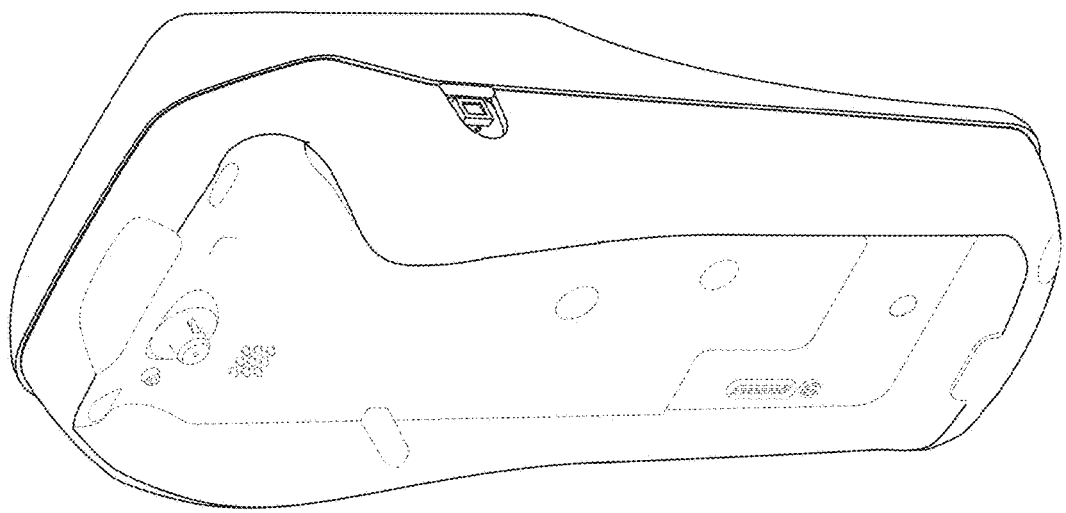
Figure 68:
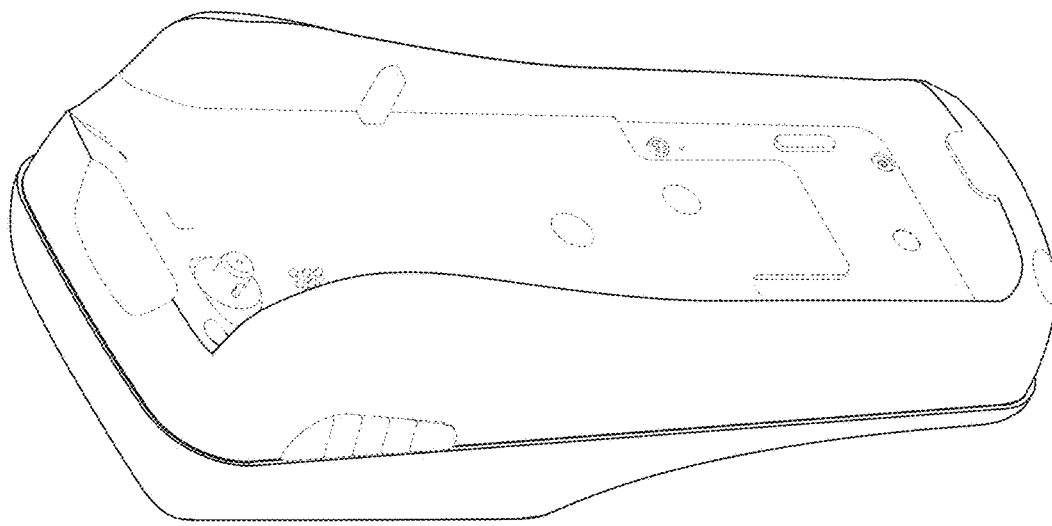
Figure 67:
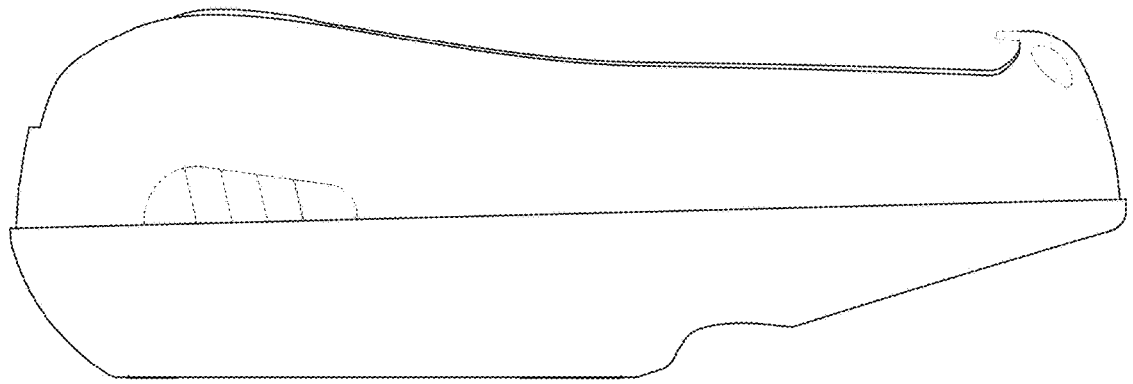
Figure 70:
FIGS. 70-73 depict various graphical user interfaces (GUIs) that may be displayed on a display of the hand-held unit described above. Each Figure includes a plurality of such GUI interfaces, each generally occupying a rectangular space (FIGS. 70 and 72 have 16 such GUIs each, FIG. 71 has 9 GUIs and several graphical sub-elements of GUIs (circles, a check box), FIG. 73 has 11 GUIs). Applicant reserves the right to render any of the depicted GUIs in line-drawing format, e.g., by inserting lines in any location where there is a transition from one color to another, and to remove the coloring shown so as to produce black and white line drawings.
Figure 71:
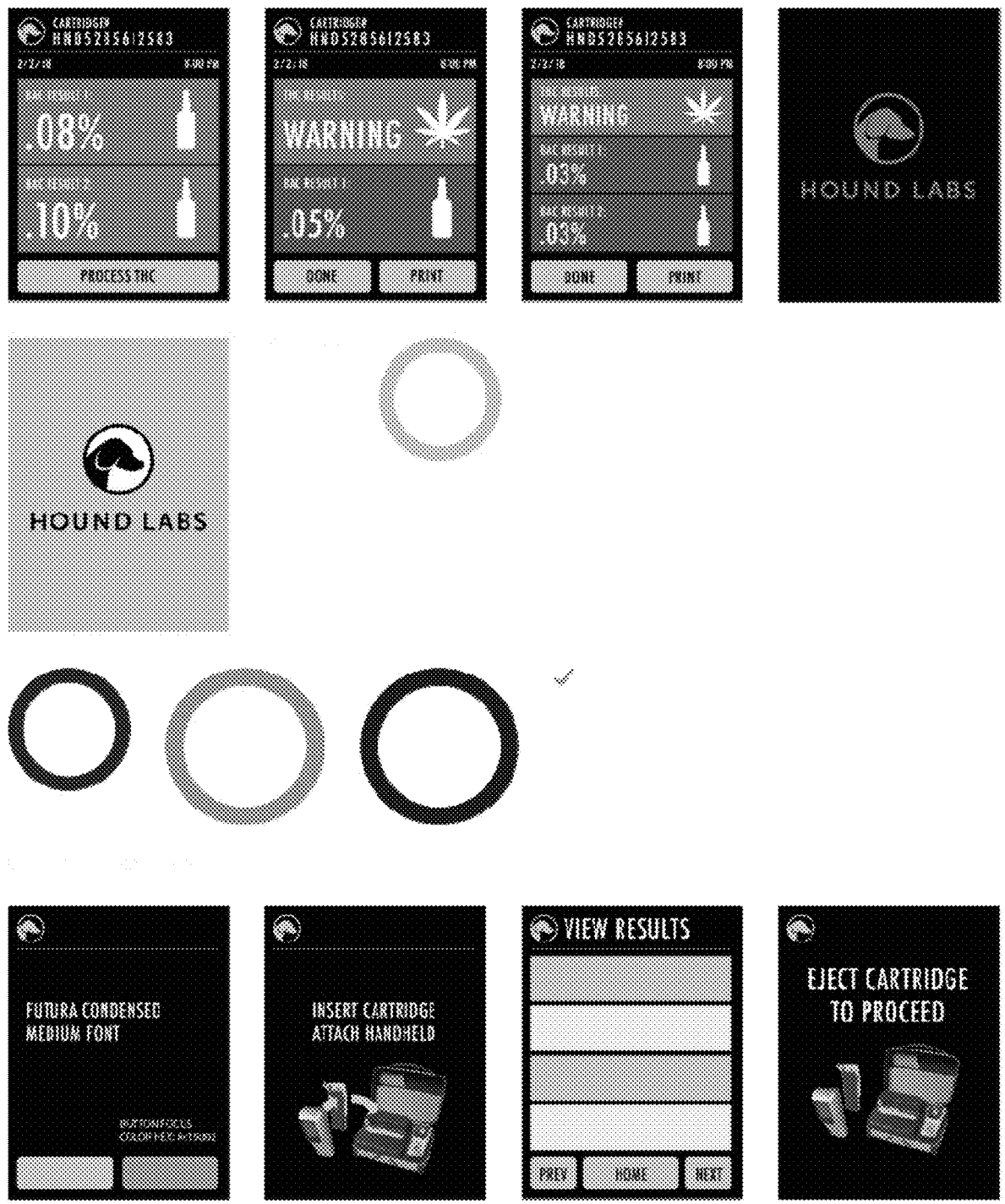
Figure 72:
Figure 73:

For the sake of completeness, some example operational flows that may serve as a functional framework for operation of portions of an example breath sampling and analysis system are discussed below with reference to FIGS. 27 and 28. FIG. 27 depicts an example breath sampling technique. FIG. 28 depicts an example breath sample analysis technique using an insertable cartridge.

In FIG. 27, the technique begins in block 2702. In block 2704, the start of a breath sample collection event may be detected. In some implementations, this may be detected based on user inputs, e.g., a user may push a button on a breath sampling device or may select an on-screen control on a touch-sensitive display in order to initiate a breath sample collection event. In other implementations, the start of a breath sample collection event may be detected based on sensor input, e.g., when a pressure sensor in the collection device detects a pressurization event consistent with the pressure increase that may be experienced due to a subject exhaling into the collection device. In block 2706, a determination may be made as to whether a breath sample collection event has started; if not, the technique may return to block 2704 to check again if a breath sample collection event has started. If so, the technique may proceed to blocks 2708, 2710, and, optionally, 2712. In block 2708, reaction channels, within a microfluidic plate in the collection device, e.g., a cartridge as discussed earlier herein, may be unsealed by actuating isolation valves within the microfluidic plate so as to allow the air sample to be flowed through the reaction channels. In block 2710, the reaction channels may optionally have a vacuum assist applied to them to generate an increased pressure differential between the reaction channels and the flow path, e.g., a plenum of the cartridge, through which the breath sample reaches the reaction channels. Such a vacuum assist may, as discussed earlier, increase the flow rate of breath sample through the reaction channels. If the vacuum assist functionality is used, the vacuum assist may be activated after the isolation valves are opened in some implementation (or, in some addition implementations, concurrently with opening the isolation valves).

In implementations in which the same breath sample is used to obtain both a breath sample for analyte detection and/or measurement and, for example, a blood alcohol reading, a portion of the breath sample may be diverted through a blood alcohol sensor, e.g., a fuel-cell type blood alcohol sensor. The blood alcohol sensor reading may proceed in parallel with collection of the breath sample for later analyte analysis and measurement.

In block 2714, the flow rate of breath sample through the reaction channel(s) may be monitored to determine how much breath sample volume has passed through the reaction channels. In some implementations, a flow sensor, e.g., a mass flow rate sensor, may measure the amount of breath sample that is pumped by the vacuum pump used to provide vacuum assist during breath sample collection. In some implementations, the fluidic flow from the reaction channel(s) may be split downstream of the reaction channels so that one portion of the breath sample flows through the flow sensor to measure the flow rate and the other portion of the breath sample bypasses the flow sensor. In such implementations, both flow paths may have flow restrictions that cause the breath sample portions that flow through each to be in a fixed proportion to one another, e.g., equal-sized flow restrictors may be used to ensure that the flow sensor and the bypass experience equal flow rates (or otherwise constant predetermined flow rate ratios) during normal operation of the breath sample collection device. In such implementations, the flow sensor data may represent only a known portion of the total flow rate through the reaction channels, and the total flow rate through the reaction channels may be determined by multiplying the measured flow rate by the inverse of the percentage of the flow that passes through the flow sensor. In block 2716, a determination may be made as to how much breath sample has flowed through the reaction channels. Once the flow sensor data indicates that a desired amount of breath sample, e.g., 0.5 liters per reaction channel, has flowed through the microfluidic plate, the technique may proceed to blocks 2720 and 2722, in which, respectively, the vacuum assist, if used, may be deactivated and the isolation valves may be closed to seal the reaction channels. If it is determined in block 2716 that the amount of breath sample flowed through the reaction channels is less than the desired amount, the technique may return to block 2714 for further monitoring of the flow rate. In some such implementations, the data from the flow meter may optionally be used to update a progress indicator in block 2718, e.g., to update a display showing the amount (or relative percentage) of breath sample collected, provide audio cues indicating sample collection progress, and/or cause one or more progress indication lights to illuminate.

As discussed, in block 2720, the vacuum assist may be deactivated. As discussed earlier herein, the vacuum assist may, in some implementations, also be temporarily deactivated when data from a pressure sensor monitoring the plenum of the cartridge through which the breath sample is flowed indicates that the subject is no longer exhaling through the cartridge at a predetermined level.

In block 2724, environmental and subject data may be obtained and, in block 2726, stored on a memory device. It will be understood that some such data may be obtained and/or stored at any of a variety of times, e.g., immediately before sample collection, during sample collection, and/or after sample collection. Such data may include information relating to subject vital statistics (name, age/birthdate, gender, height, weight, driver's license number, etc.), environmental conditions at the time the sample was obtained (temperature, humidity, time, location, etc.), and operational information (duration of sample collection time, amount of breath sample flowed through reaction channels, etc.). If a blood alcohol measurement is obtained concurrently with breath sample collection, the blood alcohol measurement may be stored in the memory device as well in block 2728. Once data storage, if performed, is complete, the technique may end at block 2730.

Once a breath sample has been successfully collected, the collected breath sample may be analyzed, e.g., using any of a variety of techniques, as discussed elsewhere herein. One such example analysis technique is discussed below with respect to FIG. 28.

The technique may begin in block 2802. In block 2804, the insertion of a cartridge into the analysis instrument may be detected (assuming that a cartridge is used). Once cartridge insertion is detected, a cartridge loading operation may be performed in block 2806. Such loading may, for example, secure the cartridge within the instrument and may ensure that the cartridge is properly interfaced with components in the analysis instrument, e.g., pneumatic control ports for transferring pneumatic control signals to valves and pumps within a microfluidic plate of the cartridge, electrical connections to components on the cartridge (e.g., memory devices), etc.

In block 2808, force may be applied to the cartridge so as to compress the cartridge against a heat spreader plate or other potential heat source to provide good thermal contact between the cartridge and such a heat source. The application of the thermal contact load may be performed as part of block 2806, and may be optional if no pre-heating of the cartridge is to be performed or if the analysis instrument does not include such cartridge pre-heating functionality, such as may be the case for instruments intended for use in controlled environments, such as laboratories.

In block 2810, a heater may optionally be used to heat the cartridge, e.g., heat from the heater may be transferred to the cartridge via a heat spreader plate. In some implementations, the cartridge may be heated by flowing warm air around and/or through the cartridge. For example, the cartridge may flow paths through the cartridge that allow warm air to be flowed through it such that any potentially frozen liquid reservoirs are exposed to the warm air, thereby allowing the frozen liquid to be thawed. In such convective heating arrangements, the thermal contact loading from block 2808 may be omitted.

In block 2812, if the heater is used, a predetermined amount of time may be allowed to elapse to allow for adequate heating and thawing of any potentially frozen liquids in the cartridge. Such an amount of time may be fixed, e.g., 2 minutes, or may be dynamically adjusted based on feedback from sensors in the cartridge, e.g., if temperature sensors that may optionally be included in the cartridge indicate temperatures that are above a predefined threshold, then a determination may be made that whatever liquids are present in the cartridge are in a liquid state.

Once the cartridge is loaded in block 2806 and any heating-related operations, if any, are performed, the cartridge liquids may be prepared for use in block 2814. For example, in implementations in which various liquids used during the analysis operations are stored in blisters or other long-term storage containers within the cartridge, such liquids may be forced or drawn from such containers and stored in reservoirs that are fluidically connected with the microfluidic plate of the cartridge so that the pumps within the microfluidic plate may cause such liquids to be transported between various locations in the microfluidic plate. Since cartridges may be stored for extended periods of time before being used, liquids that are housed within the cartridge and intended for use in analysis may be stored in long-term storage containers such as the blisters discussed earlier herein to avoid leakage and possible contamination of the liquids. The blisters, for example, may be flexible pouches made from a material that is chemically non-reactive with the liquid contents and that are fluidically connected with fluid flow channels in the microfluidic plate by valves, e.g., rupture, relief, pop-off valves, or the like, that fluidically isolate the blister contents from the microfluidic plate until the contents of the blisters are pressurized to a predetermined level, e.g., by compressing the blisters sufficiently. It will be recognized that other types of long-term storage may be used as well, including storage in sealed glass ampoules where needles are inserted in order to withdraw liquids therefrom. In some implementations, the cartridge may not store any liquids and such liquids may instead be stored within the instrument itself and then transferred to the cartridge via ports on the microfluidic plate, similar to how pneumatic pressure/vacuum is communicated to the microfluidic plate.

Such liquid dispensation from long-term storage containers may be performed, as discussed earlier herein, using a gear-driven press or other compression device, or may be performed with other mechanisms. In implementations where the liquids are already stored in locations that are fluidically connected with the microfluidic plate to begin with, the operations of block 2814 may be omitted if unnecessary.

Once the liquids used during sample preparation and analysis have been staged at appropriate locations within the cartridge, e.g., within reservoirs accessible to the valves, flow channels, and pumps within the microfluidic plate, sample preparation may begin.

In some implementations, some liquid reagents may be stored separately to prevent premature reaction between such reagents. The compound or chemical resulting from such reactions may be necessary in order to perform the analysis, but may have a very limited window of time within which it is stable. In such situations, pumps (and valves, if necessary) of the microfluidic plate may be operated in block 2816 to pump the liquid reagents that are stored separately for long-term storage into a common mixing reservoir so that they can mix to produce the reagent needed for analysis. For example, if a substrate is used during analysis is stored in binary form, the two different portions of the substrate may be pumped into a common reservoir to allow them to mix and form the substrate.

Similarly, in implementations in which some analysis components or reagents may be stored in a lyophilized format, e.g., freeze-dried antibodies, or other non-liquid format, e.g., dried, pulverized diazofunctionalized fluorophoric indicator, one or more pumps (and valves, if necessary) may be actuated in block 2818 to cause an appropriate reconstitution liquid to be flowed from the appropriate reservoir to a reconstitution reservoir containing such non-liquid components. For example, a pump (and valves, if necessary) within the microfluidic plate may be actuated to transfer a liquid buffer from a buffer reservoir to an antibody reservoir containing a lyophilized antibody.

The preceding operations may generally be performed for any of a variety of different analysis protocols, as such operations relate to simply preparing the various types of liquids and reagents that may be used during any given analysis (some protocol-specific examples are given, but the overall steps taken may generally be relevant to a large variety of different protocols). The specific steps discussed below, however, may be different depending on which analysis protocol is actually used. In the interests of conciseness, the technique set forth in the discussion below uses an example protocol similar to that discussed earlier in this disclosure involving a competitive immunoassay. It will be recognized that alternative approaches may use other types of analysis, e.g., diazofluorophore-based analyses, non-competitive immunoassays, etc.

In block 2820, a solution containing reconstituted antibody, as may be produced after the operations of block 2818 are performed for a reservoir containing lyophilized antibody and a suitable reconstitution time is allowed to elapse, e.g., 20-30 seconds, may be dispensed to each of the reaction channels having contents to be analyzed, e.g., a reaction channel containing breath sample as well as reaction channels containing control amounts of analyte.

In block 2822, the antibody solution that was delivered to each of the reaction channels in block 2820 may be allowed to incubate for a predetermined period of time, e.g., 60-70 seconds, to give the antibodies within sufficient time to bind to target antigens, if present, in each reaction channel. Such antigens may include, for example, the analyte that is present in the collected breath sample (or control amounts thereof that are within reaction channels designated as containing control amounts of analyte) as well as antigens that may be immobilized on the surfaces of each reaction channel.

After sufficient incubation time has elapsed, the antibody solution that is present within each reaction channel may be flushed away in block 2824, e.g., by pumping air through each reaction channel, followed by buffer or other suitable cleaning liquid, followed by a further purge with air. In this example, this has the effect of not only removing the antibody solution, but also all or nearly all of the analyte (from the breath sample or the controls) that is present within each reaction channel—only the antibodies that have bound to the immobilized antigen will generally remain in each reaction channel after such an operation.

After block 2824 is performed, a substrate, e.g., such as a substrate mixture/solution that may be created in block 2816, may be pumped into each of the reaction channels. The substrate may then be allowed to incubate in the reaction channels in block 2828 in order to allow the substrate to be activated by, for example, enzymes that may be conjugated with the antibodies that are bound to the immobilized antigen within each channel. Such incubation may, for example, occur for a period of approximately 60 seconds in some implementations.

After sufficient substrate incubation time has elapsed, analysis of the contents of each reaction channel may be performed. In block 2830, the substrate from a reaction channel may be pumped to an optical measurement site. In block 2832, an optical measurement of the substrate at the optical measurement site may be obtained, e.g., by measuring the intensity/amount of luminescence (which may be done in an otherwise dark environment to prevent light contamination). In other implementations, a fluorescent substrate may be used that must be stimulated, e.g., by exposure to light of a particular wavelength, in order to produce light, e.g., light of a wavelength other than the stimulation wavelength).

In block 2834, data relating to the measurement performed in block 2832 may be stored, e.g., in a memory device, for later retrieval. In some implementations, the timestamp for when the analysis/measurement was performed may be compared against a similar timestamp that was stored on the memory and that indicates when the breath sample in the cartridge was collected. In some such instances, if a period of time in between the two timestamps is too high, the cartridge may be flagged as potentially having compromised sample material, e.g., material that may have leaked out to some degree, or that may have been contaminated over time (the microfluidic valves used in microfluidic plates may generally have small gaps in them when unpressurized, allowing for some small degree of leakage—for collected breath samples, this may be of little immediate concern since the analytes are adsorbed onto the walls of the reaction channels, but if sufficient time passes, there may be diffusion/leakage through the unpressurized valves, which may introduce contaminants or allow breath sample to leak out; if the cartridge is analyzed soon after the sample is obtained, however, the risk of this may be reduced or minimized). In some implementations, the base station may be configured to refuse to analyze a cartridge with a breath sample that was collected more than a predetermined amount of time beforehand.

In block 2836, a determination may be made as to whether there are additional reaction channels with substrate to be analyzed/measured. If there are, then the technique may return to block 2830 and an additional pumping operation may be performed to move the substrate from a different reaction channel to the optical measurement site for analysis/measurement.

If there are no additional reaction channels with unmeasured substrate remaining to be measured, then an analysis result may be determined in block 2838, stored for later use, and/or displayed to a user. Such a result may be based, for example, on optical measurement data obtained for the contents of the reaction channel used for breath sample collection as well as the reaction channels having the control amounts of the analyte. As discussed earlier, the control amounts of analyte may be used to establish a relative scale for the optical measurements that allows the optical measurement of the breath sample reaction channel contents to be correlated with an amount of analyte in the breath sample based on the known amounts of analyte in each control.

Those of skill in the art will appreciate that the foregoing method descriptions and process flow diagrams are provided merely as illustrative examples and are not intended to require or imply that the steps of the various embodiments must be performed in the order presented. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope embodiments.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

The functions in the various embodiments may be implemented in hardware, software, firmware, or any combination thereof. If implemented in software, the functions may be stored as one or more processor executable instructions or code on a non-transitory computer readable medium or non-transitory processor readable medium. The steps of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

EXAMPLES

The following examples provide additional contextual and supporting material relating to the subject matter of this disclosure. The information presented in these examples should be understood to in no way limit the generality of this disclosure.

Example 1

A summary of a general method for estimating diagnostic performance of a qualitative assay (sensitivity/specificity) from analytical performance of the assay and distribution of true clinical positives is presented. Examples relate to detection of THC concentrations in breath samples with adequate performance for determining recent use.

Definitions

Assay dose response: Function which relates measured Signal as a function of analyte concentration for an assay.

Assay precision: Standard deviation of signal measured for one analyte concentration.

Analytical performance: Includes both dose response and precision.

Distribution of true positives: Histogram of analyte concentration distributions measured from samples which are known to be from subjects who would be considered "positive" for a certain condition. For this project, the true positive cohort consists of subjects who have inhaled or ingested *cannabis* products with some period.

Diagnostic performance: Measure of accurately predicting a Positive or Negative result. This is general quantified by Sensitivity and Specificity, which are measures of true positive rate and true negative rate respectively Cutoff: A concentration (or signal) value selected as part of the assay, which is used to diagnose a sample as either positive or negative.

Recent use: Defined for this project as 2 hours after the cessation of smoking.

Methodology

Analytical performance for the assay is established by empirically determining the assay dose response and precision. This is accomplished by preparing samples with a range of analyte concentrations which mimic the distribution of the true positive samples. Replicate measurements are made at each concentration level, from which the standard deviation, $\sigma_s$, can be calculated. The outputs from this experiment are functions for dose response and precision, $S=f(C)$; $\sigma_s=g(S)$.

Next, a distribution of true positives is determined. This is typically done by conducting a study on real subjects who are part of the population of interest. A positive/negative diagnosis is made using an independent method, which acts as the "true" diagnosis. The assigned condition (positive/negative) becomes the true diagnosis for the patient. A distribution of true positives and true negatives is thus determined.

To estimate the diagnostic performance of an assay, a virtual cohort of subjects is created and assigned analyte concentrations by random sampling from both true positive and true negative distributions. Each subject in the cohort has an assigned true diagnosis (positive/negative) determined independently. For each subject, the analyte concentration is propagated through the dose response to calculate a mean signal, and noise is randomly added based on the standard deviation of the assay at the respective signal value. This "generated" signal is compared to the signal cutoff selected, based on which, the assay diagnosis (positive/negative) is made. For each subject, assay diagnosis is compared to the true diagnosis, and the result is grouped into four buckets—True Positive (TP), True Negative (TN), False Positive (FP), and False Negative (FN). From these the sensitivity and specificity are calculated as:

Sensitivity=Sum of True Positives/(Sum of True Positives+Sum of False Negatives)

Specificity=Sum of True Negatives/(Sum of True Negatives+sum of False Positives)

The method described can be used to calculate Sensitivity and Specificity based on a certain cut-off, or determine a cut-off based on requirements of Sensitivity and Specificity.

The following example illustrates the method described above. The assay in this example is an Antigen-down, 2Ab Immunoassay for THC. The dose response for this assay follows a 5-parameter Logistic function. Experimental data points can be plotted and a line theoretically fit. For this example, the theoretical fit is used to calculate signal at an arbitrary concentration.

For the noise model, standard deviations at each concentration level were calculated across 3-4 replicates. For this data set, the noise model was calculated to be $\sigma_s$=0.05 S.

To calculate distribution of analyte concentrations in samples taken from the population of interest, data from office studies was used. Mass spec concentrations measured in breath samples collected from subjects at time points greater than 60 min after smoking *cannabis* was used to construct a concentration distribution. This empirical distribution was fit to a theoretical distribution function. It was found that an exponential distribution fit the data well. The cumulative distribution for this data can be described by a simple function, $P(c \le c_0) = 1 - \exp(-c_0/452.5)$.

Diagnostic Performance as a Function of Cut-Off

Using the assay analytical performance and distribution of concentrations described above as inputs, sensitivity/specificity can be calculated as a function of cut-off. All calculations were done in R, an open-source programming language (https://cran.r-project.org/). The calculation steps are detailed below:
1. 10,000 virtual samples were created, and each was assigned a mass of THC, randomly sampling from the exponential distribution described above.
2. A range of cut-off mass between 1 pg and 1000 pg was chosen for calculating assay diagnostic performance.
3. A cut-off value is selected. Based on the selected cut-off, each sample is assigned a "true" diagnosis—positive or negative. In a real application, this cutoff would be determined independently (e.g., 0.08 for Blood Alcohol Content).
4. The corresponding signal value at the selected cut-off is calculated by using the dose response profile. This is the cut-off signal value for the assay. In actual use, the signal cut-off is chosen to be the signal at the cut-off concentration defined in #3.
5. For each of the 10,000 virtual samples, their corresponding THC mass is converted into a signal value using the dose response. A random noise is added to the mean signal based on the noise model. This is done by sampling a Gaussian distribution with mean given by the signal value, and SD given by the noise model.
6. The calculated signal values are compared against the cut-off signal value, and an "assay" diagnosis is assigned.
7. Assay and true diagnoses are compared for all samples, and sensitivity/specificity values are calculated.
8. Steps 4-7 are repeated for all cut-off mass values.

The results from this simulation indicate a value of 0.9, which is arbitrarily selected as an acceptable passing mark for both sensitivity and specificity. It is seen that sensitivity drops sharply with higher concentrations. Specificity is noisier, which is mostly due to insufficient statistics, especially at low cut-off values. Based on this example, this assay has acceptable diagnostic performance at a range of cut-off values between 1 and 100 pg. As a corollary to this, if the cut-off value is independently set at 10 pg, the assay has a sensitivity of 0.99 and a specificity of 0.91.

A reliably detectable pg-level threshold (e.g., 10-25 pg THC/5 L of breath (2-5 pg/L)) that is believed to correlate to THC impairment, or at least recent use, has been determined.

Example 2

A summary of details about the materials and processes used in an example immunoassay method for detecting THC in breath samples is presented.

Materials

Primary (anti-THC antibody): There are two broad types of Antibodies used in Immunoassays—Polyclonals and Monoclonals. Polyclonal antibodies are more diverse and can detect a wider range of molecules. This makes them insensitive to minor changes to molecular structure, which can be important for a small molecule such as THC. Monoclonal antibodies are highly specific to the exact antigen. They are also more consistent from batch to batch since they mostly consist of one type of antibody. As a result, they can be produced by synthetic methods (e.g., Hybridomas).

For detection of THC from breath, either type of antibody can be used. Since breath samples are quite clean, especially after filtering out any saliva, molecular variants and other proteins which can bind to the anti-THC antibody are mostly absent. The selection of antibody for THC is mostly driven by practical considerations such as availability, lot-to-lot consistency, etc. A variety of suitable commercially available kits may be adapted for this use, including MaxSignal-THC-ELISA-Test-Kit or Cannabinoids ELISA Kit, available from mybiosource.com, or others available from fitxgerald-fii.com, novusbio.com and biossusa.com.

Antigen: Synthetic THC (Delta 8-, Delta 9-) or any of its variants (THCA, for example) can be directly adsorbed on to the surface for the antigen-down formats. THCA may offer some advantages over THC since it has a higher resistance to oxidation. The choice between Delta 8- or Delta 9- in conjunction with selection of antibody allows one to fine-tune the relative binding affinities between the antibody and the competitive antigen v/s antibody and the sample. THC/THCA can also be conjugated to a protein such as BSA to enhance strength of adsorption to the immobilization surface.

Reporter: For good sensitivity at low analyte concentrations, fluorescence and luminescence are the preferred signal generation schemes, since both methods offer good low-end sensitivity. Luminescence has the further advantage from a system perspective of not requiring an illumination source and spectral filters. Among luminescence reporters, Horseradish Peroxidase (HRP) and Alkaline Phosphatase (AP) are most commonly used. AP is a better candidate in formats where the total reporter concentration is low.

In a competitive assay, absolute concentrations of reporter enzyme are relatively high. In this case, HRP may be a better choice since it has much faster kinetics allowing for shorter assay times.

Assay Optimization

Clinical data can be used to define the optimal cut-off concentrations for THC detection. A primary goal of assay optimization is to maximize modulation (slope of the dose-response curve) at this desired cut-off concentration. In addition to selection of the different components (discussed above), the concentration of reagents can be optimized to maximize modulation. Two parameters to be optimized are (1) Ratio of analyte concentration in sample to the concentration of competitive antigen and (2) Ratio of concentration of competitive antigen to concentration of primary antibody.

For a qualitative assay with a defined cut-off concentration, when the competitive antigen and primary antibody concentrations are of the same order of magnitude (in Molar concentrations) as the cut-off concentration it results in the dose response curve having a maximum slope at the cut-off to maximize assay sensitivity and specificity.

Based on models, it is estimated that the maximum dose response is achieved by maintaining a primary antibody concentration which is in excess of the target analyte concentration, while keeping a molar ratio of close to unity for the competitive antigen and the primary antibody.

The optimization process involves varying concentrations of competitive antigen and primary antibody until a maximum is observed in the dose response curve at the cut-off concentration. Mathematical models can be used as a starting guess for these concentrations, which are fine-tuned by experimental data.

THC Immunoassay in a Flowcell

A flowcell may be used as the reaction geometry for the immunoassay. The flow cell will have an inlet and outlet port. A fluid manifold acts as the reservoir for all reagents, and directs fluid to and from both the flowcell and the breath collection module (BCM). The detector directly reads the final signal from the flow cell.

Miniature flowcells, having cross-sectional dimensions of about 100 um-few millimeters, are a good platform for immunoassays. The small dimensions of the flow channel results in a high surface area to volume, which is favorable for surface reactions such as those in immunoassays. Custom flowcells may be fabricated to integrate with particular microfluidics architecture.

Prior to using the flowcell for a THC assay, the flowcell is coated with the surface moiety (antigen or anti-body depending on the format). In this example, an antigen-down format is assumed. The antigen is diluted to working concentration, and is flown into the flowcell, ensuring that the flow cell is completely filled. This is followed by incubation to ensure that the antigen is immobilized onto the surface. Any excess antigen is washed away by flowing a buffer solution through the flowcell multiple times. A blocking buffer is then introduced into the flowcell and incubated, to cover any bare surfaces which are not occupied by the antigen. This reduces non-specific binding and improves assay precision. The blocking step is particularly important in the flowcell geometry, due to the high surface area/volume ratio, which facilitates both specific and non-specific binding. The flow cell is finally washed and dried, and is ready for use.

Sample, diluted to an appropriate concentration, is introduced into the coated flow cell, and allowed to bind with the coated antigen. The rest of the assay process is like a standard microtiter plate assay. The volumes used in the flowcell may be considerably lower (about 10-50 uL) compared to what is used in a standard 96-well microtiter plate (about 100-200 uL).

The final signal is generated in the flow cell, which is read by a detector positioned either underneath or above it. The footprint of the complete device can be very small due to the small dimensions of the flowcell.

Assay and Process Optimization

Transitioning the assay from a standard microtiter plate to a flow cell may involve further optimization of reagents and processes. As briefly stated before, the blocking step can be important in ensuring that non-specific binding is minimized. Both the concentration and composition of the blocker might have to be modified to maximize dose response and minimize variability. The wash steps during the assay also enhance the performance of the assay. Wash parameters such as number of wash steps, composition of wash buffer, flow rates, residence times, etc. are all important to the performance. These steps may be optimized empirically.

Example 3

THC in Breath: Data from Development of a Marijuana Breathalyzer

THC is detected in breath for about 2-3 hours on average. Data on breath THC was collected after smoking indoors or outdoors, rather than in a laboratory setting. People have high levels of THC in their breath immediately after smoking. Breath THC drops to almost zero after 2-3 hours. Studies by the National Institute of Health (NIH) in 2013 and a European group in 2016 show a similar 2-3 hour time period. The 2-3 hours that THC is measured in breath correlates to the window of greatest impairment, as defined by NHTSA. The data were collected in 430 tests, more than all published studies combined. All samples were collected using a device developed by Hound Labs, Inc. and analyzed using mass spectrometry (MS).

Frequent smokers have virtually no THC in their breath if they have not smoked for several hours. Baseline breath THC in chronic smokers was found to be a maximum of 12 pg/5 L breath. A suitable breathalyzer can be calibrated so that very low THC levels will not trigger a positive test. This means frequent smokers—who often have substantial THC in their saliva, blood and urine long after the 2-3 hour window of impairment—do not have appreciable THC in breath after 2-3 hours and will not test positive on such an appropriately calibrated device.

The precise level of THC in breath is not important. Unlike alcohol, someone with a higher level of THC in breath is not necessarily "more stoned" than someone with a lower level. Environment plays an important role in THC breath levels. People who stay indoors after smoking have much higher levels than those who go outdoors—their peak levels may be 100 times higher. But breath THC levels drop substantially once they are outside, even though impairment is not affected by being outdoors versus indoors. A marijuana breathalyzer should be ultrasensitive so that it can accurately detect people who smoke outdoors, where levels often are very low during the 2-3 hour window of impairment.

People exposed to secondhand smoke will only have THC in their breath for a very brief time, and it disappears after a person is no longer exposed to this smoke. It is important that people exposed to second hand smoke be placed outdoors or in a well-ventilated area for 15 minutes before a breath test is performed. This is akin to alcohol testing, where the subject is observed for a minimum of 15 minutes so that alcohol in mouth vapors (which may dramatically elevate the level) dissipates before the breathalyzer is administered.

The science necessary to measure THC in breath is enormously complex. THC is measured in parts per trillion (picograms, pg), which means it is up to one billion times less prevalent in breath compared to alcohol. To put it another way, measuring THC in breath is like cutting a single raisin into 1 trillion pieces or finding one specific drop of water in 20 full sized Olympic swimming pools. The level of sensitivity required to measure THC is unprecedented.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the claims are not intended to be limited to the embodiments shown herein but are to be accorded the widest scope consistent with the claims and the principles and novel features disclosed herein.

It is to be understood that the above disclosure, while focusing on a particular example implementation or implementations, is not limited to only the discussed example, but may also apply to similar variants and mechanisms as well, and such similar variants and mechanisms are also considered to be within the scope of this disclosure.

What is claimed is:

1. A cartridge for use in obtaining breath samples for analysis to detect an analyte, wherein the cartridge is configured to separately and releasably interface with a handheld sample collection unit and a base station, the cartridge comprising:
    one or more sample ports;
    a first reaction channel, a second reaction channel, and a third reaction channel, the one or more sample ports fluidically connectable within the cartridge with the first reaction channel, wherein the cartridge is configured to facilitate analysis within the second reaction channel of a first control for the analyte contained within the cartridge and analysis within the third reaction channel of a second control for the analyte; and
    one or more pumping assist ports, the one or more pumping assist ports fluidically connected to the first reaction channel within the cartridge by one or more flow paths and positioned so as to interface, when the cartridge is interfaced with the handheld sample collection unit, with a suction port on the handheld sample collection unit that is fluidically connected with a suction pump within the handheld sample collection unit.

2. The cartridge of claim 1, further comprising one or more optical measurement sites, the optical measurement sites positioned within the cartridge so as to align with an optical measurement module of the base station when the cartridge is interfaced with the base station, wherein at least a portion of the cartridge that is between each optical measurement site and the optical measurement module when the cartridge is interfaced with the base station is transparent.

3. The cartridge of claim 1, wherein the first reaction channel having a hydraulic diameter (d) between 0.1 mm and 1 mm.

4. The cartridge of claim 3, wherein the first reaction channel has a length that is between 15 $\mu L/d^2$ and 45 $\mu L/d^2$.

5. The cartridge of claim 1, wherein the first reaction channel has a volume of between 15 µL and 100 µL.

6. The cartridge of claim 1, wherein the first reaction channel has a hydraulic diameter less than 1 mm.

7. The cartridge of claim 1, further comprising:
    a first blister containing a predetermined amount of a first substrate;
    a second blister containing a predetermined amount of a second substrate;
    a third blister containing a predetermined amount of a first buffer;
    a fourth blister containing a predetermined amount of a wash fluid; and
    a reservoir containing a predetermined quantity of lyophilized antibody that is selected to bind with the analyte.

8. The cartridge of claim 7, wherein the analyte is tetrahydrocannabinol (THC) and the lyophilized antibody is a horseradish peroxidase (HRP) conjugated monoclonal antibody that is specific to cannabinol.

9. The cartridge of claim 2, wherein one of the one or more optical measurement sites is part of the first reaction channel.

10. The cartridge of claim 1, further comprising a memory device, the memory device configured to store data pertaining to a breath sample collected using the cartridge in an encrypted format.

11. The cartridge of claim 7, wherein the first blister contains a substance selected from the group consisting of TMB (3,3',5,5'-tetramethylbenzidine), OPD (o-phenylenediamine), and ABTS (2,2'-Azinobis [3-ethylbenzothiazoline-6-sulfonic acid]).

12. The cartridge of claim 1, further comprising:
    a plurality of fluid flow channels within the cartridge and arranged to transport fluid between different locations within the cartridge; and
    a plurality of valve membranes, wherein:
        each valve membrane is positioned along one of the fluid flow channels, and each of the valve membranes is arranged to allow for selective enablement or disablement of a different portion of the fluid flow channels responsive to an actuation input.

13. The cartridge of claim 7, further comprising:
    a first reservoir configured to receive the first substrate when the first substrate is expelled from the first blister;
    a second reservoir configured to receive the second substrate when the second substrate is expelled from the second blister;
    a third reservoir configured to receive the first buffer when the first buffer is expelled from the third blister; and
    a fourth reservoir configured to receive the wash fluid when the wash fluid is expelled from the fourth blister.

14. The cartridge of claim 1, wherein the cartridge further comprises an evidence receptacle configured to receive a portion of fluid that is received via the one or more sample ports when fluid is directed through the one or more sample ports.

15. The cartridge of claim 7, further comprising a substrate mixing reservoir configured to receive the first substrate from the first blister and the second substrate from the second blister, wherein the substrate mixing reservoir is:
    a) fluidically interposed between the first reaction channel and the first blister, and
    b) fluidically interposed between the first reaction channel and the second blister.

16. The cartridge of claim 10, wherein the memory device is configured to store one or more pieces of data selected from the group consisting of: test subject name, test subject age, test subject driver's license number, test subject social security number, test subject date of birth, test subject photograph, test subject fingerprint, test subject signature, test subject voiceprint, ambient temperature, ambient humidity, ambient barometric pressure, identifying information of a person taking a sample, time and date of sample collection, location of sample collection, amount of breath sample passed through the cartridge, a duration of sample collection using the cartridge, measured levels of one or more analytes collected using the cartridge, and combinations of any two or more of the above.

17. The cartridge of claim 1, further comprising a blood alcohol concentration (BAC) port that is positioned so as to fluidically connect with a BAC sensor in the handheld sample collection unit when the cartridge is interfaced with the handheld sample collection unit, wherein the BAC port is fluidically connected with the one or more sample ports within the cartridge.

18. The cartridge of claim 1, wherein the first reaction channel, the second reaction channel, and the third reaction channel are each of the same size and shape.

19. The cartridge of claim 18, wherein the first reaction channel, the second reaction channel, and the third reaction channel are parallel to each other.

20. The cartridge of claim 1, wherein the cartridge further includes a breath inlet port configured to interface with a removable mouthpiece, wherein the one or more sample ports are fluidically interposed between the breath inlet port and the first reaction channel.

21. The cartridge of claim 20, further comprising the removable mouthpiece, wherein the removable mouthpiece is connected with the breath inlet port such that the breath inlet port is fluidically interposed between the removable mouthpiece and the one or more sample ports.

* * * * *